(12) United States Patent
Cheng et al.

(10) Patent No.: US 7,662,587 B1
(45) Date of Patent: Feb. 16, 2010

(54) GENE KNOCKOUT MUTATIONS THAT INCREASE PEPTIDE PRODUCTION

(75) Inventors: Qiong Cheng, Wilmington, DE (US); Kevin Michael Croker, Hockessin, DE (US); Kristin Ruebling-Jass, Wilmington, DE (US); Hong Wang, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/398,358

(22) Filed: Mar. 5, 2009

(51) Int. Cl.
*C12P 21/06* (2006.01)
*C12P 21/04* (2006.01)
*C12P 1/00* (2006.01)
*C12N 15/74* (2006.01)

(52) U.S. Cl. .................... 435/69.1; 435/69.7; 435/41; 435/183; 435/440; 435/471

(58) Field of Classification Search ............... None
See application file for complete search history.

(56) References Cited

OTHER PUBLICATIONS

Wilson et al. Journal of Bacteriology 1993, vol. 175, No. 16, pp. 5129-5134. Role of the GcvA and PurR Proteins in Negative Regulation of the *Escherichia coli* Glycine Cleavage Enzyme System.*
Ghrist et al. Microbiology (2001), 147, 2215-2221. GcvR interacts with GcvA to inhibit activation of the *Escherichia coli* glycine cleavage operon.*
Chen et al., Biotechnology and Bioengineering, 85(5):463-474 (2004).
Baba et al., Molecular Systems Biology, Article No. 2006.0008 (2006).

* cited by examiner

*Primary Examiner*—Andrew Wang
*Assistant Examiner*—Kagnew H Gebreyesus

(57) ABSTRACT

Disrupting the expression of endogenous *Escherichia* host cell genes gcvA and spr provides mutant host cells having increased heterologous peptide production relative to control *Escherichia* host cells. Recombinant *Escherichia* host cells are provided as well as methods of using such host cells for heterologous peptide production.

19 Claims, 2 Drawing Sheets

GENE KNOCKOUT MUTATIONS THAT INCREASE PEPTIDE PRODUCTION

FIELD OF THE INVENTION

The invention relates to the filed of molecular biology, microbiology, and recombinant peptide production. More specifically, it has been discovered that disrupting expression of the genes gcvA and spr or a combination thereof in *Escherichia* host cells significantly increases the production of recombinant production.

BACKGROUND OF THE INVENTION

Efficient production of bioactive proteins and peptides is a primary function of the biomedical and industrial biotechnology industry. Bioactive peptides and proteins are used as curative agents in a variety of diseases such as diabetes (insulin), viral infections and leukemia (interferon), diseases of the immune system (interleukins), and red blood cell deficiencies (erythropoietin), to name a few. Additionally, large quantities of proteins and peptides are needed for various industrial applications including, but not limited to pulp and paper industries, textiles, food industries, personal care and cosmetics industries, sugar refining, wastewater treatment, production of alcoholic beverages and as catalysts for the generation of new pharmaceuticals.

In biomedical-related fields small peptides are sometimes used as linkers for the attachment of diagnostic and pharmaceutical agents to surfaces (see U.S. Pat. App. Pub. No. 2003/0185870 to Grinstaff et al., and U.S. Pat. No. 6,620,419 to Linter). In the field of personal care, small peptides have been used to couple benefit agents to body surfaces such as hair, skin, nail, and teeth (U.S. Pat. Nos. 7,220,405; 7,309,482; 7,129,326; and 7,285,264; U.S. Pat. App. Pub. Nos. 2002/0098524; 2005/0112692; 2005/0226839; 2007/0196305; 2006/0199206; 2007/0065387; 2008/0107614; 2007/0110686; and 2006/0073111; and Int'l App. Pub. Nos. WO2008/054746; WO2004/048399, and WO2008/073368).

Peptides may be prepared by chemical synthesis or isolated from natural sources. However, these methods are often expensive, time consuming, and characterized by limited production capacity. The preferred method of producing large quantities of peptides or proteins is through the fermentation of recombinant microorganisms engineered to express genes encoding the peptide or protein of interest. However, recombinant microbial peptide production has a number of obstacles to be overcome in order to be cost-effective. For example, peptides produced within recombinant microbial host cell are often degraded by endogenous proteases, which decrease the yield and increase the cost of production. Additionally, microbial production of smaller peptides in high yield may be adversely affected by size and the amino acid composition of the peptide. This is especially evident when the peptide of interest is soluble under typical physiological conditions found within the production host.

One way to mitigate the difficulties associated with recombinant peptide production is the use of chimeric genetic constructs encoding heterologous proteins. Also called fusion proteins, the heterologous proteins typically comprise at least peptide/protein of interest linked to at least one peptide tag. Linking the protein of interest [POI] to the peptide tag, also called solubility tag or inclusion body tag can make the POI insoluble. The peptide tag may be used to assist protein folding, post expression purification (e.g. His tags), protein passage through the cell membrane as well as to protect the peptide or protein from the action of degradative enzymes found within the cell.

Expressing a peptide in an insoluble form by fusing it to a solubility tag-even when the peptide is soluble at normal physiological conditions—facilitates recovery and protects the peptide from degradation. The fusion protein may include at least one cleavable peptide linker separating the solubility tag from the peptide of interest to facilitate subsequent recovery of the POI from the fusion protein. The fusion protein may include a plurality of inclusion body tags, cleavable peptide linkers, and regions comprising the peptide of interest.

Increasing the expression level of the gene encoding the POI can increase the POI yield, e.g., by chromosomal integration of multiple copies of the gene, use of a stronger promoter, and/or by using a high copy expression plasmid. However, the use of high copy plasmids often places an undesirable metabolic burden on the host cell.

Mutations to periplasmic proteases have been reported to increase recombinant antibody fragment accumulation in the *E. coli* periplasm (Chen et al., *Biotech Bioengin* (2004) 85 (5):463-474. Even though single gene knockout libraries are available for *E. coli* (Baba, T., et al., (2006) *Mol. Syst. Biol.* 2: article 2006.0008), down-regulating or disrupting specific genes or combinations of genes in *E. coli* that significantly increase heterologous peptide production are not as well known.

The problem to be solved is to provide *Escherichia* cells comprising knockout mutations to endogenous genes that increase the amount of a heterologous peptide produced within the host cell and methods of increasing recombinant production of a peptide of interest in the recombinant host cell comprising the down-regulated and/or disrupted endogenous gene(s).

SUMMARY OF THE INVENTION

The stated problem has been solved through the discovery that disrupting expression of a gene selected from the group consisting gcvA, spr, and a combination of both in an *Escherichia* host cell increases heterologous peptide production.

sDescribed herein are recombinant *Escherichia* host cells comprising: i) a chimeric genetic construct encoding a peptide of interest;

ii) a knockout mutation in gene gcvA; and iii) a knockout mutation in gene spr.

Also described herein are methods of producing a peptide of interest in an *Escherichia* host cell comprising:

a) providing an *Escherichia* host cell comprising
 i) at least one chimeric genetic construct encoding a peptide of interest; and
 ii) a knockout mutation selected from the group consisting of gene gcvA, gene spr and a combination of both;

b) growing the *Escherichia* host cell of (a) to produce a peptide of interest; and c) optionally recovering the peptide of interest produced in step (b).

The described recombinant *Escherichia* host cell may lack a down-regulated or disrupted copy of an endogenous protease gene selected from t degP, prc, ompT, ptr3, or combinations of these. The recombinant *Escherichia* host cell may further comprise down-regulation or a disruption in the expression of the endogenous araBAD operon, slyD gene, or a combination thereof.

BRIEF DESCRIPTION OF THE BIOLOGICAL SEQUENCES

Figure 1:
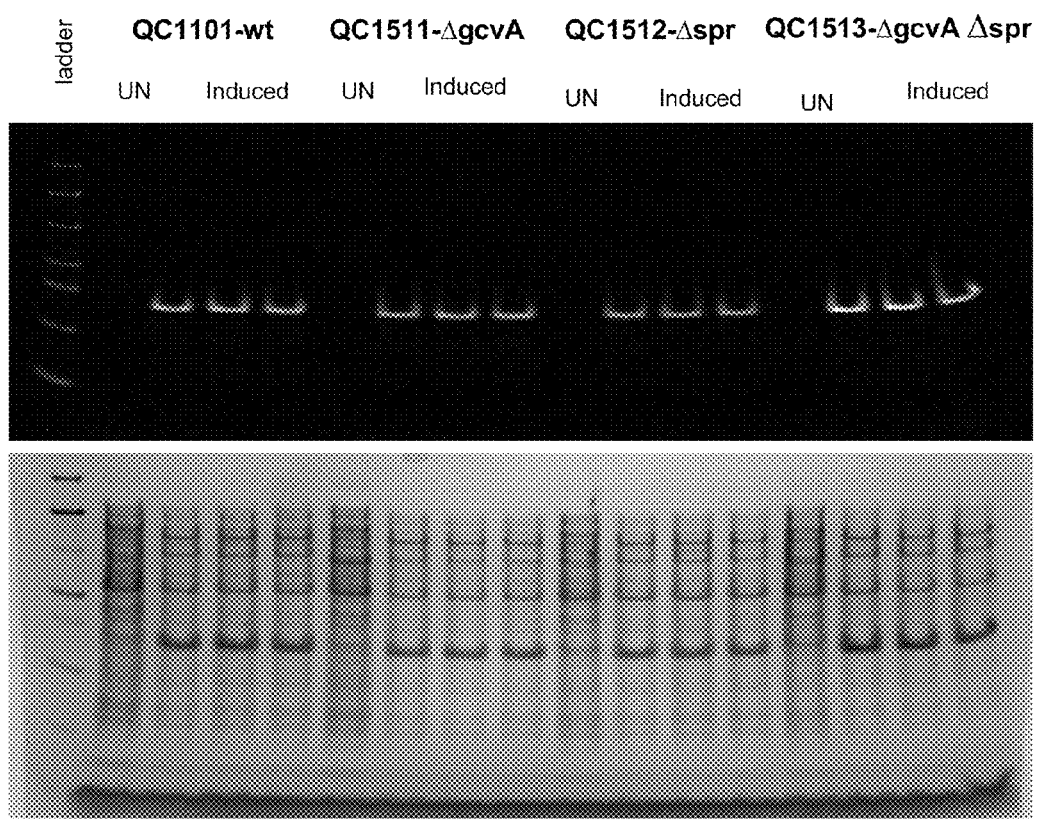
FIG. 1 shows the gel pictures (top and bottom panels) of the triplicate cultures of QC1101-wt, QC1511-ΔgcvA, QC1512-Δspr, and QC1513-ΔgcvA Δspr loaded same volume of the normalized $OD_{600}$ 1 cultures as described in Example 4. The molecular weight ladder is shown in the far left lane. "UN" means uninduced cells (cells prior to induction). Top panel shows the specific in-gel labeling of the fusion peptide viewed under the UV light. The same gel stained with SIMPLYBLUE™ is also shown on the bottom panel.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NO: 1 is the amino acid sequence of a tetracysteine tag that binds to a biarsenical labeling reagent.

SEQ ID NO: 2 is the nucleic acid sequence of peptide expression plasmid pLR199.

SEQ ID NO: 3 is the amino acid sequence of inclusion body tag IBT139.

SEQ ID NO: 4 is the amino acid sequence of a peptide of interest, HC776124.

SEQ ID NO: 5 is the nucleic acid sequence encoding the fusion peptide IBT139-HC776124.

SEQ ID NO: 6 is the amino acid sequence of the fusion peptide IBT139-HC776124.

SEQ ID NO: 7 is the nucleic acid sequence of plasmid pDCQ523.

SEQ ID NO: 8 is the amino acid sequence of inclusion body tag IBT139(5C).

SEQ ID NO: 9 is the nucleic acid sequence of fusion peptide IBT19(5C)-CCPGCC-HC415.

SEQ ID NO: 10 is the amino acid sequence of fusion peptide IBT139(5C)-CCPGCC-HC415.

SEQ ID NO: 11 is the nucleic acid sequence of peptide HC415.

SEQ ID NO: 12 is the amino acid sequence of peptide HC415.

SEQ ID NO: 13 is the nucleic acid sequence of primer Kan2cb-For.

SEQ ID NO: 14 is the nucleic acid sequence of primer Kan2cb-Rev.

SEQ ID NO: 15 is the nucleic acid sequence of gcvA.

SEQ ID NO: 16 is the amino acid sequence of GcvA.

SEQ ID NO: 17 is the nucleic acid sequence of spr.

SEQ ID NO: 18 is the amino acid sequence of Spr.

SEQ ID NO: 19 is the amino acid sequence of a peptide linker.

SEQ ID NO: 20 is the nucleic acid sequence of the araB promoter.

SEQ ID NO: 21 is the nucleic acid sequence of the coding sequence for the slyD gene in Escherichia coli strain K-12 substrain MG1655.

SEQ ID NO: 22 is the amino acid sequence of the SlyD protein in Escherichia coli strain K-12 substrain MG1655.

SEQ ID NO: 23 is the amino acid sequence of the Caspase-3 cleavage site.

SEQ ID NOs: 24-270 are the amino acid sequences of various body surface-binding peptides are shown in Table A. SEQ ID NOs: 24-180 bind to hair, SEQ ID NOs: 176-228 bind to skin, SEQ ID NOs: 229-230 bind to nail, and SEQ ID NOs: 231-2270 bind to a tooth surface, wherein SEQ ID NOs: 231-2250 bind to tooth pellicle and SEQ ID NOs: 251-270 bind to tooth enamel.

SEQ ID NOs: 271-329 are the amino acid sequences of polymer-binding peptides as shown in Table A.

SEQ ID NOs: 330-333 are the amino acid sequences of cellulose acetate-binding peptides.

SEQ ID NOS: 334-388 are the amino acid sequences of pigment-binding peptides as shown in Table A.

SEQ ID NOs:389-400 are the amino acid sequences of print media-binding peptides as shown in Table A.

SEQ IS NOs: 401-415 are the amino acid sequence of clay-binding peptides.

SEQ ID NOs: 416-441 are calcium carbonate-binding peptides.

SEQ ID NOs: 442-470 are the amino acid sequences of various antimicrobial peptides (U.S. Pat. No. 7,427,656).

DETAILED DESCRIPTION

Disrupted expression of the endogenous Escherichia genes gcvA and, spr increased heterologous peptide production in the mutant host cell. Provided herein are mutant Escherichia host cells having decreased and/or disrupted expression in gcvA and spr for use as peptide production hosts. The recombinant E. coli host cells may lack any genetic modification, such as disrupted expression, to the endogenous protease genes degP, prc, ompT, ptr3, and combinations thereof.

The heterologous peptides produced within the microbial host cell may be produced and accumulate in the form of inclusion bodies. The soluble single chain peptides may be fusion peptides comprising at least one solubility tag (inclusion body tag). The single chain peptide may range in size from about 14 to about 600 amino acids in length and lack any immunoglobulin folds. As such, the heterologous peptide of interest is not an immunoglobulin.

The following definitions are used herein and should be referred to for interpretation of the claims and the specification. Unless otherwise noted, all U.S. Patents and U.S. Patent Applications referenced herein are incorporated by reference in their entirety.

As used herein, the indefinite articles "a" and "an" preceding an element or component of the invention are intended to be nonrestrictive regarding the number of instances (i.e., occurrences) of the element or component. Therefore "a" or "an" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. This means a composition, a mixture, a process, a method, an article, or an apparatus that comprises a list of elements is not limited to only those elements but may include others not expressly listed or inherent to it. As used herein, "or" refers to an inclusive and an exclusive "or". For example, a condition A or B is satisfied by any one of the following: A is true (or present) and B is false (or not present), A is false (or not present) and B is true (or present), and both A and B are true (or present).

As used herein, the term "about" refers to modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "invention" or "present invention" is a non-limiting term and is intended to encompass all possible variations as described in the specification and recited in the claims.

As used herein, the terms "polypeptide" and "peptide" will be used interchangeably to refer to a polymer of two or more amino acids joined together by a peptide bond. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics. The peptides may comprise L-amino acids.

As used herein, the terms "peptide of interest", "POI", "gene product", "target gene product", and "target coding region gene product" refer to the desired heterologous peptide/protein product encoded by the recombinantly expressed foreign gene. The peptide of interest may include any peptide/protein product including, but not limited to proteins, fusion proteins, enzymes, peptides, polypeptides, and oligopeptides. The peptide of interest ranges in size from 14 to 600 amino acids in length. The peptide of interest is not GcvA or Spr. The peptide of interest may have strong affinity for a target surface, such as a body surface. The peptide of interest may have affinity for a body surface selected from the group consisting of hair, skin, nails, tooth, and tooth pellicle.

As used herein, the terms "bioactive" or "peptide of interest activity" refer to the activity or characteristic associated with the peptide and/or protein of interest. The bioactive peptides may be used as, for example, curative agents for diseases (e.g., insulin, interferon, interleukins, anti-angiogenic peptides (U.S. Pat. No. 6,815,426); polypeptides that bind to defined cellular targets such as receptors, channels, lipids, cytosolic proteins, and membrane proteins; peptides having antimicrobial activity; peptides having an affinity for a particular material (e.g., hair-binding polypeptides, skin-binding polypeptides, nail-binding polypeptides, tooth-binding peptides (include both tooth enamel and tooth pellicle-binding peptides), print media-binding peptides, cellulose-binding polypeptides, polymer-binding polypeptides, clay-binding polypeptides, calcium carbonate-binding peptides, cellulose acetate-binding peptides, carbon nanotube-binding polypeptides and peptides that have an affinity for particular animal or plant tissues) for targeted delivery of benefit agents.

As used herein, the "benefit agent" refers to a molecule that imparts a desired functionality or benefit when applied or coupled to a target surface. The present peptide reagents may be used to couple a benefit agent to a target surface, such as a body surface. The peptide reagent may couple a benefit agent to a body surface by forming a complex between the peptide reagent, the benefit agent, and the body surface. The peptide reagent is applied to the body surface prior to the application of the benefit agent (i.e., a sequential application). The benefit agent may be a peptide or the peptide reagent (e.g. condition peptides or antimicrobial peptides) or may be one or more molecules bound to (covalently or non-covalently), or associated with, a peptide reagent having affinity for a target surface. The benefit agent may be a particulate benefit agent. The term "particulate benefit agent' is a general term relating to a particulate substance, which when applied to a body surface provides a cosmetic or prophylactic effect. Particulate benefit agents typically include pigments, particulate conditioners, inorganic sunscreens and the like along with other particulate substances commonly used in the personal care industry.

As used herein, the term "$MB_{50}$" refers to the concentration of the binding peptide that gives a signal that is 50% of the maximum signal obtained in an ELISA-based binding assay (see Example 9 of U.S. Published Pat. App. Pub. No. 2005/0226839; hereby incorporated by reference). The $MB_{50}$ provides an indication of the strength of the binding interaction or affinity of the components of the complex. The lower the value of $MB_{50}$, the stronger the interaction of the peptide with its corresponding substrate.

As used herein, the terms "binding affinity" or "affinity" refers to the strength of the interaction of a binding peptide (e.g. a peptide having affinity for a specified target surface)) with its respective substrate. The binding affinity may be reported in terms of the $MB_{50}$ value as determined in an ELISA-based binding assay or as a $K_D$ (equilibrium dissociation constant) value, which may be deduced using surface plasmon resonance (SPR). The lower the value of $MB_{50}$ or $K_D$, the stronger affinity of the peptide interacting with its corresponding substrate.

As used herein, the term "strong affinity" refers to a binding affinity, as measured as an $MB_{50}$ or $K_D$ value, of $10^{-5}$ M or less, preferably $10^{-6}$ M or less, preferably less than $10^{-7}$ M, more preferably less than $10^{-8}$ M, more preferably less than $10^{-9}$ M, and most preferably less than $10^{-10}$ M.

As used herein, the term "target surface-binding peptide" refers to a single chain peptide having strong affinity (defined as having a $K_D$ value less than $10^{-4}$ M or an $MB_{50}$ value of less than $10^{-4}$) for a target surface. The peptide of interest may be a single target surface-binding peptide ranging in size from 7 to 60 amino acids in length, or may be a single chain, peptide-based reagent comprising one or more target surface-binding peptides, wherein the length of the peptide-based reagent ranges from 14 to 600 amino acids in length. The target surface-binding peptide may be a body surface-binding peptide.

As used herein, the term "body surface-binding peptide" refers to a peptide having strong affinity for a body surface. Examples of body surfaces include, but are not limited to hair, skin, nail, and tooth. The body surface-binding peptides are typically used to couple a personal or health care benefit agent to the body surface. These agents include colorants, conditioners, and antimicrobials, to name a few. Means to identify suitable body-surface binding peptides are well known in the art and may include biopanning techniques such as phage display, bacterial display, yeast display, ribosome display, and mRNA-display. The body surface-binding peptide may also be empirically-generated.

As used herein, "HBP" means hair-binding peptide. As used herein, the term "hair-binding peptide" refers to a peptide that binds with high affinity to hair. Examples of hair-binding peptides have been reported (U.S. patent application Ser. No. 11/074,473 to Huang et al.; Int'l App. Pub. No. WO 0179479; U.S. Pat. App. Pub. No. 2002/0098524 to Murray et al.; U.S. Pat. App. Pub. No. 2003/0152976 to Janssen et al.; Int'l App. Pub. No. WO 2004048399; U.S. patent application Ser. No. 11/512,910, and U.S. patent application Ser. No. 11/696,380). Examples of hair-binding peptides are provided as SEQ ID NOs: 24-180. The hair-binding peptides may be from about 7 amino acids to about 60 amino acids, more preferably, from about 7 amino acids to about 25 amino acids, most preferably from about 7 to about 20 amino acids in length.

As used herein, "SBP" means skin-binding peptide. As used herein, the term "skin-binding peptide" refers to a peptide sequence that binds with high affinity to skin. Examples of skin-binding peptides have also been reported (U.S. patent application Ser. No. 11/069,858 to Buseman-Williams; Int'l. App. Pub. No. WO 2004/000257; and U.S. patent application Ser. No. 11/696,380). Skin as used herein as a body surface will generally comprise a layer of epithelial cells and may additionally comprise a layer of endothelial cells. Examples of skin-binding peptides are provided as SEQ ID NOs: 176-228. The skin-binding peptides may be from about 7 amino acids to about 60 amino acids, more preferably, from about 7 amino acids to about 25 amino acids, most preferably from about 7 to about 20 amino acids in length.

As used herein, "NBP" means nail-binding peptide. As used herein, the term "nail-binding peptide" refers to a peptide that binds with high affinity to nail. Examples of nail-binding peptides have been reported (U.S. patent application Ser. No. 11/696,380). Examples of nail-binding peptides are provided as SEQ ID NOs: 229-230. The nail-binding peptides may be from about 7 amino acids to about 60 amino acids, more preferably, from about 7 amino acids to about 25 amino acids, most preferably from about 7 to about 20 amino acids in length.

As used herein, "TBP" means tooth-binding peptide. A tooth-binding peptide is a peptide that binds with high affinity to a mammalian or human tooth surface. As used herein, the term "tooth-binding peptide" will refer to a peptide that binds to tooth enamel or tooth pellicle. The tooth-binding peptides may be from about 7 amino acids to about 60 amino acids in length, more preferably, from about 7 amino acids to about 25 amino acids in length, most preferably from about 7 to about 20 amino acids in length. The tooth-binding peptides may be combinatorially-generated peptides. Examples of tooth-binding peptides having been disclosed in co-pending and co-owned U.S. application Ser. No. 11/877,692 and are provided as SEQ ID NOs: 231-270.

As used herein, the term "tooth surface" refers to a surface comprised of tooth enamel (typically exposed after professional cleaning or polishing) or tooth pellicle (an acquired surface comprising salivary glycoproteins). Hydroxyapatite can be coated with salivary glycoproteins to mimic a natural tooth pellicle surface (tooth enamel is predominantly comprised of hydroxyapatite).

As used herein, the terms "pellicle" and "tooth pellicle" refer to the thin film (typically ranging from about 1 μm to about 200 μm thick) derived from salivary glycoproteins which forms over the surface of the tooth crown. Daily tooth brushing tends to only remove a portion of the pellicle surface while abrasive tooth cleaning and/or polishing (typically by a dental professional) will exposure more of the tooth enamel surface.

As used herein, the terms "enamel" and "tooth enamel" refer to the highly mineralized tissue which forms the outer layer of the tooth. The enamel layer is composed primarily of crystalline calcium phosphate (i.e. hydroxyapatite; $Ca_5(PO_4)_3OH$) along with water and some organic material. The tooth surface may be tooth enamel or tooth pellicle.

As used herein, the terms "peptide linker", "linker" and "peptide spacer" refer to a peptide used to link together two or more target surface-binding peptides. An example of a peptide linker is provided as SEQ ID NO: 19.

As used herein, the term "bridge", "peptide bridge", and "bridging element" refer to a linear peptide used to couple a target-surface binding domain ("target surface-binding hand") to a peptide domain coupled to the surface of particulate benefit agent (i.e. covalent or non-covalent coupling). The peptide bridge may range in size from 1 to 60 amino acids in length, preferably 6 to 40 amino acids in length.

As used herein, the terms "coupling" and "coupled" refer to any chemical association and may include both covalent and non-covalent interactions in one coupling event. Coupling may also refer to separate, individual covalent interaction or separate, individual non-covalent interaction.

As used herein, the terms "hand", "target surface hand", and "target surface-binding domain" refer to a single chain peptide comprising of at least two target surface-binding peptides linked together by at least one peptide linker. The target surface-binding peptides may be biopanned from a random peptide library using a method selected from the group consisting of phage display, bacterial display, yeast display, ribosome display, and mRNA-display. The target-surface binding hand may comprise two target surface-binding peptides linked together by a peptide linker.

As used herein, the terms "peptide-based reagent" and "peptide reagent" refer to a single chain peptide comprising at least one target surface-binding domain having strong affinity for a target surface.

As used herein, the terms "body surface-binding hand" and "body surface-binding domain" refer to a single chain peptide comprising two or more body surface-binding peptides (BSBPs) linked together by at least one peptide linker. The body surface-binding domain may comprise two body surface-binding peptides linked together by a peptide linker.

As used herein, the terms "benefit agent-binding hand" or "benefit agent-binding domain" refer to a single chain peptide domain comprising two or more benefit agent-binding peptides (BABPS) coupled together by at least one peptide linker. The benefit agent-binding domain may comprise two benefit agent-binding peptides linked together by a peptide linker.

As used herein, the terms "solubility tag" and "inclusion body tag" and the abbreviation "IBT" refer to a polypeptide that promotes or enhances the formation of inclusion bodies when fused to a peptide of interest. The peptide of interest is typically soluble within the host cell and/or host cell lysate when not fused to an inclusion body tag. Fusion of the peptide of interest to the inclusion body tag produces a fusion protein that agglomerates into intracellular bodies, also called inclusion bodies, within the host cell. The fusion protein comprises a portion having an inclusion body tag and a peptide/protein of interest. The polypeptide/protein of interest may be separated from the inclusion body tags using cleavable peptide linker elements (See U.S. patent application Ser. Nos. 11/641,936, 11/641,273, and 11/782,836).

As used herein, the terms "cleavable linker element" and "cleavable peptide linker" are used interchangeably and refer to cleavable peptide segments typically incorporated between an inclusion body tag and the peptide of interest. After the inclusion bodies are separated and/or partially-purified or purified from the cell lysate, the cleavable linker element can be cleaved chemically and/or enzymatically to separate the inclusion body tag from the peptide of interest. The fusion peptide may also include a plurality of regions encoding one or more peptides of interest separated by one or more cleavable peptide linkers. The peptide of interest can then be isolated from the inclusion body tag, if necessary.

The inclusion body tag(s) and the peptide of interest may exhibit different solubilities in a defined medium, typically aqueous, thereby facilitating separation of the inclusion body tag from the peptide of interest. Preferably, the inclusion body tag is insoluble in an aqueous solution while the protein/peptide of interest is appreciably soluble in an aqueous solution. The pH, temperature, and/or ionic strength of the aqueous solution can be adjusted to facilitate recovery of the peptide of interest. The differential solubility between the inclusion body tag and the peptide of interest may occur in an aqueous solution having a pH of 5 to 10 and a temperature range of 15° C. to 50° C. The cleavable peptide linker may be from 1 to about 50 amino acids in length, preferably from 1 to about 20 amino acids in length. An example of an enzymatically cleavable peptide linker is provided by SEQ ID NO: 34 (Caspase-3 cleavage sequence). The cleavable linker may be an acid cleavable aspartic acid—proline dipeptide (D-P) moiety. The cleavable peptide linkers may be incorporated into the fusion proteins using any number of techniques well known in the art.

As used herein, the term "genetic construct" refers to a series of contiguous nucleic acids useful for modulating the genotype or phenotype of an organism. Non-limiting examples of genetic constructs include but are not limited to a nucleic acid molecule, and open reading frame, a gene, an expression cassette, a vector, a plasmid and the like.

As used herein, the term "endogenous gene" refers to a native gene in its natural location in the genome of an organism.

As used herein, a "foreign gene" refers to a gene not normally found in the host organism, but that is introduced into the host organism by gene transfer. Foreign genes can comprise native genes inserted into a non-native organism, or chimeric genes.

As used herein, the term "heterologous" with respect to sequence within a particular organism/genome indicates that the sequence originates from a foreign species, or, if from the same species, is substantially modified from its native form in composition and/or genomic locus by deliberate human intervention. Thus, for example, heterologous gene expression refers to the process of expressing a gene from one organism/genome by placing it into the genome of a different organism/genome.

As used herein, the term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

As used herein, the term "*Escherichia*" refers to a genus of Gram-negative, non-spore forming, facultatively anaerobic, rod-shaped bacteria from the family Enterobacteriaceae. The genus *Escherichia* include various species, such as *Escherichia coli*. The *Escherichia* host cell is an *Escherichia coli* cell. The *Escherichia coli* cell may be derived from an *Escherichia coli* K-12 strain.

As used herein, the term "peptide-based" refers to an interfacial material comprised of a compound pertaining to or having the nature or the composition of the peptide class. Interfacial refers to the quality of the peptide-based material described herein as connecting one material to another.

As used herein, the terms "fusion protein" and "fusion peptide" are interchangeable and refer to a polymer of amino acids (peptide, oligopeptide, polypeptide, or protein) comprising at least two portions, each portion comprising a distinct function. A first portion of the fusion peptide may comprise at least one inclusion body tag and a second portion of the fusion peptide may comprise at least one peptide of interest. The fusion protein may additionally include at least one cleavable peptide linker that facilitates chemical and/or enzymatic cleavage and separation of the inclusion body tag(s) and the peptide(s) of interest.

As used herein, the term "immunoglobulin fold" refers to a common all-β protein fold that consists of a 2-layer sandwich of ~7 antiparallel β-strands arranged in two β-sheets. The backbone switches repeatedly between the two β-sheets. Typically, the pattern is (N-terminal β-hairpin in sheet 1)-(β-hairpin in sheet 2)-(β-strand in sheet 1)-(C-terminal β-hairpin in sheet 2). The cross-overs between sheets form an "X", so that the N- and C-terminal hairpins are facing each other.

As used herein, the term "polymer-binding peptide" refers to peptide sequences that bind with high affinity to a specified polymer (U.S. patent application Ser. No. 11/516,362). Examples of polymer-binding peptides are provided as SEQ ID NOs: 271-329.

As used herein, the term "pigment" refers to an insoluble colorant and may include a wide variety of organic and inorganic pigments alone or in combination.

As used herein, the terms "iron oxide-based pigment" and "iron oxide pigment" refer to a pigment particle comprised primarily of an iron oxide. Iron oxide pigments may vary in color (red, yellow, brown, and black tones) due to minor impurities and/or the size of the pigment particle. The iron oxide pigment may be a cosmetically acceptable iron oxide pigment. Cosmetically acceptable iron oxide pigments are commercially available from various companies, such as Sensient Technologies Corp, Milwaukee, Wis. The iron oxide is selected from the group consisting of ferric oxide ($Fe_2O_3$), ferrous ferric oxide ($Fe_3O_4$), and mixtures of $Fe_2O_3$ and $Fe_3O_4$. The iron oxide may be ferric oxide $Fe_2O_3$. The iron oxide-based pigment may be at least partially coated with silica.

As used herein, the term "pigment-binding peptide" refers to a peptide that binds with high affinity to a pigment particle. Examples of pigment-binding peptides are provided in Table A as SEQ ID NOs 334-388.

As used herein, an "antimicrobial peptide" is a peptide having the ability to kill microbial cell populations (U.S. Pat. No. 7,427,656). Examples of antimicrobial peptides are provided as SEQ ID NOs: 442-470.

As used herein, the term "print medium-binding peptide" refers to a peptide that binds to a printer medium such as cotton, cellulose, paper, and cotton/polyester blends. Examples of print media-binding peptides are provided as SEQ ID NOs: 389-400.

As used herein, "clay-binding peptide" refers to a peptide that binds with strong affinity to clay (U.S. patent application Ser. No. 11/696,380). Examples of clay-binding peptides are provided as SEQ ID NOs: 401-415.

As used herein, "calcium carbonate-binding peptide" refers to a peptide that binds with strong affinity of calcium carbonate (U.S. patent application Ser. No. 11/828,539). Examples of calcium carbonate-binding peptides are provided as SEQ ID NOs: 416-441.

As used herein, the term "operably-linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). The definition of "operably linked" may also be extended to describe the products of chimeric genes. As such, "operably-linked" may also refer to the linking of two or more target surface-binding peptides by at least one peptide linker.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Miscellaneous (or as defined herein) | Xaa | X |

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5th Ed. Current Protocols and John Wiley and Sons, Inc., N.Y., 2002.

Decreased or Disrupted Expression of Endogenous *Escherichia* Genes

Described herein are methods of increasing the production of a fusion protein by disrupting both genes gcvA and spr in a recombinant *Escherichia* host cell which either natively or through genetic engineering encodes a protein of interest [POI]. The fusion protein includes at least one POI linked to a solubility tag (inclusion body tag) Once produced by the host cell, the fusion protein is insoluble at normal physiological conditions, thereby avoiding cellular protease of the POI. Also described herein are recombinant *Escherichia* host cells having disruptions in both genes gcvA and spr and which thereby increase the production of a fusion protein.

Several genes from a random transposon insertion library were identified as possibly responsible for increasing peptide production by measuring an increase in fluorescence. This was done by using a fluorescent labeling reagent to identify the fusion peptide production. The increase in fluorescence had been initially attributed to an increase in the amount of fusion peptide produced.

Further analysis confirmed that the amount of POI produced increased relatively to the control under identical conditions for the disrupted gcvA or spr gene. A knockout mutant containing mutations to both gene gcvA and gene spr significantly increased heterologous peptide production. The increase in heterologous peptide production may be at least 1.25 fold, 1.5 fold, 2.0 fold, 2.5 fold, 3.0 fold, 3.5 fold, 4.0 fold, 4.5 fold or 5.0 fold when compared to a control *Escherichia* cell essentially identical to the mutant host cell except for the knockout to gcvA and spr grown under identical conditions.

PCR analysis was performed to confirm the clean in-frame deletion of gcvA and spr. Decreased expression (including disrupted expression of the functional gene product) of gcvA and spr increased the amount of the heterologous fusion peptide, including the POI. As used herein, the terms "disrupted functional expression", "disrupted expression", and "disrupted gene" refer to a genetic modification to a specified gene that stops functional expression of the gene's product, such as an active enzyme, functional RNA, and/or functional regulatory protein.

Generally, disruption in the production a gene product can be accomplished by, e.g., an insertion, deletion, or substitution to a portion of the gene, which results in no or reduced formation of the active gene product. The disruption may preferably be a partial or complete deletion of the gene. A genetic modification that complete abolishes production of the gene product may be referred to as a "knockout" and may be denoted by the symbol "Δ".

For example, "Δspr" would refer to a knockout of the spr gene that complete disrupted production of a functional Spr protein.

When the sequence of the gene to be disrupted is known, down regulating gene expression is targeted gene disruption and involves creating genetic cassettes that include DNA to be inserted into the to-be-disrupted gene. This DNA is often a genetic marker and is flanked by sequence(s) having a high degree of homology to a portion of the targeted gene. Introduction of the cassette into the host cell results in insertion of the foreign DNA into the targeted gene via native DNA replication mechanisms of the cell (Hamilton et al., *J. Bacteriol.*, 171:4617-4622 (1989); Balbas et al., *Gene*, 136:211-213 (1993); Gueldener et al., *Nucleic Acids Res.*, 24:2519-2524 (1996); and Smith et al., *Methods Mol. Cell. Biol.*, 5:270-277 (1996)) and interferes with transcription of the targeted gene, which produces no mRNA transcripts from which to translate a gene product.

Down regulation of expression does not require completely eliminating all expression of the gene and its corresponding gene product. Targeted genes may be down-regulated using several other techniques known in the art. For example, target genes can be modified to be under the control of non-native promoters. When desired that a pathway and/or functional gene product operate at a particular point in a cell cycle or during a fermentation run, regulated or inducible promoters can replace the native promoter of the target gene. Similarly, the native or endogenous promoter can be modified to decrease gene expression. For example, endogenous promoters can be altered in vivo by mutation, deletion, and/or substitution (see, Kmiec, U.S. Pat. No. 5,565,350; Zarling et al., PCT/US93/03868).

Down regulating can involve antisense technology when the sequence of the target gene is known. Here, a nucleic acid segment from the desired gene is cloned and operably linked to a promoter such that the anti-sense strand of RNA will be transcribed. This construct is then introduced into the host cell and the antisense strand of RNA is produced, which inhibits gene expression by preventing the accumulation of mRNA that encodes the POI. Antisense technology is within the skill of the art. That is, a skilled artisan understands that achieving a downregulated expression through antisense genes involves the use of chimeric genes having various regulatory elements.

Besides targeted gene disruption and antisense technology, other downregulation methods exist that do not require knowing the sequence of the to-be-disrupted gene. For example, cells may be exposed to UV radiation and then screened for the desired phenotype. Mutagenesis with chemical agents is also effective for generating mutants and commonly used substances include chemicals that affect non-replicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., (hereinafter "Brock") or Deshpande, Mukund V., *Appl. Biochem. Biotechnol.*, 36:227 (1992) (hereinafter "Deshpande").

Transposon mutagenesis represents another non-specific method of gene disruption and is exemplified herein. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid molecule in the presence of the transposase, the transposable element will randomly insert into the nucleic acid molecule. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Nucleic acid hybridization may also be used to identify substantially similar nucleic acid sequences. The present nucleic acid molecules may be used to identify genes encoding substantially similar polypeptides/proteins expected to have similar function. Nucleic acid hybridization may be conducted under stringent conditions.

Substantially similar sequences are defined by their ability to hybridize, under the following stringent conditions (0.1× SSC, 0.1% SDS, 65° C. and washed with 2×SSC, 0.1% SDS followed by 0.1×SSC, 0.1% SDS, 65° C.) with a sequence selected from the group consisting of SEQ ID NOs. 15 and 17.

Each of the proposed modifications is well within the routine skill in the art (see Sambrook and Russell, supra). Moreover, the skilled artisan recognizes that substantially similar sequences are also encompassed by the present invention. Furthermore, the genetic modifications illustrated herein in *Escherichia Coli* should apply to other members of the genus *Escherichia*.

As illustrated herein, the *Escherichia* host cell may also have a knockout to the endogenous chromosomal araBAD operon (a pBAD expression vector and arabinose induction was used to drive expression of the chimeric gene encoding the fusion peptide) and a knockout to the slyD gene (to remove possible binding between the LUMIO™ biarsenical labeling reagent and cysteine rich sequences in slyD). The recombinant *Escherichia* production host may comprise decreased expression and/or a disruption (such as a knockout) in the endogenous araBAD operon, the slyD gene, or a combination thereof.

Peptide of Interest

The function of the peptide of interest is not limited by the present method and may include, but is not limited to bioactive molecules that act as curative agents for diseases, such as insulin, interferon, interleukins, peptide hormones, immunoglobulins, antibodies, anti-angiogenic peptides, and peptides that bind to and affect defined cellular targets such as receptors, channels, lipids, cytosolic proteins, and membrane proteins (see U.S. Pat. No. 6,696,089); peptides having an affinity for a particular material, such as biological tissues, biological molecules, hair-binding peptides (see U.S. patent application Ser. No. 11/074,473; Int'l Pat. App. No. WO 0179479; U.S. Pat. App. Pub. No. 2002/0098524; U.S. Pat. App. Pub. No. 2003/0152976; Int'l Pat. App. No. WO 04048399; U.S. Pat. App. Pub. No 2007/0067924; and U.S. Pat. App. Pub. No. 2007/0249805), skin-binding peptides (see U.S. Pat. No. 7,309,482; Int'l. Pat. App. No. WO 2004/000257; and U.S. Pat. App. Pub. No. 2007/0249805), nail-binding peptides (see U.S. Pat. App. Pub. No. 2007/0249805), cellulose-binding peptides, polymer-binding peptides (see U.S. Pat. App. Pub. Nos. 2007/0141629, 2007/0264720, 2008/0207872, 2007/0141628, and 2007/0261775), clay-binding peptides, and carbon nanotube binding peptides) for targeted delivery of at least one benefit agent (see U.S. patent application Ser. No. 10/935,642; U.S. patent application Ser. No. 11/074,473; and U.S. Pat. App. Pub. No. 2007/0249805).

The peptide of interest may be a single chain peptide ranging in size from about 14 to about 600 amino acids in length and lacks an immunoglobulin fold. The peptide of interest may range in size from 14 to 400 amino acids in length, 14 to 300 amino acids in length, or 14 to about 200 amino acids in length. The peptide of interest may be produced in an insoluble form within the *Escherichia* host cell, such as in the form of inclusion bodies. The peptide of interest may be produced and accumulated in the cytoplasm as inclusion bodies. The peptide of interest may be a fusion peptide. The fusion peptide may be comprised of at least one solubility tag, such as an inclusion body tag.

Single Chain Peptides Having Affinity for a Target Surface

Proteinaceous materials having strong affinity for a body surface can target delivery of one or more personal care benefit agents. Some of these materials comprise or derive from immunoglobulins or immunoglobulin fragments (antibodies, antibody fragments, $F_{ab}$, single-chain variable fragments (scFv), and Camilidae $V_{HH}$) having affinity for the target surface. Other such proteinaceous materials comprise non-immunoglobulin derived scaffold proteins Further, these materials for delivery of a personal care benefit agent can include a single chain, linear peptide.

The peptide of interest used in the fusion proteins described herein is or is part of a proteinaceous material that has at least one domain having strong affinity for a target surface but does not comprise an immunoglobulin fold or underlying scaffold support. Thus, the POI preferably comprise at least one single chain peptide. Moreover, the peptide of interest described herein is heterologous to the *Escherichia* host cell and may be produced in the cytoplasm and not targeted for secretion and/or accumulation in the periplasm.

Single-chain peptides that target surfaces can be identified and isolated from peptide libraries using any number of biopanning techniques well known to those skilled in the art including, but not limited to bacterial display, yeast display, combinatorial solid phase peptide synthesis, phage display, ribosome display, and mRNA display. Techniques to generate random peptide libraries are described in Dani, M., *J. of Receptor & Signal Transduction Res.*, 21 (4):447-468 (2001). Phage display libraries are available commercially from companies such as New England BioLabs (Beverly, Mass.).

The peptide of interest may be a peptide-based reagent comprising a plurality of biopanned target surface-binding peptides coupled together (optionally through one or more spacers) to form at least one target surface binding domain. The peptide of interest may comprise multiple target surface-binding domains, wherein each domain may have affinity for the same or a different target surface The individual biopanned target surface-binding peptides are typically about 7 to about 60 amino acids in length and often have a binding affinity (as measured or reported as an $MB_{50}$ or $K_D$ value) of $10^{-5}$ M or less for the surface of the target material. The individual biopanned target surface-binding peptides may be from about 7 amino acids to about 60 amino acids in length, more preferably, from about 7 amino acids to about 25 amino acids in length, most preferably from about 7 to about 20 amino acids in length. The peptide of interest may also be a an individual target surface-binding peptide.

Examples of single chain peptide-based reagents having affinity for at least one target surface include, but are not limited to body surfaces such as hair, skin, nail, and teeth (U.S. Pat. Nos. 7,220,405; 7,309,482; and 7,285,264; U.S. Pat. App. Pub. Nos. 2005/0226839; 2007/0196305; 2006/0199206; 2007/0065387; 2008/0107614; 2007/0110686; and 2006/0073111; and Int'l Pat. App. Pub. Nos. WO2008/054746; WO2004/048399, and WO2008/073368) as well as other surfaces such as pigments and miscellaneous print media (U.S. Pat. App. Pub. No. 2005/0054752), and various polymers such as polymethylmethacrylate (U.S. Pat. App. Pub. No. 2007/0265431), polypropylene (U.S. Pat. App. Pub. No. 2007/0264720), nylon (U.S. Pat. App. Pub. Nos. 2007/0141629 and 2003/0185870), polytetrafluoroethylene (U.S. patent application Ser. No. 11/607,734), polyethylene (U.S. Pat. App. Pub. No. 2007/0141628), and polystyrene (U.S. Pat. App. Pub. No. 2007/0261775). Examples of various target surface-binding peptides are provided in Table A.

The target surface-binding peptide may have strong affinity for a particulate benefit agent surface (such as a pigment, a sunscreen agent, a whitening agent, etc.), a polymeric coating applied to a particulate benefit agent (such as a coated pigment), a clay, calcium carbonate or a body surface. Examples of various target-binding peptides are given in Table A.

Body Surface-Binding Peptides

The target surface-binding peptide may be a body surface-binding peptide. Peptides having an affinity for a body surface have been described in (U.S. Pat. Nos. 7,220,405 and 7,285,264; U.S. Pat. App. Pub. Nos. 2005/0226839, 2005/0249682, 2007/0065387, 2007/0067924, 2007/0196305, 2007/0110686, 2006/0073111, and 2006/0199206; U.S. patent application Ser. Nos. 11/877,692 and 11/939,583; and Int'l. Pat. App. Pub. No. WO2004/048399). Specific examples of body surface-binding peptides are provided in Table A.

Table A

Examples of Target Surface-Binding Peptides

| Target Surface | Amino Acid Sequence | SEQ ID NO: | Reference |
|---|---|---|---|
| Hair | RVPNKTVTVDGA | 24 | U.S. 2005/0,226,839 U.S. Pat. No. 7,220,405 |
| Hair | DRHKSKYSSTKS | 25 | U.S. 2005/0,226,839 U.S. Pat. No. 7,220,405 |
| Hair | KNFPQQKEFPLS | 26 | U.S. 2005/0,226,839 U.S. Pat. No. 7,220,405 |
| Hair | QRNSPPAMSRRD | 27 | U.S. 2005/0,226,839 U.S. Pat. No. 7,220,405 |
| Hair | TRKPNMPHGQYL | 28 | U.S. 2005/0,226,839 U.S. Pat. No. 7,220,405 |
| Hair | KPPHLAKLPFTT | 29 | U.S. 2005/0,226,839 U.S. Pat. No. 7,220,405 |
| Hair | NKRPPTSHRIHA | 30 | U.S. 2005/0,226,839 U.S. Pat. No. 7,220,405 |
| Hair | NLPRYQPPCKPL | 31 | U.S. 2005/0,226,839 U.S. Pat. No. 7,220,405 |
| Hair | RPPWKKPIPPSE | 32 | U.S. 2005/0,226,839 U.S. Pat. No. 7,220,405 |
| Hair | RQRPKDHFFSRP | 33 | U.S. 2005/0,226,839 U.S. Pat. No. 7,220,405 |
| Hair | SVPNKXVTVDGX | 34 | U.S. 2005/0,226,839 U.S. Pat. No. 7,220,405 |
| Hair | TTKWRHRAPVSP | 35 | U.S. 2005/0,226,839 U.S. Pat. No. 7,220,405 |
| Hair | WLGKNRIKPRAS | 36 | U.S. 2005/0,226,839 U.S. Pat. No. 7,220,405 |
| Hair | SNFKTPLPLTQS | 37 | U.S. 2005/0,226,839 U.S. Pat. No. 7,220,405 |

Table A-continued

Examples of Target Surface-Binding Peptides

| Target Surface | Amino Acid Sequence | SEQ ID NO: | Reference |
|---|---|---|---|
| Hair | SVSVGMKPSPRP | 38 | U.S. 2005/0,226,839<br>U.S. Pat. No. 7,220,405 |
| Hair | DLHTVYH | 39 | U.S. 2005/0,226,839<br>U.S. Pat. No. 7,220,405 |
| Hair | HIKPPTR | 40 | U.S. 2005/0,226,839<br>U.S. Pat. No. 7,220,405 |
| Hair | HPVWPAI | 41 | U.S. 2005/0,226,839<br>U.S. Pat. No. 7,220,405 |
| Hair | MPLYYLQ | 42 | U.S. 2005/0,226,839<br>U.S. Pat. No. 7,220,405 |
| Hair | HLTVPWRGGGSAVPFYSHSQITLPNH | 43 | U.S. 2005/0,226,839<br>U.S. Pat. No. 7,220,405 |
| Hair | GPHDTSSGGVRPNLHHTSKKEKRENRKVPFYSHSVTSRGNV | 44 | U.S. 2005/0,226,839<br>U.S. Pat. No. 7,220,405 |
| Hair | KHPTYRQ | 45 | U.S. 2005/0,226,839<br>U.S. Pat. No. 7,220,405 |
| Hair | HPMSAPR | 46 | U.S. 2005/0,226,839<br>U.S. Pat. No. 7,220,405 |
| Hair | MPKYYLQ | 47 | U.S. 2005/0,226,839<br>U.S. Pat. No. 7,220,405 |
| Hair | MHAHSIA | 48 | U.S. 2005/0,226,839<br>U.S. Pat. No. 7,220,405 |
| Hair | AKPISQHLQRGS | 49 | U.S. 2005/0,226,839<br>U.S. Pat. No. 7,220,405 |
| Hair | APPTPAAASATT | 50 | U.S. 2005/0,226,839<br>U.S. Pat. No. 7,220,405 |
| Hair | DPTEGARRTIMT | 51 | U.S. 2005/0,226,839<br>U.S. Pat. No. 7,220,405 |
| Hair | LDTSFPPVPFHA | 52 | U.S. 2005/0,226,839<br>U.S. Pat. No. 7,220,405 |
| Hair | LDTSFHQVPFHQ | 53 | U.S. 2005/0,226,839<br>U.S. Pat. No. 7,220,405 |
| Hair | LPRIANTWSPS | 54 | U.S. 2005/0,226,839<br>U.S. Pat. No. 7,220,405 |
| Hair | RTNAADHPAAVT | 55 | U.S. 2005/0,226,839<br>U.S. Pat. No. 7,220,405<br>U.S. 2007/0,065,387 |
| Hair | SLNWVTIPGPKI | 56 | U.S. 2005/0,226,839<br>U.S. Pat. No. 7,220,405 |
| Hair | TDMQAPTKSYSN | 57 | U.S. 2005/0,226,839<br>U.S. Pat. No. 7,220,405 |
| Hair | TIMTKSPSLSCG | 58 | U.S. 2005/0,226,839<br>U.S. Pat. No. 7,220,405 |
| Hair | TPALDGLRQPLR | 59 | U.S. 2005/0,226,839<br>U.S. Pat. No. 7,220,405 |
| Hair | TYPASRLPLLAP | 60 | U.S. 2005/0,226,839<br>U.S. Pat. No. 7,220,405 |
| Hair | AKTHKHPAPSYS | 61 | U.S. 2005/0,226,839<br>U.S. Pat. No. 7,220,405 |
| Hair | TDPTPFSISPER | 62 | U.S. 2005/0,226,839<br>U.S. Pat. No. 7,220,405 |
| Hair | SQNWQDSTSYSN | 63 | U.S. 2005/0,226,839<br>U.S. Pat. No. 7,220,405 |
| Hair | WHDKPQNSSKST | 64 | U.S. 2005/0,226,839<br>U.S. Pat. No. 7,220,405 |
| Hair | LDVESYKGTSMP | 65 | U.S. 2005/0,226,839<br>U.S. Pat. No. 7,220,405 |
| Hair | NTPKENW | 66 | WO2004/48399 |
| Hair | NTPASNR | 67 | WO2004/48399 |
| Hair | PRGMLST | 68 | WO2004/48399 |
| Hair | PPTYLST | 69 | WO2004/48399 |
| Hair | TIPTHRQHDYRS | 70 | WO2004/48399 |
| Hair | TPPTHRL | 71 | WO2004/048399 |
| Hair | LPTMSTP | 72 | WO2004/048399 |
| Hair | LGTNSTP | 73 | WO2004/048399 |
| Hair | TPLTGSTNLLSS | 74 | WO2004/048399 |
| Hair | TPLTKET | 75 | WO2004/048399 |
| Hair | KQSHNPP | 76 | WO2004/048399 |
| Hair | QQSHNPP | 77 | WO2004/048399 |
| Hair | TQPHNPP | 78 | WO2004/048399 |
| Hair | STNLLRTSTVHP | 79 | WO2004/048399 |
| Hair | HTQPSYSSTNLF | 80 | WO2004/048399 |
| Hair | SLLSSHA | 81 | WO2004/048399 |
| Hair | QQSSISLSSHAV | 82 | WO2004/048399 |

Table A-continued

Examples of Target Surface-Binding Peptides

| Target Surface | Amino Acid Sequence | SEQ ID NO: | Reference |
|---|---|---|---|
| Hair | NASPSSL | 83 | WO2004/048399 |
| Hair | HSPSSLR | 84 | WO2004/048399 |
| Hair | K H/R/N SHHTH | 85 | WO2004/048399 |
| Hair | E H/R/N SHHTH | 86 | WO2004/048399 |
| Hair | SHHTHYGQPGPV | 87 | WO2004/048399 |
| Hair | LESTSLL | 88 | WO2004/048399 |
| Hair | DLTLPFH | 89 | U.S. 2007/065,387 |
| Hair | RTNAADHP | 90 | U.S. 2007/067,924 |
| Hair | IPWWNIRAPLNA | 91 | U.S. 2007/0,067,924 |
| Hair | EQISGSLVAAPWEGEGER | 92 | U.S. Ser. No. 11/877,692 |
| Hair | TPPELLHGAPRS | 93 | U.S. Ser. No. 11/877,692 |
| Hair | LDTSFHQVPFHQKRKRKD | 94 | U.S. Ser. No. 11/877,692 |
| Hair | EQISGSLVAAPWKRKRKD | 95 | U.S. Ser. No. 11/877,692 |
| Hair | TPPELLHGDPRSKRKRKD | 96 | U.S. Ser. No. 11/877,692 |
| Hair | NTSQLSTEGEGED | 97 | U.S. Ser. No. 11/877,692 |
| Hair | TPPELLHGDPRSC | 98 | U.S. 2007/067,924 |
| Hair "MEA4" | HINKTNPHQGNHHSEKTQRQ | 99 | U.S. Ser. No. 11/939,583 |
| Hair | HAHKNQKETHQRHAA | 100 | U.S. Ser. No. 11/939,583 |
| Hair | HEHKNQKETHQRHAA | 101 | U.S. Ser. No. 11/939,583 U.S. Pat. No. 7,285,264 |
| Hair | HNHMQERYTEPQHSPSVNGL | 102 | U.S. Ser. No. 11/939,583 |
| Hair | THSTHNHGSPRHTNADA | 103 | U.S. 2007/196,305 |
| Hair | GSCVDTHKADSCVANNGPAT | 104 | U.S. Ser. No. 11/939,583 |
| Hair "HP2" | AQSQLPDKHSGLHERAPQRY | 105 | U.S. Ser. No. 11/939,583 |
| Hair | AQSQLPAKHSGLHERAPQRY | 106 | U.S. Ser. No. 11/939,583 |
| Hair | AQSQLPEKHSGLHERAPQRY | 107 | U.S. Ser. No. 11/939,583 |
| Hair | TDMMHNHSDNSPPHRRSPRN | 108 | U.S. Ser. No. 11/939,583 |
| Hair | TPPELAHTPHHLAQTRLTDR | 109 | U.S. Ser. No. 11/939,583 |
| Hair | RLLRLLRLLRLL | 110 | U.S. Ser. No. 11/939,583 |
| Hair | TPPELLHGEPRS | 111 | U.S. Ser. No. 11/939,583 |
| Hair | TPPELLHGAPRS | 112 | U.S. Pat. No. 7,285,264 |
| Hair (normal and bleached) | EQISGSLVAAPW | 113 | U.S. 2005/0,226,839 U.S. Pat. No. 7,220,405 |
| Hair (bleached) | NEVPARNAPWLV | 114 | U.S. 2005/0,226,839 U.S. Pat. No. 7,220,405 |
| Hair (bleached) | NSPGYQADSVAIG | 115 | U.S. 2005/0,226,839 U.S. Pat. No. 7,220,405 |
| Hair (bleached) | AKPISQHLQRGS | 116 | U.S. 2005/0,226,839 U.S. Pat. No. 7,220,405 |
| Hair (bleached) | LDTSFPPVPFHA | 117 | U.S. 2005/0,226,839 U.S. Pat. No. 7,220,405 |
| Hair (bleached) | SLNWVTIPGPKI | 118 | U.S. 2005/0,226,839 U.S. Pat. No. 7,220,405 |
| Hair (bleached) | TQDSAQKSPSPL | 119 | U.S. 2005/0,226,839 U.S. Pat. No. 7,220,405 |
| Hair (bleached) | KELQTRNVVQRE | 120 | U.S. 2005/0,226,839 U.S. Pat. No. 7,220,405 |
| Hair (bleached) | QRNSPPAMSRRD | 121 | U.S. 2005/0,226,839 U.S. Pat. No. 7,220,405 |
| Hair (bleached) | TPTANQFTQSVP | 122 | U.S. 2005/0,226,839 U.S. Pat. No. 7,220,405 |
| Hair (bleached) | AAGLSQKHERNR | 123 | U.S. 2005/0,226,839 U.S. Pat. No. 7,220,405 |
| Hair (bleached) | ETVHQTPLSDRP | 124 | U.S. 2005/0,226,839 U.S. Pat. No. 7,220,405 |
| Hair (bleached) | KNFPQQKEFPLS | 125 | U.S. 2005/0,226,839 U.S. Pat. No. 7,220,405 |
| Hair (bleached) | LPALHIQRHPRM | 126 | U.S. 2005/0,226,839 U.S. Pat. No. 7,220,405 |
| Hair (bleached) | QPSHSQSHNLRS | 127 | U.S. 2005/0,226,839 U.S. Pat. No. 7,220,405 |
| Hair (bleached) | RGSQKSKPPRPP | 128 | U.S. 2005/0,226,839 U.S. Pat. No. 7,220,405 |
| Hair (bleached) | THTQKTPLLYYH | 129 | U.S. 2005/0,226,839 U.S. Pat. No. 7,220,405 |
| Hair (bleached) | TKGSSQAILKST | 130 | U.S. 2005/0,226,839 U.S. Pat. No. 7,220,405 |
| Hair (normal and bleached) | TAATTSP | 131 | U.S. 2005/0,226,839 U.S. Pat. No. 7,220,405 |

Table A-continued

Examples of Target Surface-Binding Peptides

| Target Surface | Amino Acid Sequence | SEQ ID NO: | Reference |
|---|---|---|---|
| Hair (bleached) | LGIPQNL | 132 | U.S. 2005/0,226,839<br>U.S. Pat. No. 7,220,405 |
| Hair (Conditioner resistant) | THSTHNHGSPRHTNADAGNP | 133 | U.S. 2007/0,065,387<br>U.S. 2007/0,196,305 |
| Hair (Conditioner resistant) | QQHKVHHQNPDRSTQDAHHS | 134 | U.S. 2007/0,196,305 |
| Hair (Conditioner resistant) | HHGTHHNATKQKNHV | 135 | U.S. 2007/0,196,305 |
| Hair (Conditioner resistant) | STLHKYKSQDPTPHH | 136 | U.S. 2007/0,196,305 |
| Hair (Conditioner resistant) | SVSVGMKPSPRP | 137 | U.S. 2007/0,196,305 |
| Hair (shampoo resistant) | TPPTNVLMLATK | 138 | U.S. 2006/0,073,111 |
| Hair (shampoo resistant) | TPPELLHGDPRS | 139 | U.S. 2006/0,073,111 |
| Hair (shampoo resistant) | NTSQLST | 140 | U.S. 2007/0,067,924<br>U.S. Pat. No. 7,285,264 |
| Hair (conditioner resistant) | STLHKYKSQDPTPHH | 141 | U.S. 2007/0,196,305 |
| Hair (shampoo and conditioner resistant) | GMPAMHWIHPFA | 142 | U.S. 2006/0,073,111<br>U.S. Pat. No. 7,285,264 |
| Hair (shampoo and conditioner resistant) | HDHKNQKETHQRHAA | 143 | U.S. 2006/0,073,111<br>U.S. Pat. No. 7,285,264 |
| Hair (shampoo and conditioner resistant) | HNHMQERYTDPQHSPSVNGL | 144 | U.S. 2006/0,073,111<br>U.S. Pat. No. 7,285,264 |
| Hair (shampoo and conditioner resistant) | TAEIQSSKNPNPHPQRSWTN | 145 | U.S. 2006/0,073,111<br>U.S. Pat. No. 7,285,264 |
| Hair (dyed) | SSADFASFGFFGFSAASADSR | 146 | U.S. Ser. No. 12/198,382 |
| Hair (dyed) | SSFAEAWSRAWPRAEVFFPSRGY | 147 | U.S. Ser. No. 12/198,382 |
| Hair (dyed) | SSFSVNEPHAWMAPLSR | 148 | U.S. Ser. No. 12/198,382 |
| Hair (dyed) | SSFSWVYGHGGLGFASR | 149 | U.S. Ser. No. 12/198,382 |
| Hair (dyed) | SSFVSWSPYKSPPELSR | 150 | U.S. Ser. No. 12/198,382 |
| Hair (dyed) | SSFYGSSAFVSSGVSVAYGSR | 151 | U.S. Ser. No. 12/198,382 |
| Hair (dyed) | SSGSVAVSAEASWFSGVAASR | 152 | U.S. Ser. No. 12/198,382 |
| Hair (dyed) | SSHDEHYQYHYYSSR | 153 | U.S. Ser. No. 12/198,382 |
| Hair (dyed) | SSHYYYNDYDHQSSR | 154 | U.S. Ser. No. 12/198,382 |
| Hair (dyed) | SSLFNMYGHQSVLGPSR | 155 | U.S. Ser. No. 12/198,382 |
| Hair (dyed) | SSLFSDVHYGSNKALSR | 156 | U.S. Ser. No. 12/198,382 |
| Hair (dyed) | SSLLSDFHYGDMWDASR | 157 | U.S. Ser. No. 12/198,382 |
| Hair (dyed) | SSNYNYNYQYSSR | 158 | U.S. Ser. No. 12/198,382 |
| Hair (dyed) | SSNYNYNYQYSSREGEGER | 159 | U.S. Ser. No. 12/198,382 |
| Hair (dyed) | SSNYNYNYQYSSRKRKRKD | 160 | U.S. Ser. No. 12/198,382 |
| Hair (dyed) | SSQYYQDYQYYHSSR | 161 | U.S. Ser. No. 12/198,382 |
| Hair (dyed) | SSSCMGSHNPRMSVEESTRNCSR | 162 | U.S. Ser. No. 12/198,382 |
| Hair (dyed) | SSSCNNNWFYSSTLPGGDHACSR | 163 | U.S. Ser. No. 12/198,382 |
| Hair (dyed) | SSSCYDVECSSFVAWMRGPSSSR | 164 | U.S. Ser. No. 12/198,382 |
| Hair (dyed) | SSSFAASSAFSFLVDAVAWSR | 165 | U.S. Ser. No. 12/198,382 |
| Hair (dyed) | SSSFAYLVPDDGWLSSR | 166 | U.S. Ser. No. 12/198,382 |
| Hair (dyed) | SSSGAVFSSGGADAGWGVWSR | 167 | U.S. Ser. No. 12/198,382 |
| Hair (dyed) | SSSSADAAYGHCCGAGFSTFSSR | 168 | U.S. Ser. No. 12/198,382 |
| Hair (dyed) | SSSSDVHNSIIGWDFYHSRGSSR | 169 | U.S. Ser. No. 12/198,382 |
| Hair (dyed) | SSSSLDFFSYSAFSGGVAESR | 170 | U.S. Ser. No. 12/198,382 |

Table A-continued

Examples of Target Surface-Binding Peptides

| Target Surface | Amino Acid Sequence | SEQ ID NO: | Reference |
|---|---|---|---|
| Hair (dyed) | SSSSNDSNVSWFHYYASGLTSSR | 171 | U.S. Ser. No. 12/198,382 |
| Hair (dyed) | SSVDYEVPLAVAAEWGFSVSR | 172 | U.S. Ser. No. 12/198,382 |
| Hair (dyed) | SSYHYDYDHYYESSR | 173 | U.S. Ser. No. 12/198,382 |
| Hair (dyed) | SSYYNYHYQYQDSSR | 174 | U.S. Ser. No. 12/198,382 |
| Hair (dyed) | SSYYYDYYQQDYSSR | 175 | U.S. Ser. No. 12/198,382 |
| Hair and skin (Empirical) | KRGRHKRPKRHK | 176 | U.S. 2007/0,065,387 U.S. 2007/0,110,686 U.S. 2007/0,067,924 |
| Hair and skin (Empirical) | RLLRLLR | 177 | U.S. 2007/0,065,387 U.S. 2007/0,110,686 |
| Hair and skin (Empirical) | HKPRGGRKKALH | 178 | U.S. 2007/0,065,387 U.S. 2007/0,110,686 |
| Hair and skin (Empirical) | KPRPPHGKKHRPKHRPKK | 179 | U.S. 2007/0,065,387 U.S. 2007/0,110,686 |
| Hair and skin (Empirical) | RGRPKKGHGKRPGHRARK | 180 | U.S. 2007/0,065,387 U.S. 2007/0,110,686 |
| Skin | TPFHSPENAPGS | 181 | U.S. Ser. No. 11/877,692 U.S. 2005/0,249,682 |
| Skin | TPFHSPENAPGSK | 182 | U.S. 2007/0,110,686 |
| Skin | TPFHSPENAPGSGGGS | 183 | U.S. 2007/0,110,686 |
| Skin | TPFHSPENAPGSGGGSS | 184 | U.S. 2007/0,110,686 |
| Skin | TPFHSPENAPGSGGG | 185 | U.S. 2007/0,110,686 |
| Skin | FTQSLPR | 186 | U.S. Ser. No. 11/877,692 U.S. 2005/0,249,682 |
| Skin | KQATFPPNPTAY | 187 | U.S. Ser. No. 11/877,692 U.S. 2005/0,249,682 WO2004/048399 |
| Skin | HGHMVSTSQLSI | 188 | U.S. Ser. No. 11/877,692 U.S. 2005/0,249,682 WO2004/048399 |
| Skin | LSPSRMK | 189 | U.S. Ser. No. 11/877,692 U.S. 2005/0,249,682 WO2004/048399 |
| Skin | LPIPRMK | 190 | U.S. 2005/0,249,682 WO2004/048399 |
| Skin | HQRPYLT | 191 | U.S. 2005/0,249,682 WO2004/048399 |
| Skin | FPPLLRL | 192 | U.S. 2005/0,249,682 WO2004/048399 |
| Skin | QATFMYN | 193 | WO2004/048399 |
| Skin | VLTSQLPNHSM | 194 | WO2004/048399 |
| Skin | HSTAYLT | 195 | WO2004/048399 |
| Skin | APQQRPMKTFNT | 196 | WO2004/048399 |
| Skin | APQQRPMKTVQY | 197 | WO2004/048399 |
| Skin | PPWLDLL | 198 | WO2004/048399 |
| Skin | PPWTFPL | 199 | WO2004/048399 |
| Skin | SVTHLTS | 200 | WO2004/048399 |
| Skin | VITRLTS | 201 | WO2004/048399 |
| Skin | DLKPPLLALSKV | 202 | WO2004/048399 |
| Skin | SHPSGALQEGTF | 203 | WO2004/048399 |
| Skin | FPLTSKPSGACT | 204 | WO2004/048399 |
| Skin | DLKPPLLALSKV | 205 | WO2004/048399 |
| Skin | PLLALHS | 206 | WO2004/048399 |
| Skin | VPISTQI | 207 | WO2004/048399 |
| Skin | YAKQHYPISTFK | 208 | WO2004/048399 |
| Skin | HSTAYLT | 209 | WO2004/048399 |
| Skin | STAYLVAMSAAP | 210 | WO2004/048399 |
| Skin (Body Wash Resistant) | SVSVGMKPSPRP | 211 | U.S. Ser. No. 11/877,692 U.S. 2006/0,199,206 |
| Skin (Body Wash Resistant) | TMGFTAPRFPHY | 212 | U.S. Ser. No. 11/877,692 U.S. 2006/0,199,206 |
| Skin (Body Wash Resistant) | NLQHSVGTSPVW | 213 | U.S. Ser. No. 11/877,692 U.S. 2006/0,199,206 |
| Skin (Body Wash Resistant) | QLSYHAYPQANHHAP | 214 | U.S. Ser. No. 11/877,692 U.S. 2006/0,199,206 |

Table A-continued

Examples of Target Surface-Binding Peptides

| Target Surface | Amino Acid Sequence | SEQ ID NO: | Reference |
|---|---|---|---|
| Skin (Body Wash Resistant) | NQAASITKRVPY | 215 | U.S. 2006/0,199,206 |
| Skin (Body Wash Resistant) | SGCHLVYDNGFCDH | 216 | U.S. Ser. No. 11/877,692 U.S. 2006/0,199,206 |
| Skin (Body Wash Resistant) | ASCPSASHADPCAH | 217 | U.S. Ser. No. 11/877,692 U.S. 2006/0,199,206 |
| Skin (Body Wash Resistant) | NLCDSARDSPRCKV | 218 | U.S. Ser. No. 11/877,692 U.S. 2006/0,199,206 |
| Skin (Body Wash Resistant) | NHSNWKTAADFL | 219 | U.S. Ser. No. 11/877,692 U.S. 2006/0,199,206 |
| Skin (Body Wash Resistant) | GSSTVGRPLSYE | 220 | U.S. 2006/0,199,206 |
| Skin (Body Wash Resistant) | SDTISRLHVSMT | 221 | U.S. Ser. No. 11/877,692 U.S. 2006/0,199,206 |
| Skin (Body Wash Resistant) | SPLTVPYERKLL | 222 | U.S. 2006/0,199,206 |
| Skin (Body Wash Resistant) | SPYPSWSTPAGR | 223 | U.S. Ser. No. 11/877,692 U.S. 2006/0,199,206 |
| Skin (Body Wash Resistant) | VQPITNTRYEGG | 224 | U.S. 2006/0,199,206 |
| Skin (Body Wash Resistant) | WPMHPEKGSRWS | 225 | U.S. 2006/0,199,206 |
| Skin (Body Wash Resistant) | DACSGNGHPNNCDR | 226 | U.S. Ser. No. 11/877,692 U.S. 2006/0,199,206 |
| Skin (Body Wash Resistant) | DHCLGRQLQPVCYP | 227 | U.S. 2006/0,199,206 |
| Skin (Body Wash Resistant) | DWCDTIIPGRTCHG | 228 | U.S. Ser. No. 11/877,692 U.S. 2006/0,199,206 |
| Fingernail | ALPRIANTWSPS | 229 | U.S. 2005/0,226,839 U.S. Pat. No. 7,220,405 |
| Fingernail and Hair | YPSFSPTYRPAF | 230 | U.S. 2005/0,226,839 U.S. Pat. No. 7,220,405 |
| Tooth (pellicle) | AHPESLGIKYALDGNSDPHA | 231 | U.S. Ser. No. 11/877,692 |
| Tooth (pellicle) | ASVSNYPPIHHLATSNTTVN | 232 | U.S. Ser. No. 11/877,692 |
| Tooth (pellicle) | DECMEPLNAAHCWR | 233 | U.S. Ser. No. 11/877,692 |
| Tooth (pellicle) | DECMHGSDVEFCTS | 234 | U.S. Ser. No. 11/877,692 |
| Tooth (pellicle) | DLCSMQMMNTGCHY | 235 | U.S. Ser. No. 11/877,692 |
| Tooth (pellicle) | DLCSSPSTWGSCIR | 236 | U.S. Ser. No. 11/877,692 |
| Tooth (pellicle) | DPNESNYENATTVSQPTRHL | 237 | U.S. Ser. No. 11/877,692 |
| Tooth (pellicle) | EPTHPTMRAQMHQSLRSSSP | 238 | U.S. Ser. No. 11/877,692 |
| Tooth (pellicle) | GNTDTTPPNAVMEPTVQHKW | 239 | U.S. Ser. No. 11/877,692 |
| Tooth (pellicle) | NGPDMVQSVGKHKNS | 240 | U.S. Ser. No. 11/877,692 |
| Tooth (pellicle) | NGPEVRQIPANFEKL | 241 | U.S. Ser. No. 11/877,692 |
| Tooth (pellicle) | NNTSADNPPETDSKHHLSMS | 242 | U.S. Ser. No. 11/877,692 |
| Tooth (pellicle) | NNTWPEGAGHTMPSTNIRQA | 243 | U.S. Ser. No. 11/877,692 |
| Tooth (pellicle) | NPTATPHMKDPMHSNAHSSA | 244 | U.S. Ser. No. 11/877,692 |

TABLE A-continued

Examples of Target Surface-Binding Peptides

| Target Surface | Amino Acid Sequence | SEQ ID NO: | Reference |
|---|---|---|---|
| Tooth (pellicle) | NPTDHIPANSTNSRVSKGNT | 245 | U.S. Ser. No. 11/877,692 |
| Tooth (pellicle) | NPTDSTHMMHARNHE | 246 | U.S. Ser. No. 11/877,692 |
| Tooth (pellicle) | QHCITERLHPPCTK | 247 | U.S. Ser. No. 11/877,692 |
| Tooth (pellicle) | TPCAPASFNPHCSR | 248 | U.S. Ser. No. 11/877,692 |
| Tooth (pellicle) | TPCATYPHFSGCRA | 249 | U.S. Ser. No. 11/877,692 |
| Tooth (pellicle) | WCTDFCTRSTPTSTSRSTTS | 250 | U.S. Ser. No. 11/877,692 |
| Tooth (enamel) | APPLKTYMQERELTMSQNKD | 251 | U.S. Ser. No. 11/877,692 |
| Tooth (enamel) | EPPTRTRVNNHTVTVQAQQH | 252 | U.S. Ser. No. 11/877,692 |
| Tooth (enamel) | GYCLRGDEPAVCSG | 253 | U.S. Ser. No. 11/877,692 |
| Tooth (enamel) | LSSKDFGVTNTDQRTYDYTT | 254 | U.S. Ser. No. 11/877,692 |
| Tooth (enamel) | NFCETQLDLSVCTV | 255 | U.S. Ser. No. 11/877,692 |
| Tooth (enamel) | NTCQPTKNATPCSA | 256 | U.S. Ser. No. 11/877,692 |
| Tooth (enamel) | PSEPERRDRNIAANAGRFNT | 257 | U.S. Ser. No. 11/877,692 |
| Tooth (enamel) | THNMSHFPPSGHPKRTAT | 258 | U.S. Ser. No. 11/877,692 |
| Tooth (enamel) | TTCPTMGTYHVCWL | 259 | U.S. Ser. No. 11/877,692 |
| Tooth (enamel) | YCADHTPDPANPNKICGYSH | 260 | U.S. Ser. No. 11/877,692 |
| Tooth (enamel) | AANPHTEWDRDAFQLAMPPK | 261 | U.S. Ser. No. 11/877,692 |
| Tooth (enamel) | DLHPMDPSNKRPDNPSDLHT | 262 | U.S. Ser. No. 11/877,692 |
| Tooth (enamel) | ESCVSNALMNQCIY | 263 | U.S. Ser. No. 11/877,692 |
| Tooth (enamel) | HNKADSWDPDLPPHAGMSLG | 264 | U.S. Ser. No. 11/877,692 |
| Tooth (enamel) | LNDQRKPGPPTMPTHSPAVG | 265 | U.S. Ser. No. 11/877,692 |
| Tooth (enamel) | NTCATSPNSYTCSN | 266 | U.S. Ser. No. 11/877,692 |
| Tooth (enamel) | SDCTAGLVPPLCAT | 267 | U.S. Ser. No. 11/877,692 |
| Tooth (enamel) | TIESSQHSRTHQQNYGSTKT | 268 | U.S. Ser. No. 11/877,692 |
| Tooth (enamel) | VGTMKQHPTTTQPPRVSATN | 269 | U.S. Ser. No. 11/877,692 |
| Tooth (enamel) | YSETPNDQKPNPHYKVSGTK | 270 | U.S. Ser. No. 11/877,692 |
| PMMA | IPWWNIRAPLNA | 271 | U.S. 2007/0,265,431 |
| PMMA | TAVMNVVNNQLS | 272 | U.S. 2007/0,265,431 |
| PMMA | VPWWAPSKLSMQ | 273 | U.S. 2007/0,265,431 |
| PMMA | MVMAPHTPRARS | 274 | U.S. 2007/0,265,431 |
| PMMA | TYPNWAHLLSHY | 275 | U.S. 2007/0,265,431 |
| PMMA | TPWWRIT | 276 | U.S. 2007/0,265,431 |
| PMMA | DLTLPFH | 277 | U.S. 2007/0,265,431 |
| PMMA | GTSIPAM | 278 | U.S. 2007/0,265,431 |
| PMMA | HHKHVVA | 279 | U.S. 2007/0,265,431 |
| PMMA | HHHKHFM | 280 | U.S. 2007/0,265,431 |
| PMMA | HHHRHQG | 281 | U.S. 2007/0,265,431 |
| PMMA | HHWHAPR | 282 | U.S. 2007/0,265,431 |
| PMMA | APWHLSSQYSGT | 283 | U.S. 2007/0,065,387 |
| PMMA | GYCLRVDEPTVCSG | 284 | U.S. 2007/0,065,387 |
| PMMA | HIHPSDNFPHKNRTH | 285 | U.S. 2007/0,065,387 |
| PMMA | HTHHDTHKPWPTDDHRNSSV | 286 | U.S. 2007/0,065,387 |
| PMMA | PEDRPSRTNALHHNAHHHNA | 287 | U.S. 2007/0,065,387 |
| PMMA | TPHNHATTNHHAGKK | 288 | U.S. 2007/0,065,387 |
| PMMA | EMVKDSNQRNTRISS | 289 | U.S. 2007/0,065,387 |
| PMMA | HYSRYNPGPHPL | 290 | U.S. 2007/0,065,387 |
| PMMA | IDTFYMSTMSHS | 291 | U.S. 2007/0,065,387 |
| PMMA | PMKEATHPVPPHKHSETPTA | 292 | U.S. 2007/0,065,387 |

Table A-continued

Examples of Target Surface-Binding Peptides

| Target Surface | Amino Acid Sequence | SEQ ID NO: | Reference |
|---|---|---|---|
| PMMA | YQTSSPAKQSVG | 293 | U.S. 2007/0,065,387 |
| PMMA | HLPSYQITQTHAQYR | 294 | U.S. 2007/0,065,387 |
| PMMA | TTPKTTYHQSRAPVTAMSEV | 295 | U.S. 2007/0,065,387 |
| PMMA | DRIHHKSHHVTTNHF | 296 | U.S. 2007/0,065,387 |
| PMMA | WAPEKDYMQLMK | 297 | U.S. 2007/0,065,387 |
| PP | TSDIKSRSPHHR | 298 | U.S. 2007/0,264,720 |
| PP | HTQNMRMYEPWF | 299 | U.S. 2007/0,264,720 |
| PP | LPPGSLA | 300 | U.S. 2007/0,264,720 |
| PP | MPAVMSSAQVPR | 301 | U.S. 2007/0,264,720 |
| PP | NQSFLPLDFPFR | 302 | U.S. 2007/0,264,720 |
| PP | SILSTMSPHGAT | 303 | U.S. 2007/0,264,720 |
| PP | SMKYSHSTAPAL | 304 | U.S. 2007/0,264,720 |
| PTFE | ESSYSWSPARLS | 305 | U.S. Ser. No. 11/607,734 |
| PTFE | GPLKLLHAWWQP | 306 | U.S. Ser. No. 11/607,734 |
| PTFE | NALTRPV | 307 | U.S. Ser. No. 11/607,734 |
| PTFE | SAPSSKN | 308 | U.S. Ser. No. 11/607,734 |
| PTFE | SVSVGMKPSPRP | 309 | U.S. Ser. No. 11/607,734 |
| PTFE | SYYSLPPIFHIP | 310 | U.S. Ser. No. 11/607,734 |
| PTFE | TFTPYSITHALL | 311 | U.S. Ser. No. 11/607,734 |
| PTFE | TMGFTAPRFPHY | 312 | U.S. Ser. No. 11/607,734 |
| PTFE | TNPFPPPPSSPA | 313 | U.S. Ser. No. 11/607,734 |
| PE | HNKSSPLTAALP | 314 | U.S. 2007/0,141,628 |
| PE | LPPWKHKTSGVA | 315 | U.S. 2007/0,141,628 |
| PE | LPWWLRDSYLLP | 316 | U.S. 2007/0,141,628 |
| PE | VPWWKHPPLPVP | 317 | U.S. 2007/0,141,628 |
| PE | HHKQWHNHPHHA | 318 | U.S. 2007/0,141,628 |
| PE | HIFSSWHQMWHR | 319 | U.S. 2007/0,141,628 |
| PE | WPAWKTHPILRM | 320 | U.S. 2007/0,141,628 |
| Nylon | KTPPTRP | 321 | U.S. 2007/0,141,629 |
| Nylon | VINPNLD | 322 | U.S. 2007/0,141,629 |
| Nylon | KVWIVST | 323 | U.S. 2007/0,141,629 |
| Nylon | AEPVAML | 324 | U.S. 2007/0,141,629 |
| Nylon | AELVAML | 325 | U.S. 2007/0,141,629 |
| Nylon | HSLRLDW | 326 | U.S. 2007/0,141,629 |
| PS | TSTASPTMQSKIR | 327 | U.S. 2007/0,261,775 |
| PS | KRNHWQRMHLSA | 328 | U.S. 2007/0,261,775 |
| PS | SHATPPQGLGPQ | 329 | U.S. 2007/0,261,775 |
| CA | ATTPPSGKAAAHSAARQKGN | 330 | U.S. 61/016,708 |
| CA | DTIHPNKMKSPSSPL | 331 | U.S. 61/016,708 |
| CA | NGNNHTDIPNRSSYTGGSFA | 332 | U.S. 61/016,708 |
| CA | SDETGPQIPHRRPTW | 333 | U.S. 61/016,708 |
| Carbon black | MPPPLMQ | 334 | U.S. 2005/0,054,752 |
| Carbon black | FHENWPS | 335 | U.S. 2005/0,054,752 |
| Carbon black | RTAPTTPLLLSL | 336 | U.S. 2005/0,054,752 |
| Carbon black | WHLSWSPVPLPT | 337 | U.S. 2005/0,054,752 |
| Cromophtal yellow | PHARLVG | 338 | U.S. 2005/0,054,752 |
| Cromophtal yellow | NIPYHHP | 339 | U.S. 2005/0,054,752 |
| Cromophtal yellow | TTMPAIP | 340 | U.S. 2005/0,054,752 |
| Cromophtal yellow | HNLPPRS | 341 | U.S. 2005/0,054,752 |
| Cromophtal yellow | AHKTQMGVRQPA | 342 | U.S. 2005/0,054,752 |
| Cromophtal yellow | ADNVQMGVSHTP | 343 | U.S. 2005/0,054,752 |
| Cromophtal yellow | AHNAQMGVSHPP | 344 | U.S. 2005/0,054,752 |
| Cromophtal yellow | ADYVGMGVSHRP | 345 | U.S. 2005/0,054,752 |
| Cromophtal yellow | SVSVGMKPSPRP | 346 | U.S. 2005/0,054,752 |
| Sunfast Magenta | YPNTALV | 347 | U.S. 2005/0,054,752 |
| Sunfast Magenta | VATRIVS | 348 | U.S. 2005/0,054,752 |
| Sunfast Magenta | HSLKNSMLTVMA | 349 | U.S. 2005/0,054,752 |

Table A-continued

Examples of Target Surface-Binding Peptides

| Target Surface | Amino Acid Sequence | SEQ ID NO: | Reference |
|---|---|---|---|
| Sunfast Blue | NYPTQAP | 350 | U.S. 2005/0,054,752 |
| Sunfast Blue | KCCYSVG | 351 | U.S. 2005/0,054,752 |
| Sunfast Blue | RHDLNTWLPPVK | 352 | U.S. 2005/0,054,752 |
| Sunfast Blue | EISLPAKLPSAS | 353 | U.S. 2005/0,054,752 |
| Sunfast Blue | SVSVGMKPSPRP | 346 | U.S. 2005/0,054,752 |
| Sunfast Blue | SDYVGMRPSPRH | 354 | U.S. 2005/0,054,752 |
| Sunfast Blue | SDYVGMRLSPSQ | 355 | U.S. 2005/0,054,752 |
| Sunfast Blue | SVSVGIQPSPRP | 356 | U.S. 2005/0,054,752 |
| Sunfast Blue | YVSVGIKPSPRP | 357 | U.S. 2005/0,054,752 |
| Sunfast Blue | YVCEGIHPCPRP | 358 | U.S. 2005/0,054,752 |
| Iron Oxide | WAPEKDHMQLMK | 359 | U.S. 61/138,623 |
| Iron Oxide | WAPEKDYMQLMK | 360 | U.S. 61/138,623 |
| Iron Oxide | CPLDTPTHKTKHEYKTRCRH | 361 | U.S. 61/138,623 |
| Iron Oxide | DHDHPRLHKRQEKSEHLH | 362 | U.S. 61/138,623 |
| Iron Oxide "Rfe5" | DSHHNHHKQDSRPQHRKTPN | 363 | U.S. 61/138,623 |
| Iron Oxide | EGGNAPHHKPHHRKH | 364 | U.S. 61/138,623 |
| Iron Oxide | HDSHRPLTQHGHRHSHVP | 365 | U.S. 61/138,623 |
| Iron Oxide | HDSNHCSHSTRRPNCART | 366 | U.S. 61/138,623 |
| Iron Oxide | ATRVDNTPASNPPSL | 367 | U.S. 61/138,623 |
| Iron Oxide | DGIKPFHLMTPTLAN | 368 | U.S. 61/138,623 |
| Iron Oxide | DITPPGSTHHRKPHRHQH | 369 | U.S. 61/138,623 |
| Iron Oxide | DNLWPQPLNVEDDRY | 370 | U.S. 61/138,623 |
| Iron Oxide | ENEKHRHNTHEALHSHFK | 371 | U.S. 61/138,623 |
| Iron Oxide | GAIWPASSALMTEHNPTDNH | 372 | U.S. 61/138,623 |
| Iron Oxide | GDTNQDTVMWYYTVN | 373 | U.S. 61/138,623 |
| Iron Oxide | HNGPYGMLSTGKIHF | 374 | U.S. 61/138,623 |
| Iron Oxide | LDGGYRDTPDNYLKG | 375 | U.S. 61/138,623 |
| Iron Oxide | LHTKTENSHTNMKTT | 376 | U.S. 61/138,623 |
| Iron Oxide | NAQYDPPTLNKGAVRKAAST | 377 | U.S. 61/138,623 |
| Iron Oxide | NGNNHTDIPNRSSYT | 378 | U.S. 61/138,623 |
| Iron Oxide | QSTNHHHPHAKHPRVNTH | 379 | U.S. 61/138,623 |
| Iron Oxide | SNNDYVGTYPATAIQ | 380 | U.S. 61/138,623 |
| Iron Oxide | STQHNLHDRNIYFVS | 381 | U.S. 61/138,623 |
| Iron Oxide | TANNKTPAGAPNAAVGLAQR | 382 | U.S. 61/138,623 |
| Iron Oxide | TEPTRISNYRSIPND | 383 | U.S. 61/138,623 |
| Iron Oxide | THNPREHARHHHHNEYKH | 384 | U.S. 61/138,623 |
| Iron Oxide | THPPCWYETNCIVQE | 385 | U.S. 61/138,623 |
| Iron Oxide | TTNPHKPASHHHDHRPALRH | 386 | U.S. 61/138,623 |
| Iron Oxide | WLVADNATDGHSHQK | 387 | U.S. 61/138,623 |
| Iron Oxide | YTDSMSDQTPEFAKY | 388 | U.S. 61/138,623 |
| Cotton Fabric | SILPYPY | 389 | U.S. 2005/0,054,752 |
| Cotton Fabric | STASYTR | 390 | U.S. 2005/0,054,752 |
| Polyester/ cotton blend | LPVRPWT | 391 | U.S. 2005/0,054,752 |
| Polyester/ cotton blend | SILPYPY | 389 | U.S. 2005/0,054,752 |
| Hammermill paper | GNTPSRA | 392 | U.S. 2005/0,054,752 |
| Hammermill paper | HAIYPRH | 393 | U.S. 2005/0,054,752 |
| Hammermill paper | YQDSAKT | 394 | U.S. 2005/0,054,752 |
| Hammermill paper | SILPYPY | 389 | U.S. 2005/0,054,752 |
| Cellulose | VPRVTSI | 395 | U.S. 2005/0,054,752 |
| Cellulose | MANHNLS | 396 | U.S. 2005/0,054,752 |
| Cellulose | FHENWPS | 397 | U.S. 2005/0,054,752 |
| Cellulose | THKTSTQRLLAA | 398 | U.S. 2005/0,054,752 |
| Cellulose | KCCYVNVGSVFS | 399 | U.S. 2005/0,054,752 |
| Cellulose | AHMQFRTSLTPH | 400 | U.S. 2005/0,054,752 |

Table A-continued

Examples of Target Surface-Binding Peptides

| Target Surface | Amino Acid Sequence | SEQ ID NO: | Reference |
|---|---|---|---|
| Clay | GHGSPSNSHHGSKKCDMGNSRAKCKRL | 401 | U.S. 2007/0,249,805 |
| Clay | SDRHNLRNSWSISRHCRRKQGRCLPAH | 402 | U.S. 2007/0,249,805 |
| Clay | KKSNKGHHPSSKGKGPPWSEWDKKNGP | 403 | U.S. 2007/0,249,805 |
| Clay | KKSNKGPHPSSKGKGPPWSEWDKKNGP | 404 | U.S. 2007/0,249,805 |
| Clay | VGRHHSKAKQKRPHGGKGQNKN | 405 | U.S. 2007/0,249,805 |
| Clay | VGRHHPKAKQKRPHGGKGQNKN | 406 | U.S. 2007/0,249,805 |
| Clay | GRRPRARGRSRRGSTKT | 407 | U.S. 2007/0,249,805 |
| Clay | LGVIRNHVVRGRRHHQHVR | 408 | U.S. 2007/0,249,805 |
| Clay | QPGRPTEVHPELVRKSAYLVNPSEDIR | 409 | U.S. 2007/0,249,805 |
| Clay | HRSEKPKNVKYKRGYWERGNQKKHGPG | 410 | U.S. 2007/0,249,805 |
| Clay | GSHKRRGSYALLRTRGVGRQAELEHLL | 411 | U.S. 2007/0,249,805 |
| Clay | VGEKPRRKSKGAKAKKARTKEEKLPKN | 412 | U.S. 2007/0,249,805 |
| Clay | NKGHKQSGSPRHSNKKEKKTQQKRGQP | 413 | U.S. 2007/0,249,805 |
| Clay | HWGSQHKTGLRNHKRSRRDSLGKRGTD | 414 | U.S. 2007/0,249,805 |
| Clay | KGWGSSSGPPGLTGKALGKGRLKPKKK | 415 | U.S. 2007/0,249,805 |
| Calcium carbonate | RNNKGSKKVDDKRRKTVHNTKSRAKYS | 416 | U.S. Ser. No. 11/828,539 |
| Calcium carbonate | RNNKGSKKVDDKRRKTVHNTKSRAKHS | 417 | U.S. Ser. No. 11/828,539 |
| Calcium carbonate | RDNKGSKKVDDKRRKTVHNTKSRAKYS | 418 | U.S. Ser. No. 11/828,539 |
| Calcium carbonate | RNNKGSKKVDDKRRKTVHSTKSRAKYS | 419 | U.S. Ser. No. 11/828,539 |
| Calcium carbonate | RNNKGSRKVDDKRRKTVHNTKSRAKYS | 420 | U.S. Ser. No. 11/828,539 |
| Calcium carbonate | RNNKGSKKADDKRRKTVHSTKSRAKYS | 421 | U.S. Ser. No. 11/828,539 |
| Calcium carbonate | RNNKGSKKVDDKRRKAVHNKKSRAKYS | 422 | U.S. Ser. No. 11/828,539 |
| Calcium carbonate | RNNKGSKKVDDKRRKTVHNTRSRAKYS | 423 | U.S. Ser. No. 11/828,539 |
| Calcium carbonate | RNNKGSKKVDDKRRKTVHNTKSRAKFS | 424 | U.S. Ser. No. 11/828,539 |
| Calcium carbonate | QRRKLRHPKEKWFGWSEKKVIKKWSRK | 425 | U.S. Ser. No. 11/828,539 |
| Calcium carbonate | QRRKFRHPKEKWFGWSEKKVIKXNGRP | 426 | U.S. Ser. No. 11/828,539 |
| Calcium carbonate | HKRLVQNKPHRTRKIEGWIKHMVKRQH | 427 | U.S. Ser. No. 11/828,539 |
| Calcium carbonate | TRGHIMRPCWIGAMKQGVKKKRTPGWR | 428 | U.S. Ser. No. 11/828,539 |
| Calcium carbonate | WKVKRRMVTRTYEFMGKKPCMMLTKRL | 429 | U.S. Ser. No. 11/828,539 |
| Calcium carbonate | KKSNKGHHSKAKQKRPHGGKAQNKNT | 430 | U.S. Ser. No. 11/828,539 |
| Calcium carbonate | RAHKERFVVRQIGRSQGYKTWQCVRVA | 431 | U.S. Ser. No. 11/828,539 |
| Calcium carbonate | SQKPKGHKVKVVVKLCKRPYWRMLNTA | 432 | U.S. Ser. No. 11/828,539 |
| Calcium carbonate | NHGCPVNWKVXNPPRGWQRLNHCKWWN | 433 | U.S. Ser. No. 11/828,539 |
| Calcium carbonate | RNSRHKEWRRYKRTHVHSHEFYHVECW | 434 | U.S. Ser. No. 11/828,539 |
| Calcium carbonate | HRSEKPKNVNYKRGYWERGNQKKHGPG | 435 | U.S. Ser. No. 11/828,539 |
| Calcium carbonate | HERTRRGKPDRQKTTHEKRRQGLWIFM | 436 | U.S. Ser. No. 11/828,539 |
| Calcium carbonate | PWGTNKRQKHKVHEAKALKKSLWYSNS | 437 | U.S. Ser. No. 11/828,539 |
| Calcium carbonate | RRGVVLCHTHRNKRIRLAYSVTKKAWA | 438 | U.S. Ser. No. 11/828,539 |
| Calcium carbonate | ERIRWRRLSAEIRAHKWSVLKFRLSCM | 439 | U.S. Ser. No. 11/828,539 |
| Calcium carbonate | KTKEKKKEVKLHKKSLSLVLLADLWRL | 440 | U.S. Ser. No. 11/828,539 |
| Calcium carbonate | LGKKHKQHSKVGHGKLSTRFLRRSKLF | 441 | U.S. Ser. No. 11/828,539 |

*PMMA means polymethylmethacrylate, PP means polypropylene, PTFE means polytetrafluoroethylene, PE means polyethylene, PS means polystyrene, CA means cellulose acetate.

The body surface-binding peptide may be selected from the group consisting of hair-binding peptides, skin-binding peptides, nail-binding peptides, and tooth-binding peptides, including both tooth enamel- and tooth pellicle-binding peptides. The body surface-binding peptide may be selected from the group consisting of hair-binding peptides (SEQ ID NOs: 24-180), skin-binding peptides (SEQ ID NOs. 176-228), nail-binding peptides (SEQ ID NOs. 229-230), and tooth-binding peptides (SEQ ID NOs. 231-270).

Production of Fusion Peptides Comprising an Inclusion Body Tag

The peptide of interest may be a small peptide that is appreciably soluble in the host cell and/or subject to endogenous proteolytic degradation. As such, the peptide of interest may be produced in an insoluble form (such as inclusion bodies) by fusing the peptide of interest to an inclusion body tag (see U.S. patent application Ser. Nos. 11/782,836, 11/641,273, 11/641,936, 12/172,395, 11/641,981, and U.S. Pat. No. 7,427,656; each incorporated herein by reference).

The desired gene product may be a small bioactive peptide of interest that is appreciably soluble in the host cell and/or host cell liquid lysate under normal physiological conditions. Fusion of the peptide of interest to at least one inclusion body forming tags creates a fusion peptide that is insoluble in the host cell and/or host cell lysate under normal physiological conditions. Production of the peptide of interest is typically increased when expressed and accumulated in the form of an insoluble inclusion body as the peptide is generally more protected from proteolytic degradation. Furthermore, the insoluble fusion protein can be easily separated from the host cell lysate using centrifugation or filtration.

Typically, the fusion peptide is insoluble in an aqueous matrix at a temperature of 10° C. to 50° C., preferably 10° C. to 40° C. The aqueous matrix typically comprises a pH range of 5 to 12, preferably 6 to 10, and most preferably 6 to 8. The temperature, pH, and/or ionic strength of the aqueous matrix can be adjusted to obtain the desired solubility characteristics of the fusion peptide/inclusion body.

The peptide of interest may be expressed as a fusion peptide having the following general structure:

IBT-CL-POI

Or POI-CL-IBT wherein;
IBT means at least one inclusion body tag;
CL means at least one cleavable peptide linker; and
POI means at least one peptide of interest.

As shown in the Examples, knockout mutations to several endogenous genes in *E. coli* increased the production of the heterologous fusion peptides. The model fusion peptides were comprised of an inclusion body tag coupled to a peptide of interest (HC776124 or HC415) via an acid labile aspartic acid—proline dipeptide (see U.S. patent application Ser. No. 11/782,836).

Cleavable Peptide Linkers

The use of cleavable peptide linkers is well known in the art. Fusion peptides comprising at least one inclusion body tag will typically include at least one cleavable sequence separating the inclusion body tag from the peptide of interest. The cleavable sequence facilitates separation of the inclusion body tag(s) from the peptide(s) of interest. The cleavable sequence may be provided by a portion of the inclusion body tag and/or the peptide of interest (e.g., inclusion of an acid cleavable aspartic acid—proline moiety). The cleavable sequence preferably includes in the fusion peptide at least one cleavable peptide linker between the inclusion body tag and the peptide of interest.

Means to cleave the peptide linkers are well known in the art and may include chemical hydrolysis, enzymatic cleavage agents, and combinations thereof. One or more chemically cleavable peptide linkers are included in the fusion construct to facilitate recovery of the peptide of interest from the inclusion body fusion protein. Examples of chemical cleavage reagents include cyanogen bromide, which cleaves methionine residues; N-chloro succinimide, iodobenzoic acid or BNPS-skatole [2-(2-nitrophenylsulfenyl)-3-methylindole], which cleaves tryptophan residues; dilute acids, which cleave at aspartyl-prolyl bonds, One or more aspartic acid—proline acid cleavable recognition sites (i.e., a cleavable peptide linker comprising one or more D-P dipeptide moieties) may preferably be included in the fusion protein construct to facilitate separation of the inclusion body tag(s) form the peptide of interest. The fusion peptide may include multiple regions encoding peptides of interest separated by one or more cleavable peptide linkers.

Moreover, one or more enzymatic cleavage sequences may be included in the fusion protein construct to facilitate recovery of the peptide of interest. Proteolytic enzymes and their respective cleavage site specificities are well known in the art. Preferably, the proteolytic enzyme is selected to specifically cleave only the peptide linker separating the inclusion body tag and the peptide of interest. Examples of enzymes useful for cleaving the peptide linker include, but are not limited to Arg-C proteinase, Asp-N endopeptidase, chymotrypsin, clostripain, enterokinase, Factor Xa, glutamyl endopeptidase, Granzyme B, *Achromobacter* proteinase I, pepsin, proline endopeptidase, proteinase K, Staphylococcal peptidase I, thermolysin, thrombin, trypsin, and members of the Caspase family of proteolytic enzymes (e.g. Caspases 1-10) (Walker, J. M., supra).

Typically, cleavage occurs after the insoluble inclusion bodies and/or insoluble fusion peptides are isolated from the cell lysate. Methods of lysing cells and isolation peptide from the cell lysate are well known in the art. Once isolated, the insoluble inclusion bodies and/or fusion peptides can be treated with a or enzymatic cleavage agent to cleave the inclusion body tag from the peptide of interest. After cleavage step, preferably, the peptide of interest can be separated and/or isolated from the fusion protein and the inclusion body tags based on a differential solubility of the components. Parameters such as pH, salt concentration, and temperature may be adjusted to facilitate separation of the inclusion body tag from the peptide of interest. The peptide of interest may be soluble or insoluble while the inclusion body tag and/or fusion protein is insoluble or soluble in the defined process matrix, typically aqueous. Optionally, the peptide of interest may be further purified using any number of well known purification techniques in the art such as ion exchange, gel purification techniques, and column chromatography (see U.S. Pat. No. 5,648,244).

Peptide-Based Reagents for Delivery of a Benefit Agent to a Body Surface

The methods described herein may produce peptide-based reagents comprising a first portion having affinity for a body surface and a second portion capable of being coupled to a benefit agent. The peptide-based reagent may a first binding domain (binding "hand") having multiple body surface-binding peptides ("fingers") and a second binding domain ("hand") having affinity for the benefit agent. The second binding domain may comprise multiple benefit agent-binding peptides. The benefit agent may be a peptide of interest itself or may be one or more molecules bound to, covalently or non-covalently, or associated with, the peptide of interest wherein the binding affinity of the peptide of interest is used to selectively target the benefit agent to the targeted material. The benefit agent may be a particulate benefit agent, such as a pigment or coated pigment.

The peptide of interest may comprise at least one region having an affinity for a targeted material and a plurality of regions having an affinity for a variety of benefit agents wherein the benefit agents may be the same or different. Examples of benefits agents include, but are not limited to, conditioners for personal care products, pigments, dye, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides; see SEQ ID NOs: 442-470).

Host Cells

Transcription, translation, and the protein biosynthetic apparatus are universal genetic processes. Examples of microbial production hosts may include, but are not limited to bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. Preferably, the host strain is a member of the genus *Escherichia*. The host strain may be *Escherichia coli*. The *Escherichia coli* host strain is preferably derived from a K-12 strain, such as *E. coli* K-12 substrain MG1655 (ATCC® 47076™).

Fermentation Media

Fermentation media must contain suitable carbon substrates. Suitable substrates may include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. L-arabinose is used to induce the present arabinose inducible expression system. As such, L-arabinose is typically not included in the fermentation media until expression of the desired chimeric gene (encoding the peptide or protein of interest) is desired. L-arabinose can be added at any time during the fermentation, although it is often preferable to induce expression only after a desired cell density/mass is achieved in the fermentor. It is contemplated that the source of carbon utilized in the present invention may encompass a wide variety of carbon containing substrates and will only be limited by the choice of organism. Preferred carbon substrates include glucose, fructose, and sucrose.

In addition to a carbon source, fermentation media may or must contain other components suitable and/or necessary for the growth of the cultures and promotion of the expression of the present fusion peptides. These are known to those skilled in the art and include minerals, salts, cofactors, buffers, etc.

Culture Conditions

Suitable growth conditions can vary and depend on the chosen production host and are generally known in the art. Typically, cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where pH 6.0 to pH 8.0 is preferred. Fermentation may be performed under either aerobic or anaerobic conditions whereas aerobic conditions are generally preferred.

Industrial Batch and Continuous Fermentations

Classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, (1992) 36:227-234.

Although typically performed in batch mode, it is contemplated that the methods described herein would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

The methods described herein may be practiced using either batch, fed-batch or continuous processes and that any known mode of fermentation would be suitable.

EXAMPLES

The Examples further describe by illustration only the cells and methods described above. From the above discussion and these Examples, one skilled in the art can ascertain the essential characteristics of the inventions recited in the claims. One of skill in the art will recognize that typically any amount, concentration, or other value or parameter that is given either as a range, preferred range, or a list of upper preferable values and lower preferable values, is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The meaning of abbreviations used is as follows: "min" means minute(s), "h" means hour(s), "μL" means microliter(s), "mL" means milliliter(s), "L" means liter(s), "nm" means nanometer(s), "mm" means millimeter(s), "μm" means micrometer(s), "μM" means micromolar, "mM" means millimolar, "M" means molar, "mmol" means millimole(s), "μmol" means micromole(s), "pmol" means picomole(s), "g" means gram(s), "μg" means microgram(s), "mg" means milligram(s), "g" means the gravitation constant, "rpm" means revolutions per minute, and "cat#" means catalog number, "PN" means part number.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or in Brock (supra). All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.) or Sigma-Aldrich Chemical Company (St. Louis, Mo.), unless otherwise specified.

Peptide Expression System

The peptide expression system used in the present examples is based on *Escherichia coli* MG1655 (ATCC® 47076™)-derived strain QC1100 in combination with a pBAD-based expression vector. The modified *E. coli* MG1655 strain comprising a disruption in the endogenous araBAD operon is referred to herein as *E. coli* strain KK2000 (the nucleic acid sequence of an araB promoter is provided as SEQ ID NO: 20). A knockout of slyD (SEQ ID NOs: 21 and 22) was engineered into KK2000 to reduce background of LUMIO™-based in-cell labeling. KK2000 containing the slyD knockout is referred to herein as *E. coli* strain QC1100.

The peptides were expressed as fusions which were designed to include at least one region encoding an inclusion body tag (IBT) linked to a peptide of interest (POI). Appropriate restriction sites were included in the expression system to facilitate simple swapping of the DNA encoding the inclusion body tag and/or peptide of interest. The fusion peptide was designed to have a cleavable peptide linker (for example, an acid cleavable aspartic acid—protein moiety (DP)) between the inclusion body tag (IBT) and the peptide of interest (POI). Furthermore, the fusion peptide was also designed to include at least one tetracysteine tag (LUMIO™ tag; SEQ ID NO: 1) located on the C-terminus of the inclusion body tag wherein the tetracysteine tag was separated from the portion encoding the peptide of interest by the cleavable peptide linker.

The peptide expression plasmid pLR199 (SEQ ID NO: 2) used in this application contains a ColE1 type origin of replication, the bla gene to confer ampicillin resistance and the aadA-1 gene to confer spectinomycin (Spec) resistance (see co-pending U.S. patent application Ser. No. 12/1263,608 to Cheng et al., incorporated herein by reference). The tag/peptide fusion construct was driven by the pBAD promoter. The plasmid also encodes the gene for the araC regulator. The fusion peptide construct in pLR199 contains a small inclusion body tag IBT139 (SEQ ID NO: 3) and the tetracysteine tag CCPGCC (SEQ ID NO: 1) followed by a peptide of interest (such as peptide HC776124; SEQ ID NO: 4), creating fusion peptide IBT139-CCPGCC-HC776124 (SEQ ID NOs: 5 and 6). The QC1100 strain containing the pLR199 vector was referred to as *E. coli* strain QC1101.

FACS System Operating Conditions:

A Fluorescence Activated Cell Sorter (FACSVANTAGE™ SE-DiVa; Becton-Dickinson (BD Biosciences, Franklin Lakes, N.J.)) was configured with a single 488 nm argon ion laser (200 mW). The laser is used to induce light scattering by either the excitation of cellular fluorescent tags or the granularity within the cell. The SSC (Side Scatter Collector) light detection from the cell is collected through a microscope objective, transmitted via fiber light guide to an array of photo-multiplier tubes (PMTs). The FSC (Forward Scatter Collector) was constructed of a photo-diode. The SSC octagon configuration was composed of 5 PMTs in an octagon configuration. The LUMIO™ collection at 530 nm used a fluorescein isothiocyanate (FITC) filter (530 nm center, +/−15 nm bands) with a SSC filter of 488 nm bandpass (488 nm center, +/−10 nm bands). The system fluid used on the FACSVANTAGE™ SE-DiVa was FACSFLOW™ Sheath (Becton Dickinson) at an operating pressure of 28 psi (~193 kPa) using a 70 μm diameter orifice tip.

The standard daily alignment of the instrument was performed using ALIGNFLOW™ (Molecular Probes, Inc., Eugene, Oreg.) 2.5 μm diameter fluorescent beads at an excitation/emission of 488 nm. The ALIGNFLOW™ beads were used as the daily alignment standard and the following instrument adjustments were made on the FACS to obtain the maximum PMT signal and minimum CV (coefficient of variation) for all channels on the instrument. The ALIGNFLOW™ beads were used to enable the daily adjustment of the FACS nozzle (X, Y, Z, α, and θ); in addition to the focus lens, channel height and channel height focus in all detector channels. The alignment of the FACS system can vary, but with the use of the ALIGNFLOW™ beads good alignment reproducibility was obtained. The ALIGNFLOW™ beads were either incorporated as a separate sample or directly into the sample to monitor the alignment and any potential instrument drift. The daily FACS alignment procedure, created in the DiVa Software (Becton Dickinson, v1.4), was performed and verified to within normal operating conditions.

The LUMIO™-stained cell samples were previously prepared in PBS (phosphate buffered saline) which is similar to the sheath fluid; therefore, no additional manipulation was needed for FACS analysis. Approximately 200 μL of a sample containing LUMIO™ stained cells was placed into a Falcon 12×75 mm, sterile polystyrene culture tube (Becton Dickinson) and into the instrument. The sample differential pressure was adjusted to obtain a stable 1000 events/second; at which, between 20,000 and 50,000 sample events were recorded. The variation, in sample recorded events, was due to the variation in cell concentration and limited sample volume. If the number of observed events was low, then the recorded events were then decreased. The samples scanned on the FACS for LUMIO™ analysis included, but were not limited to, an ALIGNFLOW™ bead sample, unstained LUMIO™ (negative control) and a series of LUMIO™ stained samples (experimental). The data obtained for the FACS samples included several different plot windows; which included dot plots for FSC-A vs SSC-A, FSC-A vs. FITC-A, SSC-A vs FITC-A and histograms for SSC-A, FSC-A, and FITC-A (width×height) for the particular channel ("A" is the computed area; "FS" is forward scatter; and "SS" is side scatter). During the recording of each sample, a gate was set on the FITC-A histogram between the $10^3$ and $10^4$ (log scale) to monitor and observe the sample LUMIO™ labeling efficiency. The recorded events within the gate on the FITC-A log scale provided a good indication of the sample LUMIO™ labeling efficiency. The recorded LUMIO™ sample data was saved and then within the DiVA software they were exported as FCS3 data files for further analysis.

TABLE 1

| Media/Buffer | Ingredient | Amount |
|---|---|---|
| Miller LB | Casein protein | 10 g/L |
| | NaCl | 10 g/L |
| | Yeast extract | 5 g/L |
| Dubelco's1X PBS | KCl | 0.2 g/L |
| | $KH_2PO_4$ | 0.2 g/L |
| | NaCl | 8 g/L |
| | $Na_2HPO_4*7H_2O$ | 2.16 g/L |
| DEK Media | $KH_2PO_4$ | 9 g/L |
| | $(NH_4)_2HPO_4$ | 4 g/L |
| | Citric acid*$H_2O$ | 1.86 g/L |
| | Yeast extract | 5 g/L |
| | Biospumex 153K | 0.1 mL/L |

TABLE 1-continued

| Media/Buffer | Ingredient | Amount |
|---|---|---|
| | (Post sterilization) | |
| | $MgSO_4*7H_2O$ | 1.2 g/L |
| | Thiamine HCl | 4.5 mg/L |
| | Trace elements (batch—see below) | 10 mL/L |
| | Uracil | 50 mg/L |
| Trace elements | EDTA | 840 mg/L |
| | $CoCl_2*6H_2O$ | 250 mg/L |
| | $MnCl_2*4H_2O$ | 1500 mg/L |
| | $CuCl_2*2H_2O$ | 150 mg/L |
| | $H_3BO_3$ | 300 mg/L |
| | $Na_2MoO_4*2H_2O$ | 250 mg/L |
| | $Zn(CH_3COO)_2*2H_2O$ | 1300 mg/L |
| | Fe(III) Citrate | 10000 mg/L |

Peptide Expression System

The peptide expression system used in this application was based on *E. coli* MG1655 (ATCC® 47076™) derived strain QC1100 in combination with a pBAD-based expression vector. The modified *E. coli* MG1655 strain comprising a disruption in the endogenous araBAD operon is referred to herein as *E. coli* strain KK2000. A knockout of slyD was engineered into KK2000 to reduce background of LUMIO™-based in-cell labeling. KK2000 containing the slyD knockout is referred to herein as *E. coli* strain QC1100.

The peptides were expressed as fusions which were designed to include at least one region encoding an inclusion body tag (IBT) linked to a peptide of interest (POI). Appropriate restriction sites were included to facilitate simple swapping of the portion encoding the inclusion body tag and/or peptide of interest. The fusion peptide was designed to have a cleavable peptide linker (for example, an acid cleavable DP moiety) between the inclusion body tag (IBT) and the peptide of interest (POI). Furthermore, the fusion peptide was also designed to include at least one tetracysteine tag (LUMIO™ tag; SEQ ID NO: 1) located on the C-terminus of the inclusion body tag wherein the tetracysteine tag was separated from the portion encoding the peptide of interest by the cleavable peptide linker. The tetracysteine tag could bind the FlAsH-$EDT_2$ reagent to provide in-cell LUMIO™ labeling.

The LUMIO™ protein detection system (Invitrogen Life Technologies, Carlsbad, Calif.) is based on the incorporation of a small tetracysteine tag (TC) that covalently binds to a biarsenical labeling reagent (e.g. FlAsH-$EDT_2$ [LUMIO™ green]; ReAsh-$EDT_2$ [LUMIO™ red]); and CHoXAsh-$EDT_2$ (U.S. Pat. No. 5,932,474; U.S. Pat. No. 6,054,271; U.S. Pat. No. 6,831,160; U.S. Pat. No. 6,008,378; U.S. Pat. No. 6,451,564; U.S. Pat. No. 6,686,458; U.S. Pat. No. 7,138,503; EP1032837, EP1684073, U.S. Pat. App. Pub. No. 20050176065 A1; and Griffin et al., *Science* 281:269-271 (1998)). Covalent binding of the labeling reagent to the tetracysteine tag generates a highly fluorescent complex.

The peptide expression plasmid pLR199 (SEQ ID NO: 2) used in the screen contains a ColE1 type origin of replication, the bla gene to confer ampicillin resistance and the aadA-1 gene to confer spectinomycin (Spec) resistance. The tag/peptide fusion construct is driven by the pBAD promoter. The plasmid also encodes the gene for the araC regulator. The fusion peptide construct in pLR199 contains a small inclusion body tag IBT139 (SEQ ID NO: 3) and the tetracysteine tag CCPGCC (SEQ ID NO: 1) followed by peptide of interest HC776124 (SEQ ID NO: 4), resulting in the construct pLR199 expressing the fusion peptide IBT139.CCPGCC.HC776124 (SEQ ID NOs: 5 and 6). (See U.S. patent application Ser. No. 12/263,608 for construction details). The QC1100 strain containing plasmid pLR199 is referred to herein as the QC1101 strain.

The expression plasmid pDCQ523 (SEQ ID NO: 7) was also used in the present examples. pDCQ523 (SEQ ID NO: 7) has similar vector backbone as pLR199 except that it expresses a different fusion peptide. Plasmid pDCQ523 expresses the fusion peptide consisted of the small inclusion body tag IBT139(5C) (SEQ ID NO: 8), the tetracysteine tag CCPGCC (SEQ ID NO: 1), followed by peptide of interest HC415. The nucleic acid sequence encoding the resulting fusion peptide IBT139(5C)-CCPGCC-HC415 is provided as SEQ ID NO: 9 and the corresponding amino acid sequence is provided as SEQ ID NO: 10. The nucleic acid sequence for HC415 is provided as SEQ ID NO: 11 and the corresponding amino acid sequence is provided as SEQ ID NO: 12.

Example 1

Construction and Sorting of a Transposon Insertion Library

This example describes construction of a transposon insertion library in a peptide production strain QC1101, which produced fusion peptide that contained the tetracysteine tag (CCPGCC; SEQ ID NO: 1). The tetracysteine tag allowed specific labeling of the fusion peptide by fluorescein derivative of biarsenical ligands FlAsH-EDT$_2$ (LUMIO™ Green), and sorting of the library by fluorescence on FACS. The LUMIO™ reagents were obtained from Invitrogen (Carlsbad, Calif.).

The transposon insertion library was constructed in a peptide production strain QC1101, which expressed the fusion peptide consisted of the small inclusion body tag IBT139 (SEQ ID NO: 3), the tetracysteine tag (SEQ ID NO: 1) followed by the peptide of interest HC776124 (SEQ ID NO: 4; See U.S. patent application Ser. No. 12/263,608; incorporated herein by reference). The Tn5-KAN transposome from Epicentre Technologies (Madison, Wis.) was used for the transposon mutagenesis with QC1101 strain following manufacturer's instruction. Approximately 38,000 transposon mutants were obtained and pooled. This transposon insertion library was designated as QC1150 library.

The QC1150 library cells were labeled using TC-FlAsH™ In-Cell tetracysteine tag detection kit (Invitrogen). The library cells were thawed from frozen stocks and grew for about 3 hours in 20 mL of DEK medium containing 0.4% glycerol with ampicillin (100 µg/mL) and kanamycin (25 µg/mL) till an OD$_{600}$ of about 1.5. The cells were then induced with 0.2% L-arabinose for about 3 hours. The induced cells were diluted and normalized to an OD$_{600}$ of about 1. Approximately 3×10$^7$ cells were then labeled with 20 µM FlAsH-EDT$_2$ reagent for 1.5 hours at room temperature (~22° C.) in the dark. The labeled cells were washed twice with BAL wash buffer and resuspended in PBS for sorting on FACS based on fluorescence. The gate for the first sort was set for the top 10% of fluorescent cells. About 100,000 events were collected and plated on LB plates with ampicillin (100 µg/mL) and kanamycin (25 µg/mL). The plates were incubated at 37° C. overnight. The colonies grew on the plates were pooled and aliquotes were used to grow cells for the next round of labeling following the same protocol as described above. The parameters used for each round of sorting is provided in Table 2. A total of four rounds of sorting was performed and aliquotes from each round were also frozen. About 200 colonies obtained from the fourth round of sorting was picked into microtiter plates for sequencing.

TABLE 2

Parameter used for sorting Library QC1150

| Round No. | Number of Events | Percent Sort of Previous Round (%) |
|---|---|---|
| QC1150$^a$ Library | NA | NA |
| 1 | 100,000 | 10% |
| 2 | 50,000 | 5% |
| 3 | 50,000 | 1% |
| 4 | 10,000 | 0.5% |

$^a$= Library QC1150 titer >38,000.

Example 2

Sequencing of the Sorted Clones

The transposon insertion site in each of the mutant was mapped by genomic sequencing using the ILLUSTRA™ GENOMIPHI™ v2 DNA Amplification kit from GE Healthcare (Piscataway, N.J.). The primers to sequence the chromosomal junction of both ends of the transposon were: Kan2cb-For (5'-CTGGTCCACCTACAACAAAGCTCTCATC-3'; SEQ ID NO: 13) and kan2cb-Rev (5'-CTTGTGCAATG-TAACATCAGAGATTTTGAGACAC-3'; SEQ ID NO: 14). The mutants selected for further analysis are listed in Table 3.

Among the sequenced clones, the highest number of hits was in the ftsN gene. Nine different ftsN mutants were obtained with the transposon inserted at different locations of the ftsN gene in different orientations. The ftsN gene was reported to be involved in cell division (Yang, J. C., et al. (2004), *Mol. Micro.* 52:651; Goehring, N. W., et al., (2007), *J. Bacteriol.* 189:646) and the higher fluorescence of the ftsN mutants might be an artifact of sorting as a result from defective cell division. The ftsN mutant was not pursued further.

The next highest number of hits was in the gcvA gene (SEQ ID NO: 15). Seven different gcvA mutants were isolated with the transposon inserted at different locations of the gcvA gene in the same orientation as the gcvA gene. The gcvA gene encodes a regulatory protein (GcvA; SEQ ID NO: 16) for glycine cleavage pathway (Wilson, R. L., and Stauffer, G. V., (1994), *J. Bacteriol.* 176:2862-2828). Two related mutants of the glycine cleavage system were also isolated containing transposon insertions in the gcvP gene. The gcvP gene encodes glycine decarboxylase, the largest catalytic protein (P-protein) in the glycine cleavage enzyme complex (Stauffer, L. T., et al., (1994), *Gene* 142:17-22). The glycine cleavage (GCV) enzyme system catalyzes the oxidative cleavage of glycine into $CO_2$ and $NH_3$ and transfers the one-carbon ($C_1$) methylene unit to tetrahydrofolate. This $C_1$-containing molecule, 5,10-methylenetetrahydrofolate, can then be used as the $C_1$ donor in the biosynthesis of purines, methionine, thymine, and other cellular components. The GCV system was shown to represent the major pathway of catabolism of glycine and serine. The genes encoding the three catalytic proteins of the GCV system (gcvTHP) are organized in an operon, which maps at 62.5 min on the *E. coli* chromosome. The gcvA gene encoding the regulatory protein which activates the GCV system is at a separate location at 60.3 min on the *E. coli* chromosome. Two mutants containing transposon insertions in the dam gene encoding DNA adenine methylase were also selected for further analysis, since the GCV system is related to cellular methylation reactions by providing the $C_1$ donors for methylation.

Several peptidase mutants were isolated once and were further characterized. A transposon mutant contained the insertion in the pbpG gene encoding D-alanyl-D-alanine endopeptidase. A transposon mutant contained the insertion in the spr gene (SEQ ID NO: 17) encoding a predicted peptidoglycan-hydrolyzing peptidase (Spr; SEQ ID NO: 18). A transposon mutant contained the insertion in the pepE gene encoding (alpha)-aspartyl dipeptidase. A transposon mutant contained the insertion in the prlC gene encoding oligopeptidase A.

ing kanamycin (25 μg/mL) plates. P1 lysates were prepared by growing P1clr100Cm phage with the individual Keio strains (Miller, J. H., (1972), *Experiments in Molecular Genetics*. Cold Spring Harbor Laboratory, Cold Spring Harbor, N.Y.). The phage lysates were then used to transduce the control strain QC1100. Mutants that contained the gene knockouts of interest were selected on kanamycin plates and confirmed by PCR. The kanamycin marker flanked by the FRT sites was removed by transient expression of the FLP plasmid pCP20 (Datsenko and Wanner, (2000) *PNAS*, 97:6640-6645). This resulted in strains QC1503, QC1504, QC1505, QC1506, QC1507, QC1508 and QC1509 contain-

TABLE 3

Summary of the selected transposon insertion mutants in *E. coli*

| Mutant | No. of hits | Gene Location | Coding Strand | Gene Function | Reference | Keio Strain[1] (ID No.) |
|---|---|---|---|---|---|---|
| ftsN | 9 | 4120403-4121362 | − | Cell division | Yang, J. C., et al., (2004), Mol. Micro. 52: 651 | NA |
| gcvA | 7 | 2939672-2940589 | − | DNA-binding transcriptional dual regulator | Wilson, R L, et al., (1994), J. Bacteriol. 176: 2862 | JW2779 |
| gcvP | 2 | 3044190-3047063 | − | glycine decarboxylase, subunit (protein P) of glycine cleavage complex | Stauffer, L. T., et al., (1994), Gene 142: 17 | JW2871 |
| dam | 2 | 3513099-3513935 | − | DNA adenine methylase | Lobner-Olesen, A., et al., (2005), Curr. Opin. Microbiol. 8: 154 | JW3350 |
| pbpG | 1 | 2221960-2222892 | − | D-alanyl-D-alanine endopeptidase | Romeis, T., et al., (1994), J. Biol. Chem. 269: 21603 | JW5355 |
| spr | 1 | 2268001-2268567 | + | predicted peptidase, outer membrane lipoprotein | Hara, H., et al., (1996), Micro Drug Resist 2: 63 | JW2163 |
| pepE | 1 | 4227476-4228165 | − | (alpha)-aspartyl dipeptidase | Conlin, C. A., et al., (1994), J. Bacteriol. 176: 1552 | JW3981 |
| prlC | 1 | 3641163-3643205 | − | oligopeptidase A, periplasmic protease | Hara, H., et al., (1991), J. Bacteriol. 173: 4799 | JW3465 |

[1] = Keio strain collection. Baba, T., et al., (2006) Mo.l Syst. Biol. 2: 2006.0008 (article No.).

Example 3

Confirmation of FACS Analysis with Clean Deletion Mutants

To verify that the genes interrupted by the transposon insertions were responsible for the phenotypes, clean mutants were reconstructed that contained the in-frame deletion of the particular single genes interrupted by the transposon insertions. A collection of the *E. coli* K12 in-frame single gene knockout mutants ("Keio collection") was licensed in house (Baba, T., et al., supra). The particular Keio knockout strains that corresponding to the transposon insertion mutants (see Table 3) were streaked out from the collection on LB containing the in-frame deletion of gcvA (SEQ ID NO: 15), pbpG, spr (SEQ ID NO: 17), pepE, gcvP, prlC or dam gene, respectively.

The peptide production plasmid pLR199 was transformed into the clean deletion strains. These strains were grown, induced and labeled for FACS analysis. Each strain was grown in 3 mL DEK containing 0.4% glycerol with ampicillin (100 μg/mL) and kanamycin (25 μg/mL) till an $OD_{600}$ of about 1.5. The cells were then induced with 0.2% L-arabinose for about 3 hours. The induced cells were labeled with 20 μM FlAsH-$EDT_2$ reagent for 1.5 hours at room temperature (~22° C.) in the dark. The labeled cells were washed twice with BAL wash buffer and resuspended in PBS. FACS analysis of these strains was shown in Table 4. The values were normalized and shown as the percentage to the respective values of the control strain QC1101. Among the seven strains, three showed higher fluorescence than the control. The spr mutant showed more than 300% higher fluorescence, the gcvA mutant showed about 150% higher fluorescence, and the gcvP mutant showed less than 110% higher fluorescence than the control.

TABLE 4

FACS Analysis of Various E. coli Strains with In-Frame Deletions

| Strain | FSC % relative to control QC1101 | SSC % relative to control QC1101 | FITC % relative to control QC1101 |
|---|---|---|---|
| QC1101 (control) | 100 | 100 | 100 |
| QC1503 (ΔgcvA) | 176.6 | 118.2 | 148.8 |
| QC1504 (ΔpbpG) | 98.0 | 94.6 | 68.2 |
| QC1505 (Δspr) | 356.4 | 161.0 | 332.3 |
| QC1506 (ΔpepE) | 99.5 | 91.3 | 83.3 |
| QC1507 (ΔgcvP) | 122.5 | 106.5 | 105.6 |
| QC1508 (ΔprlC) | 96.6 | 98.2 | 76.1 |
| QC1509 (Δdam) | 104.7 | 118.4 | 78.3 |

A double mutant that contained deletion of both spr and gcvA genes was constructed by P1 transduction as described above using P1 lysate from the spr strain JW2163 to transduce QC1503 containing the gcvA deletion. QC1510 strain containing deletion of both spr and gcvA genes was confirmed by PCR. Peptide production plasmid pLR199 was then transformed into QC1510 (ΔgcvA Δspr) resulting QC1513. QC1503 (ΔgcvA) and QC1505 (Δspr) containing the pLR199 plasmid were designated as strains QC1511 and QC1512. Triplicate cultures of strains QC1511, QC1512, QC1513 and the control strain, QC1101, were grown and induced as described above. The cultures were normalized to an $OD_{600}$ of 1 by dilution. Aliquots of the normalized cultures were used for in-cell labeling for FACS analysis (Example 3), for in-gel labeling for peptide quantitation (see Example 4), and for plate counts (see Example 5). The FACS analysis results are shown in Table 5. The forward scattering (FSC), side scattering (SSC) and fluorescence intensity (FITC) data are shown in three separate columns comparing uninduced vs. induced measurements. The standard deviation was calculated using 3 independent cultures. Both QC1511 and QC1512 showed higher average means of FSC, SSC and FITC than the control QC1101. The double mutant QC1513 showed even higher FSC, SSC and FITC means than either of the single mutant.

Example 4

Peptide Quantitation from Same OD Volume Cells

To determine if the mutant strains produced higher amount of fusion peptide, the cells were lysed and the fusion peptide was specifically labeled for in-gel analysis using the LUMIO™ Green detection kit (Invitrogen). The labeled peptide on the gel could be visualized under UV light. The intensity of the labeled peptide band could be quantified by image analysis. The linear range of the fluorescence images of the system was established using different amounts of the same labeling reaction mixture.

Triplicates of each of the E. coli strains (QC1511, QC1512, QC1513, and QC1101) were grown and induced as describe above. Same volume of normalized $OD_{600}$~1 cells were spun down and frozen for in-gel analysis. The pellets were lysed with B-PER® (Bacterial Protein Extraction Reagent) lysis buffer (Pierce Chemical Co., Rockford, Ill.). The whole cell lysate was labeled using the LUMIO™ Green detection kit (Invitrogen) following the manufacture's instructions. The stained lysate was run on a NUPAGE® 4-12% Bis-Tris gel with MES running buffer (Invitrogen). The BENCHMARK™ fluorescent protein standard (Invitrogen) was used. The gel was visualized under UV light.

After taking a picture (FIG. 1, top), the gel was rinsed, stained with SIMPLYBLUE™ (Invitrogen) and destained with deionized water (FIG. 1, bottom). The intensity of the fusion peptide band was quantified using ImageJ software (available from Rasband, W. S. Research Services Branch, National Institute of Mental Health, Bethesda, Md., USA & Abramoff, M. D., et al., (2004) *Biophotonics International*, 11(7) pp: 36-42). Results showed that when loaded same volume of same OD cells from each sample on the gel, the double mutant strain QC1513 produced about 130% as much fusion peptide as that of the control. Both single mutants QC1511 and QC1512 produced slightly less fusion peptide (about 90% and 80%) from the same volume of same OD cells as that of the control. They still produced more peptide than the control when normalized by cell numbers (Example 6)

Example 5

Mutants Showed Larger Cell Size

FACS analysis of QC1511, QC1512, QC1513 and QC1101 cells (Table 5) showed that all mutants have increased forward scattering (FSC). The Δspr mutant and the ΔgcvA Δspr double mutant had much higher FSC, which suggested the

TABLE 5

FACS Analysis of In-cell Labeled Strains[2]

| Strain | Uninduced FSC-A | Induced FSC-A | Uninduced SSC-A | Induced SSC-A | Uninduced FITC-A | Induced FITC-A |
|---|---|---|---|---|---|---|
| QC1101 (control) | 2836 | 3399 ± 97.6 | 1711 | 1965 ± 82.9 | 21 | 1157 ± 59.4 |
| QC1511 (ΔgcvA) | 3823 | 6791.7 ± 434.3 | 1664 | 2555.7 ± 159.8 | 24 | 3727.7 ± 163.7 |
| QC1512 (Δspr) | 8471 | 14692 ± 162.5 | 3051 | 3586.7 ± 78.1 | 134 | 3283 ± 171.1 |
| QC1513 (ΔgcvA Δspr) | 9147 | 17827 ± 726.0 | 4602 | 8016.7 ± 293.2 | 144 | 5535 ± 198.5 |

[2] = All values reported in relative units (RU) from FACS analysis.

cell size/shape of the mutants might have changed. The changed light scattering property of cells and the changed cell size/shape would affect the number of cells per $OD_{600}$ of cultures. The normalized ~1 $OD_{600}$ cultures of QC1511, QC1512, QC1513 and QC1101 as described in Example 3 were diluted for plating. The same volume (100 μL) of $10^{-4}$ serial dilutions from the normalized ~1 $OD_{600}$ cultures was plated on LB plates with appropriate antibiotics. Triplicate plating was performed for each culture. Nine platings were performed for the triplicate cultures of the same sample. Table 6 (below) shows the plate counts and standard deviations averaged from the nine data points for each sample. The lower cell counts from the $OD_{600}$ normalized cultures of the mutants were consistent with the larger FSC of the cells from FACS analysis. Other factors besides cell size might have contributed to the difference of cell viability as assayed by plate counts. Microscopic pictures of QC1513 and the QC1101 cells showed that QC1513 cells were about 2-3 times as large as QC1101 cells (data not shown).

TABLE 6

Average viable cell counts obtained from serial dilutions of the normalized cultures.

| E. coli strain ID | Average Plate Count | Standard Deviation |
|---|---|---|
| QC1101-1 (wild type) | 311.0 | 45.7 |
| QC1511 (ΔgcvA) | 118.0 | 60.0 |
| QC1512 (Δspr) | 10.0 | 5.7 |
| QC1513 (ΔgcvAΔspr) | 6.9 | 5.1 |

Example 6

Peptide Quantitation from Same Number Events Collected from FACS

To determine if high fluorescence intensity (FITC) from FACS analysis for the mutants correlated with high peptide content per cell, peptide in-gel quantitation (normalized by same number of cells for each sample) was done. Cells of strains QC1101, QC1511, QC1512 and QC1513 were grown and induced as described above. Five million events from the entire field of each sample (no set gate) were collected by FACS. After the FACS initial alignment (as described in the general methods), a sample of ALIGNFLOW™ 488 beads (Invitrogen; 2.5 μm, Catalog# A-7302) was used to adjust the PMT's (FSC, SSC and FITC) by placing the peaks for each channel at the same position within the channel histogram. This enabled consistent run-to-run PMT/sample adjustments. Typically, the bead peaks within the histograms were set as follows: FSC=40K, SSC=40K and FITC=20K.

The FACS settings for the collecting the 5 million events were as follows:

Instrument Configuration:

System Pressure=34 psi (~234.42 kPa)

Tip Orifice=70 μm

Frequency=62.2 KHz

Amplitude=10.6

Phase=125

DropDelay=27.48

ArgonIon Laser Power=200 mW

Sort rates were maintained between 5000 to 7000 events per second. The cells were collected into 15-mL conical tubes and about 11 mL of liquid was collected for each sample. The cells were centrifuged at 9800×g for 20 min at 4° C. The supernatants were removed until about 1-mL liquid was left in the tubes. The pelleted cells were then resuspended in the 1-mL liquid and transferred to 1.7-mL microfuge tubes. The residue cells in the conical tubes were washed with 0.5 mL of PBS and combined to the microfuge tubes. The microfuge tubes were then centrifuged at 15,000×g for 5 min. The supernatants were carefully removed without disturbing the cell pellets. The cell pellets were stored at −80° C. for in-gel analysis.

Figure 2:
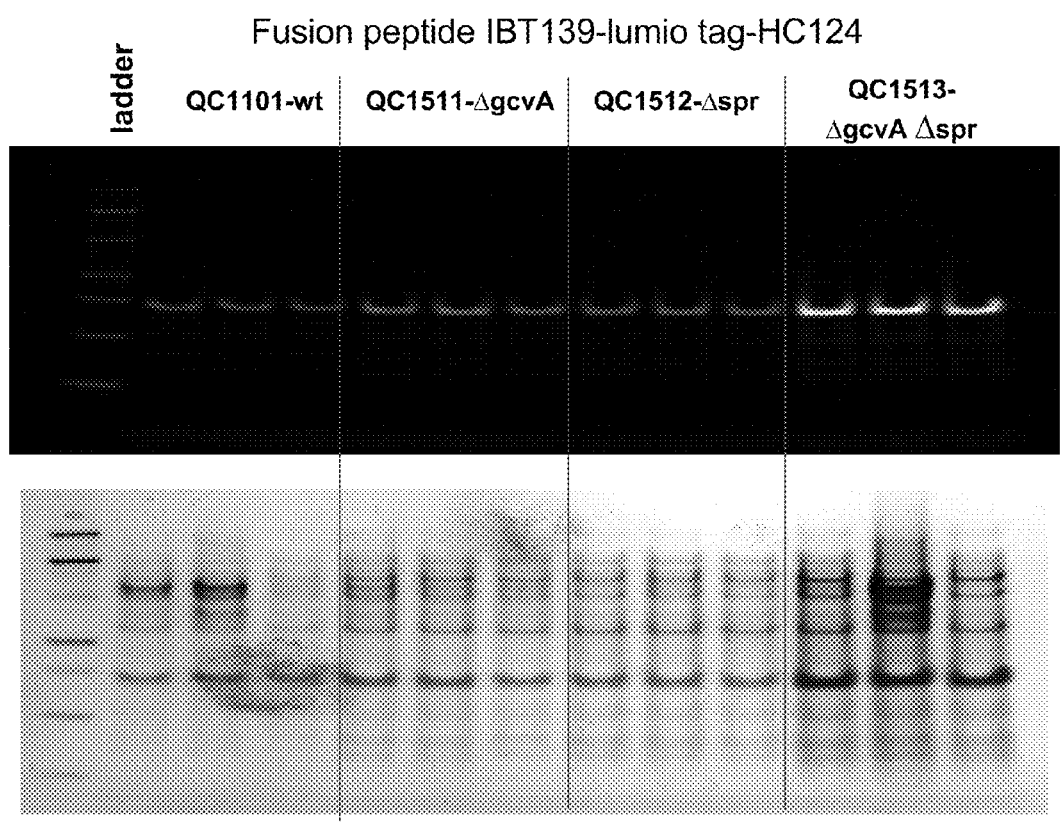
FIG. 2 shows the gel pictures (top and bottom panels) of the triplicate samples of QC1101-wt, QC1511-ΔgcvA, QC1512-Δspr, and QC1513-ΔgcvA Δspr loaded 5 million of FACS sorted events each lane as described in Example 6. The molecular weight ladder is shown in the far left lane. Top panel shows the specific in-gel labeling of the fusion peptide viewed under the UV light. The same gel stained with SIMPLYBLUE™ is also shown on the bottom panel.

The pellets were thawed and resuspended in 10-μL of B-PER® lysis buffer and vortex for 1 min to lyse the cells. The cells were labeled using the LUMIO™ Green detection kit (Invitrogen) following manufacture's instructions. LUMIO™ sample buffer (10 μL) was added to the 10 μL lysed cells and 0.2 μL of LUMIO™ reagent was added to each sample. The samples were heated at 70° C. for 10 min and briefly centrifuged after cooling to room temperature. LUMIO™ gel enhancer (2 μL) was then added to each sample, which were incubated at room temperature (~22° C.) for 5 min. The entire sample in the tube was loaded onto NUPAGE® 4-12% Bis-Tris gel. After gel electrophoresis, the gel was visualized under UV light. After taking a picture (FIG. 2, top), the gel was rinsed, stained with SIMPLY-BLUE™ (Invitrogen) and destained with deionized water (FIG. 2, bottom). The intensity of the fusion peptide band was quantified using the ImageJ software.

Image analysis of the gel loaded with 5 million events from each sample showed QC1511 had 48% more fusion peptide IBT139-CCPGCC-HC776124 and QC1512 had 36% more fusion peptide than the control. (Table 7.)

TABLE 7

Relative Fluorescence Band Intensity for Various Strains

| Strain | Relative Fluorescence band Intensity | Fold increase vs. QC1101 |
|---|---|---|
| QC1101—control | 0.88 ± 0.39 | — |
| QC1511 (ΔgcvA) | 1.31 ± 0.12 | 1.48 |
| QC1512 (Δspr) | 1.21 ± 0.05 | 1.36 |
| QC1513 (ΔgcvA Δspr) | 3.83 ± 0.14 | 4.34 |

QC1513 had 4.3 times as much fusion peptide as the control. Either the ΔgcvA mutant (QC1511) or the Δspr mutant (QC1512) increased peptide production per cell. The double ΔgcvA Δspr mutant (QC1513) showed a synergistic effect that drastically increased peptide production.

Example 7

Evaluation of Different Peptide Production in the Mutants

To determine if the effect of ΔgcvA Δspr mutant on increasing peptide production is general or peptide specific, we tested a different fusion peptide IBT139(5C)-CCPGCC-HC415 (SEQ ID NO: 10) expressed from pDCQ523.

Plasmid pDCQ523 (SEQ ID NO: 7) was created by inserting the annealed oligonucleotides containing the LUMIO™ tag CCPGCC into the plasmid pLR538 expressing IBT139 (5C)-HC415.

The elements of HC415 are provided in Table 9. The hair binding domain of HC415 comprises hair-binding peptide "HP2" (AQSQLPDKHSGLHERAPQRY; SEQ ID NO: 105) linked to hair-binding peptide "MEA4" (HINKTNPHQGN-HHSEKTQRQ; SEQ ID NO: 99) through a peptide linker (GPEEAAKKEEAAKKPA; SEQ ID NO: 19). The opposite end of HC415 has a pigment-binding domain with two copies of the iron oxide-based pigment-binding peptide Rfe5 (DSHHNHHKQDSRPQHRKTPN; SEQ ID NO: 363 separated by a polyglycine linker.

TABLE 8

Fusion Peptide Components

| Component | Amino Acid Sequence |
|---|---|
| IBT139(5C) | SEQ ID NO: 8 |
| HC415 | SEQ ID NO: 12 |
| IBT139(5C)-CCPGCC-HC415 | SEQ ID NO: 10 |

TABLE 9

Fusion peptide HC415

| Peptide ID | Formula³ | Amino Acid Sequence |
|---|---|---|
| HC415 | DPS-HP2-*GPEEAAKKEEAAKKPA*-MEA4-*GSGGGGSGSGGGGS*-Rfe5-*GGG*-Rfe5-GK | DPS-AQSQLPDKHSGLHERAPQRY-GPEEAAKKEEAAKKPA-HINKTNPHQGNHHSEKTQRQ-GSGGGGSGSGGGGS-DSHHNHHKQDSRPQHRKTPN-GGG-DSHHNHHKQDSRPQHRKTPN-GK (SEQ ID NO: 12) |

³= hair binding and pigment-binding peptides previously identified by biopanning are in bold. The peptide linkers are italicized.

Plasmid pDCQ523 was transformed into the control (strain QC1525) and the ΔgcvA Δspr mutant (strain QC1527). Cells of QC1525 and QC1527 were grown and induced as above. Five million events were collected by FACS and analyzed by in-gel LUMIO™ labeling as described in Example 6. The results are provided in Table 10.

TABLE 10

FACS and SIMPLE BLUE ™ staining analysis of peptide produced by strains QC1525 and QC1527.

| Detection Method | Strain | Relative Fluorescence band Intensity (fold increase vs. QC1525) |
|---|---|---|
| Fluorescence | QC1525 (ΔslyD) | 0.30 ± 0.12 |
|  | QC1527 (ΔslyD ΔgcvA Δspr) | 1.48 ± 0.14 (4.93) |
| SIMPLE BLUE ™ Stain | Strain | Relative SIMPLE BLUE ™ band Intensity (fold increase vs. QC1525) |
|  | QC1525 (ΔslyD) | 1.34 ± 0.62 |
|  | QC1527 (ΔslyD ΔgcvA Δspr) | 4.94 ± 0.09 (3.69) |

As shown from the in gel fluorescence labeling in Table 10, QC1527 produced 4.9-fold as much of fusion peptide IBT139 (5C)-CCPGCC-HC415 as the QC1525 control. This was similar to the 4.3-fold increase of fusion peptide IBT139-CCPGCC-HC776124 in the ΔgcvA Δspr double mutant QC1513 than the QC1101 control. This indicated that the effect of the double knockout ΔgcvA Δspr mutant on increasing peptide production is applicable to different peptides.

What is claimed is:

1. A recombinant *Escherichia* host cell, comprising:
   i) a chimeric genetic construct encoding a peptide of interest;
   ii) a knockout mutation in gene gcvA (encoding the glycine cleavage enzyme); and
   iii) a knockout mutation in gene spr (encoding the suppressor of prc),
   wherein the knockout mutation increases the amount of peptide produced in said recombinant host cell when compared to a non-modified *Escherichia* host cell lacking the knockout mutations grown under identical reaction conditions.

2. The recombinant *Escherichia* host cell of claim 1, wherein the peptide of interest is from 14 to 600 amino acids in length and preferably a single chain peptide of 14 to 600 amino acids in length.

3. The recombinant *Escherichia* host cell of claim 1, wherein the *Escherichia* host cell further comprises a disruption in endogenous araBAD operon, endogenous slyD gene or both.

4. The recombinant *Escherichia* host cell of claim 3, wherein the peptide of interest has affinity for a body surface selected from the group consisting of hair, skin, nail, tooth, and tooth pellicle.

5. The recombinant *Escherichia* host cell of claim 4, wherein the peptide of interest comprises at least one domain having affinity for said body surface, as measured by an $MB_{50}$ or $K_D$, of $10^{-5}$ M or less.

6. The recombinant *Escherichia* host cell of claim 1, wherein the peptide of interest is expressed as a fusion peptide that is insoluble within the *Escherichia* host cell and preferably has the general structure:

IBT-CL-POI or

POI-CL-IBT wherein;
   IBT=at least one inclusion body tag;
   CL=at least one cleavable peptide linker; and
   POI=at least one peptide of interest.

7. The recombinant *Escherichia* host cell of claim 6, wherein the *Escherichia* host cell further comprises a disruption in endogenous araBAD operon, endogenous slyD gene or both.

8. The recombinant *Escherichia* host cell of claim 7, wherein the peptide of interest comprises at least one domain having affinity for said body surface, as measured by an $MB_{50}$ or $K_D$, of $10^{-5}$ M or less.

9. The recombinant *Escherichia* host cell of claim 8, wherein the peptide of interest comprises at least one domain having affinity for said body surface, as measured by an $MB_{50}$ or $K_D$, of $10^{-5}$ M or less.

10. A method of producing a peptide of interest in an *Escherichia* host cell, comprising:
    a) providing an *Escherichia* host cell comprising
       i) at least one chimeric genetic construct encoding a peptide of interest; and
       ii) a knockout mutation selected from the group consisting of gene gcvA, gene spr and a combination of both;
    b) growing the *Escherichia* host cell of (a) to produce the peptide of interest; and
    c) optionally recovering the peptide of interest produced in step (b).

11. The method of claim 10, wherein the knockout mutation increases the amount of peptide produced at least 1.25 fold when compared to a non-modified *Escherichia* host cell lacking the knockout mutations grown under identical reaction conditions.

12. The method of clam 10, wherein the peptide of interest is from 14 to 600 amino acids in length and preferably a single chain peptide of 14 to 600 amino acids in length.

13. The method of claim 10, wherein the peptide of interest is expressed as a fusion peptide that is insoluble within the *Escherichia* host cell.

14. The method of claim 10, wherein the peptide of interest has affinity for a body surface selected from the group consisting of hair, skin, nail, tooth, and tooth pellicle.

15. The method of claim 14, wherein the peptide of interest comprises at least one domain having affinity for said body surface, as measured by an $MB_{50}$ or $K_D$, of $10^{-5}$ M or less.

16. The method of claim 11, wherein the fusion peptide has the general structure:

IBT-CL-POI or

POI-CL-IBT wherein;

IBT=at least one inclusion body tag;
CL=at least one cleavable peptide linker; and
POI=at least one peptide of interest.

17. The method of claim 11, wherein the *Escherichia* host cell further comprises a disruption in endogenous araBAD operon, endogenous slyD gene or both and preferably lacks a down-regulated or disrupted copy of a endogenous protease gene selected from the group consisting of degP, prc, ompT, ptr3, and combinations thereof.

18. The method of claim 11, wherein the peptide of interest has affinity for a body surface selected from the group consisting of hair, skin, nail, tooth, and tooth pellicle.

19. The method of claim 18, wherein the peptide of interest comprises at least one domain having affinity for said body surface, as measured by an $MB_{50}$ or $K_D$, of $10^{-5}$ M or less.

* * * * *

SEQUENCE LISTING

```
<160> NUMBER OF SEQ ID NOS: 470

<210> SEQ ID NO 1
<211> LENGTH: 6
<212> TYPE: PRT
<213> ORGANISM: artificial sequence
<220> FEATURE:
<223> OTHER INFORMATION: Synthetic construct - tetracysteine tag

<400> SEQUENCE: 1

Cys Cys Pro Gly Cys Cys
1               5

<210> SEQ ID NO 2
<211> LENGTH: 6034
<212> TYPE: DNA
<213> ORGANISM: artificial sequence
<220> FEATURE:
<223> OTHER INFORMATION: plasmid

<400> SEQUENCE: 2
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaaagtg tctataatca cggcagaaaa gtccacattg     180
attatttgca cggcgtcaca ctttgctatg ccatagcatt tttatccata agattagcgg     240
atcttacctg acgcttttta tcgcaactct ctactgtttc tccatacccg ttttttgggc     300
taacaggagg aattacatat gcagcagcgt ttccagtggc agttcgaaca gcagccgcgt     360
ggtcagcagc gtttccagtg gcagttcgaa cagcagccgc gtggtcagca gcgtttccag     420
```

-continued

```
tggcagttcg aacagcagcc ggaaggtcag cagcgtttcc agtggcagtt cgaacagcag      480
ggatcttgct gtccgggctg ttgcggatcc gaccctggca ttccgtggtg aacattcgt       540 gctcctctga atgcaggtgc gggcatccct tggtggaata ttcgtgctcc gctgaacgcc      600
ggtggttccg gtccgggtag cggtggtaat acttctcagc tgtccacggg tggcggtaac      660
actagccagc tgagcacggg cggccctaaa aagccgggcg acccgggtat tccgtggtgg      720
aatatccgtg ccccgctgaa cgcaggtgcc ggcatcccgt ggtggaacat tcgtgcacct      780
ctgaatgctg gtggttccgg tccaggctct ggcggcaaca cttcccagct gtccaccggc      840
ggtggcaaca ccagccagct gtctactggt ggtccgaaga aaccgggtga ctaataaggc      900
gcgccgaccc agcttttctt gtacaaagtgg ttgattcgag gctgctaaca aagcccgaaa     960
ggaagctgag ttggctgctg ccaccgctga gcaataacta gcataacccc ttggggcctc     1020
taaacgggtc ttgaggggtt ttttgctgaa aggaggaact atatccggat atccacagga     1080
cgggtgtggt cgccatgatc gcgtagtcga tagtggctcc aagtagcgaa gcgagcagga     1140
ctgggcggcg gccaaagcgg tcggacagtg ctccgagaac gggtgcgcat agaaattgca     1200
tcaacgcata tagcgctagc agcacgccat agtgactggc gatgctgtcg gaatggacga     1260
tatcccgcaa gaggcccggc agtaccggca taaccaagcc tatgcctaca gcatccaggg     1320
tgacggtgcc gaggatgacg atgagcgcat tgttagattt catacacggt gcctgactgc     1380
gttagcaatt taactgtgat aaactaccgc attaaagctt gcagtggcgg ttttcatggc     1440
ttgttatgac tgttttttg gggtacagtc tatgcctcgg gcatccaagc agcaagcgcg     1500
ttacgccgtg ggtcgatgtt tgatgttatg gagcagcaac gatgttacgc agcagggcag     1560
tcgccctaaa acaaagttaa acatcatgag ggaagcggtg atcgccgaag tatcgactca     1620
actatcagag gtagttggcg tcatcgagcg ccatctcgaa ccgacgttgc tggccgtaca     1680
tttgtacggc tccgcagtgg atggcggcct gaagccacac agtgatattg atttgctggt     1740
tacggtgacc gtaaggcttg atgaaacaac gcggcgagct ttgatcaacg accttttgga     1800
aacttcggct tcccctggag agagcgagat tctccgcgct gtagaagtca ccattgttgt     1860
gcacgacgac atcattccgt ggcgttatcc agctaagcgc gaactgcaat tggagaatg     1920 gcagcgcaat gacattcttg caggtatctt cgagccagcc acgatcgaca ttgatctggc     1980
tatcttgctg acaaaagcaa gagaacatag cgttgccttg gtaggtccag cggcggagga     2040
actctttgat ccggttcctg aacaggatct atttgaggcg ctaaatgaaa ccttaacgct     2100
atggaactcg ccgcccgact gggctggcga tgagcgaaat gtagtgctta cgttgtcccg     2160
catttggtac agcgcagtaa ccggcaaaat cgcgccgaag gatgtcgctg ccgactgggc     2220
aatggagcgc ctgccggccc agtatcagcc cgtcatactt gaagctagac aggcttatct     2280
tggacaagaa gaagatcgct tggcctcgcg cgcagatcag ttggaagaat tgtccacta     2340 cgtgaaaggc gagatcacca aggtagtcgg caaataatgt ctaacaattc gttcaagctt     2400
ggctgttttg gcggatgaga gaagattttc agcctgatac agattaaatc agaacgcaga     2460
agcggtctga taaaacagaa tttgcctggc ggcagtagcg cggtggtccc acctgacccc     2520
atgccgaact cagaagtgaa acgccgtagc gccgatggta gtgtggggtc tccccatgcg     2580
agagtaggga actgccaggc atcaaataaa acgaaaggct cagtcgaaag actgggcctt     2640
tcgttttatc tgttgtttgt cggtgaacgc tctcctgagt aggacaaatc cgccgggagc     2700
ggatttgaac gttgcgaagc aacggcccgg agggtggcgg gcaggacgcc cgccataaac     2760
```

```
tgccaggcat caaattaagc agaaggccat cctgacggat ggccttttg cgtttctaca      2820 aactcttttg tttattttc taaatacatt caaatatgta tccgctcatg agacaataac      2880
cctgataaat gcttcaataa tattgaaaaa ggaagagtat gagtattcaa catttccgtg      2940
tcgcccttat tccctttttt gcggcatttt gccttcctgt ttttgctcac ccagaaacgc      3000
tggtgaaagt aaaagatgct gaagatcagt tgggtgcacg agtgggttac atcgaactgg      3060
atctcaacag cggtaagatc cttgagagtt ttcgccccga agaacgtttt ccaatgatga      3120
gcacttttaa agttctgcta tgtggcgcgg tattatcccg tgttgacgcc gggcaagagc      3180
aactcggtcg ccgcatacac tattctcaga atgacttggt tgagtactca ccagtcacag      3240
aaaagcatct tacggatggc atgacagtaa gagaattatg cagtgctgcc ataaccatga      3300
gtgataacac tgcggccaac ttacttctga acgatcgg aggaccgaag gagctaaccg      3360
cttttttgca caacatgggg gatcatgtaa ctcgccttga tcgttgggaa ccggagctga      3420
atgaagccat accaaacgac gagcgtgaca ccacgatgcc tgtagcaatg gcaacaacgt      3480
tgcgcaaact attaactggc gaactactta ctctagcttc ccggcaacaa ttaatagact      3540
ggatggaggc ggataaagtt gcaggaccac ttctgcgctc ggcccttccg gctggctggt      3600
ttattgctga taaatctgga gccggtgagc gtgggtctcg cggtatcatt gcagcactgg      3660
ggccagatgg taagccctcc cgtatcgtag ttatctacac gacggggagt caggcaacta      3720
tggatgaacg aaatagacag atcgctgaga taggtgcctc actgattaag cattggtaac      3780
tgtcagacca agtttactca tatatacttt agattgattt aaaacttcat ttttaattta      3840
aaaggatcta ggtgaagatc ctttttgata atctcatgac caaaatccct aacgtgagt      3900 tttcgttcca ctgagcgtca gaccccgtag aaaagatcaa aggatcttct tgagatcctt      3960 ttttttctgcg cgtaatctgc tgcttgcaaa caaaaaaacc accgctacca gcggtggttt      4020
gtttgccgga tcaagagcta ccaactcttt ttccgaaggt aactggcttc agcagagcgc      4080
agataccaaa tactgtcctt ctagtgtagc cgtagttagg ccaccacttc aagaactctg      4140
tagcaccgcc tacatacctc gctctgctaa tcctgttacc agtggctgct gccagtggcg      4200
ataagtcgtg tcttaccggg ttggactcaa gacgatagtt accggataag cgcagcggt      4260 cgggctgaac ggggggttcg tgcacacagc ccagcttgga gcgaacgacc tacaccgaac      4320
tgagatacct acagcgtgag ctatgagaaa gcgccacgct cccgaaggg agaaaggcgg      4380 acaggtatcc ggtaagcggc agggtcggaa caggagagcg cacgagggag cttccagggg      4440
gaaacgcctg gtatctttat agtcctgtcg ggtttcgcca cctctgactt gagcgtcgat      4500
ttttgtgatg ctcgtcaggg gggcggagcc tatggaaaaa cgccagcaac gcggcctttt      4560
tacggttcct ggccttttgc tggccttttg ctcacatgtt ctttcctgcg ttatcccctg      4620
attctgtgga taaccgtatt accgcctttg agtgagctga taccgctcgc cgcagccgaa      4680
cgaccgagcg cagcgagtca gtgagcgagg aagcggaaga gcgcctgatg cggtattttc      4740
tccttacgca tctgtgcggt atttcacacc gcatatatgg tgcactctca gtacaatctg      4800
ctctgatgcc gcatagttaa gccagtatac actccgctat cgctacgtga ctgggtcatg      4860
gctgcgcccc gacacccgcc aacacccgct gacgcgccct gacgggcttg tctgctcccg      4920
gcatccgctt acagacaagc tgtgaccgtc tccgggagct gcatgtgtca gaggttttca      4980
ccgtcatcac cgaaacgcgc gaggcagcag atcaattcgc gcgcgaaggc gaagcggcat      5040
gcataatgtg cctgtcaaat ggacgaagca gggattctgc aaaccctatg ctactccgtc      5100
aagccgtcaa ttgtctgatt cgttaccaat tatgacaact tgacggctac atcattcact      5160
```

-continued

```
ttttcttcac aaccggcacg gaactcgctc gggctggccc cggtgcattt tttaaatacc   5220
cgcgagaaat agagttgatc gtcaaaacca acattgcgac cgacggtggc gataggcatc   5280
cgggtggtgc tcaaaagcag cttcgcctgg ctgatacgtt ggtcctcgcg ccagcttaag   5340
acgctaatcc ctaactgctg gcggaaaaga tgtgacagac gcgacggcga caagcaaaca   5400
tgctgtgcga cgctggcgat atcaaaattg ctgtctgcca ggtgatcgct gatgtactga   5460
caagcctcgc gtacccgatt atccatcggt ggatggagcg actcgttaat cgcttccatg   5520
cgccgcagta acaattgctc aagcagattt atcgccagca gctccgaata gcgcccttcc   5580
ccttgcccgg cgttaatgat ttgcccaaac aggtcgctga atgcggctg gtgcgcttca    5640 tccgggcgaa agaaccccgt attggcaaat attgacggcc agttaagcca ttcatgccag   5700
taggcgcgcg gacgaaagta aacccactgg tgataccatt cgcgagcctc cggatgacga   5760
ccgtagtgat gaatctctcc tggcgggaac agcaaaatat cacccggtcg gcaaacaaat   5820
tctcgtccct gattttttcac caccccctga ccgcgaatgg tgagattgag aatataacct   5880
ttcattccca gcggtcggtc gataaaaaaa tcgagataac cgttggcctc aatcggcgtt   5940
aaacccgcca ccagatgggc attaaacgag tatcccggca gcagggggatc attttgcgct   6000 tcagccatac ttttcatact cccgccattc agag                                6034
```

<210> SEQ ID NO 3
<211> LENGTH: 53
<212> TYPE: PRT
<213> ORGANISM: artificial sequence
<220> FEATURE:
<223> OTHER INFORMATION: inclusion body tag IBT139

<400> SEQUENCE: 3

```
Gln Gln Arg Phe Gln Trp Gln Phe Glu Gln Gln Pro Arg Gly Gln Gln
1               5                   10                  15

Arg Phe Gln Trp Gln Phe Glu Gln Gln Pro Arg Gly Gln Gln Arg Phe
            20                  25                  30

Gln Trp Gln Phe Glu Gln Gln Pro Glu Gly Gln Gln Arg Phe Gln Trp
        35                  40                  45

Gln Phe Glu Gln Gln
    50
```

<210> SEQ ID NO 4
<211> LENGTH: 129
<212> TYPE: PRT
<213> ORGANISM: artificial sequence
<220> FEATURE:
<223> OTHER INFORMATION: Synthetic construct. Multi-block hair-binding peptide

<400> SEQUENCE: 4

```
Gly Ser Asp Pro Gly Ile Pro Trp Trp Asn Ile Arg Ala Pro Leu Asn
1               5                   10                  15

Ala Gly Ala Gly Ile Pro Trp Trp Asn Ile Arg Ala Pro Leu Asn Ala
            20                  25                  30

Gly Gly Ser Gly Pro Gly Ser Gly Gly Asn Thr Ser Gln Leu Ser Thr
        35                  40                  45

Gly Gly Gly Asn Thr Ser Gln Leu Ser Thr Gly Gly Pro Lys Lys Pro
    50                  55                  60

Gly Asp Pro Gly Ile Pro Trp Trp Asn Ile Arg Ala Pro Leu Asn Ala
65                  70                  75                  80
```

```
Gly Ala Gly Ile Pro Trp Trp Asn Ile Arg Ala Pro Leu Asn Ala Gly
            85                  90                  95

Gly Ser Gly Pro Gly Ser Gly Gly Asn Thr Ser Gln Leu Ser Thr Gly
            100                 105                 110

Gly Gly Asn Thr Ser Gln Leu Ser Thr Gly Gly Pro Lys Lys Pro Gly
        115                 120                 125

Asp

<210> SEQ ID NO 5
<211> LENGTH: 579
<212> TYPE: DNA
<213> ORGANISM: artificial sequence
<220> FEATURE:
<223> OTHER INFORMATION: Synthetic construct - chimeric gene encoding
      fusion peptide IBT139.CCPGCC-HC776124

<400> SEQUENCE: 5
atgcagcagc gtttccagtg gcagttcgaa cagcagccgc gtggtcagca gcgtttccag     60
tggcagttcg aacagcagcc gcgtggtcag cagcgtttcc agtggcagtt cgaacagcag    120
ccggaaggtc agcagcgttt ccagtggcag ttcgaacagc agggatcttg ctgtccgggc    180
tgttgcggat ccgaccctgg cattccgtgg tggaacattc gtgctcctct gaatgcaggt    240
gcgggcatcc cttggtggaa tattcgtgct ccgctgaacg ccgtggttc cggtccgggt     300 agcggtggta atacttctca gctgtccacg ggtggcggta acactagcca gctgagcacg    360
ggcggcccta aaaagccggg cgaccccgggt attccgtggt ggaatatccg tgccccgctg    420
aacgcaggtg ccggcatccc gtggtggaac attcgtgcac tctgaatgc tggtggttcc    480 ggtccaggct ctggcggcaa cacttcccag ctgtccaccg gcggtggcaa caccagccag    540
ctgtctactg gtggtccgaa gaaaccgggt gactaataa                           579

<210> SEQ ID NO 6
<211> LENGTH: 190
<212> TYPE: PRT
<213> ORGANISM: artificial sequence
<220> FEATURE:
<223> OTHER INFORMATION: Synthetic construct - fusion peptide
      IBT139.CCPGCC-HC776124

<400> SEQUENCE: 6

Gln Gln Arg Phe Gln Trp Gln Phe Glu Gln Gln Pro Arg Gly Gln Gln
1               5                   10                  15

Arg Phe Gln Trp Gln Phe Glu Gln Gln Pro Arg G

```
Ile Pro Trp Trp Asn Ile Arg Ala Pro Leu Asn Ala Gly Gly Ser Gly
145                 150                 155                 160

Pro Gly Ser Gly Gly Asn Thr Ser Gln Leu Ser Thr Gly Gly Gly Asn
            165                 170                 175

Thr Ser Gln Leu Ser Thr Gly Gly Pro Lys Lys Pro Gly Asp
        180                 185                 190

<210> SEQ ID NO 7
<211> LENGTH: 6034
<212> TYPE: DNA
<213> ORGANISM: artificial sequence
<220> FEATURE:
<223> OTHER INFORMATION: plasmid

<400> SEQUENCE: 7
```

| | | | |
|---|---|---|---|
| aagaaaccaa ttgtccatat tgcatcagac attgccgtca ctgcgtcttt tactggctct | 60 |
| tctcgctaac caaaccggta accccgctta ttaaaagcat tctgtaacaa agcgggacca | 120 |
| aagccatgac aaaaacgcgt aacaaagtg tctataatca cggcagaaaa gtccacattg | 180 |
| attatttgca cggcgtcaca ctttgctatg ccatagcatt tttatccata agattagcgg | 240 |
| atcttacctg acgctttta tcgcaactct ctactgtttc tccataccccg ttttttgggc | 300 |
| taacaggagg aattacatat ggctagctgc ggtcaacaac gttttcaatg caattcgaa | 360 |
| caacagccgc gttgcggcca gcaacgcttc caatggcagt ttgaacagca accgcgttgc | 420 |
| ggtcagcaac gtttccagtg gcaatttgaa caacagccag agtgcggcca gcagcgcttt | 480 |
| cagtggcagt tcgagcagca gccgtgcgga tcttgctgtc cgggctgttg cggatccgat | 540 |
| ccatctgctc aatctcaact gcctgataaa cattctggtc tgcatgaacg cgctcctcaa | 600 |
| cgttacggtc cggaggaggc ggcgaagaaa gaagaggcgg ctaaaaagcc ggctcacatt | 660 |
| aataagacca acccgcatca gggcaaccat cactccgaaa agacccagcg tcagggctcc | 720 |
| ggtggcggcg gtagcggcag cggtggcggt ggttctgact cccatcacaa ccatcacaag | 780 |
| caggactccc gccctcagca ccgtaagacg ccaaacggcg gtggtgactc tcaccataac | 840 |
| caccacaaac aggactctcg cccgcagcac cgcaaaaccc ctaacggtaa ataataaggc | 900 |
| gcgccgaccc agcttcttg tacaaagtgg ttgattcgag gctgctaaca aagcccgaaa | 960 |
| ggaagctgag ttggctgctg ccaccgctga gcaataacta gcataacccc ttggggcctc | 1020 |
| taaacgggtc ttgagggggtt ttttgctgaa aggaggaact atatccggat atccacagga | 1080 |
| cgggtgtggt cgccatgatc gcgtagtcga tagtggctcc aagtagcgaa gcgagcagga | 1140 |
| ctgggcggcg gccaaagcgg tcggacagt ctccgagaac gggtgcgcat agaaattgca | 1200 |
| tcaacgcata tagcgctagc agcacgccat agtgactggc gatgctgtcg gaatggacga | 1260 |
| tatcccgcaa gaggcccggc agtaccggca taaccaagcc tatgcctaca gcatccaggg | 1320 |
| tgacggtgcc gaggatgacg atgagcgcat tgttagattt catacacggt gcctgactgc | 1380 |
| gttagcaatt taactgtgat aaactaccgc attaaagctt gcagtggcgg ttttcatggc | 1440 |
| ttgttatgac tgttttttg gggtacagtc tatgcctcgg gcatccaagc agcaagcgcg | 1500 |
| ttacgccgtg ggtcgatgtt tgatgttatg gagcagcaac gatgttacgc agcagggcag | 1560 |
| tcgccctaaa acaaagttaa acatcatgag ggaagcggtg atcgccgaag tatcgactca | 1620 |
| actatcagag gtagttggcg tcatcgagcg ccatctcgaa ccgacgttgc tggccgtaca | 1680 |
| tttgtacggc tccgcagtgg atggcggcct gaagccacac agtgatattg atttgctggt | 1740 |
| tacggtgacc gtaaggcttg atgaaacaac gcggcgagct ttgatcaacg acctttttgga | 1800 |

-continued

```
aacttcggct tccccctggag agagcgagat tctccgcgct gtagaagtca ccattgttgt   1860
gcacgacgac atcattccgt ggcgttatcc agctaagcgc gaactgcaat ttggagaatg   1920
gcagcgcaat gacattcttg caggtatctt cgagccagcc acgatcgaca ttgatctggc   1980
tatcttgctg acaaaagcaa gagaacatag cgttgccttg gtaggtccag cggcggagga   2040
actctttgat ccggttcctg aacaggatct atttgaggcg ctaaatgaaa ccttaacgct   2100
atggaactcg ccgcccgact gggctggcga tgagcgaaat gtagtgctta cgttgtcccg   2160
catttggtac agcgcagtaa ccggcaaaat cgcgccgaag gatgtcgctg ccgactgggc   2220
aatggagcgc ctgccggccc agtatcagcc cgtcatactt gaagctagac aggcttatct   2280
tggacaagaa gaagatcgct tggcctcgcg cgcagatcag ttggaagaat tgtccacta   2340 cgtgaaaggc gagatcacca aggtagtcgg caaataatgt ctaacaattc gttcaagctt   2400
ggctgttttg gcggatgaga gaagattttc agcctgatac agattaaatc agaacgcaga   2460
agcggtctga taaacagaa tttgcctggc ggcagtagcg cggtggtccc acctgacccc   2520
atgccgaact cagaagtgaa acgccgtagc gccgatggta gtgtgggggtc tccccatgcg   2580 agagtaggga actgccaggc atcaaataaa acgaaaggct cagtcgaaag actgggcctt   2640
tcgttttatc tgttgtttgt cggtgaacgc tctcctgagt aggacaaatc cgccgggagc   2700
ggatttgaac gttgcgaagc aacggcccgg agggtggcgg gcaggacgcc cgccataaac   2760
tgccaggcat caaattaagc agaaggccat cctgacggat ggccttttg cgtttctaca   2820 aactcttttg tttattttc taaatacatt caaatatgta tccgctcatg agacaataac   2880
cctgataaat gcttcaataa tattgaaaaa ggaagagtat gagtattcaa catttccgtg   2940
tcgcccttat tcccttttt gcggcatttt gccttcctgt ttttgctcac ccagaaacgc   3000
tggtgaaagt aaaagatgct gaagatcagt tgggtgcacg agtgggttac atcgaactgg   3060
atctcaacag cggtaagatc cttgagagtt ttcgccccga agaacgtttt ccaatgatga   3120 gcactttttaa agttctgcta tgtggcgcgg tattatcccg tgttgacgcc gggcaagagc   3180
aactcggtcg ccgcatacac tattctcaga atgacttggt tgagtactca ccagtcacag   3240
aaaagcatct tacggatggc atgacagtaa gagaattatg cagtgctgcc ataaccatga   3300
gtgataacac tgcggccaac ttacttctga caacgatcgg aggaccgaag gagctaaccg   3360
cttttttgca caacatgggg gatcatgtaa ctcgccttga tcgttgggaa ccggagctga   3420
atgaagccat accaaacgac gagcgtgaca ccacgatgcc tgtagcaatg gcaacaacgt   3480
tgcgcaaact attaactggc gaactactta ctctagcttc ccggcaacaa ttaatagact   3540
ggatggaggc ggataaagtt gcaggaccac ttctgcgctc ggcccttccg gctggctggt   3600
ttattgctga taaatctgga gccggtgagc gtgggtctcg cggtatcatt gcagcactgg   3660
ggccagatgg taagccctcc cgtatcgtag ttatctacac gacggggagt caggcaacta   3720
tggatgaacg aaatagacag atcgctgaga taggtgcctc actgattaag cattggtaac   3780
tgtcagacca agtttactca tatatacttt agattgattt aaaacttcat ttttaattta   3840
aaaggatcta ggtgaagatc ctttttgata atctcatgac caaaatccct aacgtgagt   3900 tttcgttcca ctgagcgtca gaccccgtag aaaagatcaa aggatcttct tgagatcctt   3960
tttttctgcg cgtaatctgc tgcttgcaaa caaaaaaacc accgctacca gcggtggttt   4020
gtttgccgga tcaagagcta ccaactcttt ttccgaaggt aactggcttc agcagagcgc   4080
agataccaaa tactgtcctt ctagtgtagc cgtagttagg ccaccacttc aagaactctg   4140
```

-continued

```
tagcaccgcc tacatacctc gctctgctaa tcctgttacc agtggctgct gccagtggcg    4200
ataagtcgtg tcttaccggg ttggactcaa gacgatagtt accggataag gcgcagcggt    4260
cgggctgaac ggggggttcg tgcacacagc ccagcttgga gcgaacgacc tacaccgaac    4320
tgagatacct acagcgtgag ctatgagaaa gcgccacgct tcccgaaggg agaaaggcgg    4380
acaggtatcc ggtaagcggc agggtcggaa caggagagcg cacgagggag cttccagggg    4440
gaaacgcctg gtatctttat agtcctgtcg ggtttcgcca cctctgactt gagcgtcgat    4500
ttttgtgatg ctcgtcaggg gggcggagcc tatggaaaaa cgccagcaac gcggcctttt    4560
tacggttcct ggccttttgc tggccttttg ctcacatgtt ctttcctgcg ttatcccctg    4620
attctgtgga taaccgtatt accgcctttg agtgagctga taccgctcgc cgcagccgaa    4680
cgaccgagcg cagcgagtca gtgagcgagg aagcggaaga gcgcctgatg cggtattttc    4740
tccttacgca tctgtgcggt atttcacacc gcatatatgg tgcactctca gtacaatctg    4800
ctctgatgcc gcatagttaa gccagtatac actccgctat cgctacgtga ctgggtcatg    4860
gctgcgcccc gacacccgcc aacacccgct gacgcgccct gacgggcttg tctgctcccg    4920
gcatccgctt acagacaagc tgtgaccgtc tccgggagct gcatgtgtca gaggttttca    4980
ccgtcatcac cgaaacgcgc gaggcagcag atcaattcgc gcgcgaaggc gaagcggcat    5040
gcataatgtg cctgtcaaat ggacgaagca gggattctgc aaaccctatg ctactccgtc    5100
aagccgtcaa ttgtctgatt cgttaccaat tatgacaact tgacggctac atcattcact    5160 tttcttcac aaccggcacg gaactcgctc gggctggccc cggtgcattt tttaaatacc    5220
cgcgagaaat agagttgatc gtcaaaacca acattgcgac cgacggtggc gataggcatc    5280
cgggtggtgc tcaaaagcag cttcgcctgg ctgatacgtt ggtcctcgcg ccagcttaag    5340
acgctaatcc ctaactgctg gcggaaaaga tgtgacagac gcgacggcga caagcaaaca    5400
tgctgtgcga cgctggcgat atcaaaattg ctgtctgcca ggtgatcgct gatgtactga    5460
caagcctcgc gtacccgatt atccatcggt ggatggagcg actcgttaat cgcttccatg    5520
cgccgcagta acaattgctc aagcagattt atcgccagca gctccgaata gcgcccttcc    5580
ccttgcccgg cgttaatgat ttgcccaaac aggtcgctga atgcggctg gtgcgcttca    5640 tccgggcgaa agaaccccgt attggcaaat attgacggcc agttaagcca ttcatgccag    5700
taggcgcgcg gacgaaagta aacccactgg tgataccatt cgcgagcctc cggatgacga    5760
ccgtagtgat gaatctctcc tggcgggaac agcaaaatat cacccggtcg gcaaacaaat    5820
tctcgtccct gattttttcac cacccctga ccgcgaatgg tgagattgag aatataacct    5880
ttcattccca gcggtcggtc gataaaaaaa tcgagataac cgttggcctc aatcggcgtt    5940
aaacccgcca ccagatgggc attaaacgag tatcccggca gcagggatc attttgcgct    6000 tcagccatac ttttcatact cccgccattc agag    6034
```

<210> SEQ ID NO 8
<211> LENGTH: 63
<212> TYPE: PRT
<213> ORGANISM: artificial sequence
<220> FEATURE:
<223> OTHER INFORMATION: synthetic construct

<400> SEQUENCE: 8

```
Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
            20                  25                  30
```

Arg Cys Gly Gln Gln Arg Phe Gln Trp Gln Phe Glu Gln Gln Pro Glu
                35                  40                  45

Cys Gly Gln Gln Arg Phe Gln Trp Gln Phe Glu Gln Gln Pro Cys
 50                  55                  60

<210> SEQ ID NO 9
<211> LENGTH: 576
<212> TYPE: DNA
<213> ORGANISM: artificial sequence
<220> FEATURE:
<223> OTHER INFORMATION: synthetic construct

<400> SEQUENCE: 9
gctagctgcg gtcaacaacg ttttcaatgg caattcgaac aacagccgcg ttgcggccag      60
caacgcttcc aatggcagtt tgaacagcaa ccgcgttgcg gtcagcaacg tttccagtgg     120
caatttgaac aacagccaga gtgcggccag cagcgctttc agtggcagtt cgagcagcag     180
ccgtgcggat cttgctgtcc gggctgttgc ggatccgatc catctgctca atctcaactg     240
cctgataaac attctggtct gcatgaacgc gctcctcaac gttacggtcc ggaggaggcg     300
gcgaagaaag aagaggcggc taaaaagccg gctcacatta ataagaccaa cccgcatcag     360
ggcaaccatc actccgaaaa gacccagcgt cagggctccg gtggcggcgg tagcggcagc     420
ggtggcggtg gttctgactc ccatcacaac catcacaagc aggactcccg ccctcagcac     480
cgtaagacgc caaacggcgg tggtgactct caccataacc accacaaaca ggactctcgc     540
ccgcagcacc gcaaaacccc taacggtaaa taataa                               576

<210> SEQ ID NO 10
<211> LENGTH: 191
<212> TYPE: PRT
<213> ORGANISM: artificial sequence
<220> FEATURE:
<223> OTHER INFORMATION: synthetic construct

<400> SEQUENCE: 10

Met Ala Ser Cys Gly Gln Gln Arg Phe Gln Trp Gln Phe Glu Gln Gln
 1               5                  10                  15

Pro Arg Cys Gly Gln Gln Arg Phe Gln Trp Gln Phe Glu Gln Gln Pro
                20                  25                  30

Arg Cys Gly Gln Gln Arg Phe Gln Trp Gln Phe Glu Gln Gln Pro Glu
                35                  40                  45

Cys Gly Gln Gln Arg Phe Gln Trp Gln Phe Glu Gln Gln Pro Cys Gly
 50                  55                  60

Ser Cys Cys Pro Gly Cys Cys Gly Ser Asp Pro Ser Ala Gln Ser Gln
 65                  70                  75                  80

Leu Pro Asp Lys His Ser Gly Leu His Glu Arg Ala Pro Gln Arg Tyr
                85                  90                  95

Gly Pro Glu Glu Ala Ala Lys Lys Glu Ala Ala Lys Lys Pro Ala
                100                 105                 110

His Ile Asn Lys Thr Asn Pro His Gln Gly Asn His His Ser Glu Lys
                115                 120                 125

Thr Gln Arg Gln Gly Ser Gly Gly Gly Gly Ser Gly Ser Gly Gly Gly
            130                 135                 140

Gly Ser Asp Ser His His Asn His His Lys Gln Asp Ser Arg Pro Gln
145                 150                 155                 160

His Arg Lys Thr Pro Asn Gly Gly Gly Asp Ser His His Asn His His
                165                 170                 175

```
Lys Gln Asp Ser Arg Pro Gln His Arg Lys Thr Pro Asn Gly Lys
        180                 185                 190

<210> SEQ ID NO 11
<211> LENGTH: 360
<212> TYPE: DNA
<213> ORGANISM: artificial sequence
<220> FEATURE:
<223> OTHER INFORMATION: synthetic construct

<400> SEQUENCE: 11
gatccatctg ctcaatctca actgcctgat aaacattctg gtctgcatga acgcgctcct     60
caacgttacg gtccggagga ggcggcgaag aaagaagagg cggctaaaaa gccggctcac    120
attaataaga ccaacccgca tcagggcaac catcactccg aaaagaccca gcgtcagggc    180
tccggtggcg gcggtagcgg cagcggtggc ggtggttctg actcccatca caaccatcac    240
aagcaggact cccgccctca gcaccgtaag acgccaaacg gcgtggtgac tctcaccat    300 aaccaccaca acaggactc tcgcccgcag caccgcaaaa ccctaacgg taaataataa    360

<210> SEQ ID NO 12
<211> LENGTH: 118
<212> TYPE: PRT
<213> ORGANISM: artificial sequence
<220> FEATURE:
<223> OTHER INFORMATION: synthetic construct

<400> SEQUENCE: 12

Asp Pro Ser Ala Gln Ser Gln Leu Pro Asp Lys His Ser Gly Leu His
1               5                   10                  15

Glu Arg Ala Pro Gln Arg Tyr Gly Pro Glu Glu Ala Ala Lys Lys Glu
            20                  25                  30

Glu Ala Ala Lys Lys Pro Ala His Ile Asn Lys Thr Asn Pro His Gln
        35                  40                  45

Gly Asn His His Ser Glu Lys Thr Gln Arg Gln Gly Ser Gly Gly Gly
    50                  55                  60

Gly Ser Gly Ser Gly Gly Gly Ser Asp Ser His His Asn His His
65                  70                  75                  80

Lys Gln Asp Ser Arg Pro Gln His Arg Lys Thr Pro Asn Gly Gly
                85                  90                  95

Asp Ser His His Asn His His Lys Gln Asp Ser Arg Pro Gln His Arg
            100                 105                 110

Lys Thr Pro Asn Gly Lys
        115

<210> SEQ ID NO 13
<211> LENGTH: 28
<212> TYPE: DNA
<213> ORGANISM: artificial sequence
<220> FEATURE:
<223> OTHER INFORMATION: primer

<400> SEQUENCE: 13
ctggtccacc tacaacaaag ctctcatc                                         28

<210> SEQ ID NO 14
<211> LENGTH: 34
<212> TYPE: DNA
<213> ORGANISM: artificial sequence
<220> FEATURE:
<223> OTHER INFORMATION: primer
```

<400> SEQUENCE: 14

```
cttgtgcaat gtaacatcag agattttgag acac                                    34
```

<210> SEQ ID NO 15
<211> LENGTH: 918
<212> TYPE: DNA
<213> ORGANISM: Escherichia coli

<400> SEQUENCE: 15

```
atgtctaaac gattaccacc gctaaatgcc ttacgagttt ttgatgccgc agcacgccat         60
ttaagtttca ctcgcgcagc agaagagctt tttgtgaccc aagccgcagt aagtcatcaa        120
atcaagtctc ttgaggattt tttggggcta aaactgttcc gccgccgtaa tcgttcactc        180
ctgctgaccg aggaagggca agctatttc ctcgatatca aagagatatt ttcgcaatta         240
accgaagcga cgcgtaaact ccaggcccgt agcgccaagg gggcgttgac ggtcagttta        300
ctccccagtt tcgccattca ttggttggtt ccgcgacttt ccagctttaa ttcagcttat        360
ccgggaattg acgttcgaat ccaggcggtt gatcgtcagg aagataagct ggcggatgat        420
gttgatgtgg cgatatttta tggtcggggc aactggccgg gctacgggt ggaaaaactg        480
tacgccgaat atttattgcc ggtgtgttcg ccgctactgc tgactggcga aaaccccttg        540
aagacaccgg aagatctggc taaacatacg ttattacatg atgcttcgcg ccgtgactgg        600
cagacatata cccgacagtt ggggttaaat catatcaacg ttcagcaagg gccaattttt        660
agccatagcg ccatggtgct gcaagcggct atccacgggc agggagtggc gctggcaaat        720
aacgtgatgg cgcaatctga atcgaggcc ggacgtcttg tttgcccgtt taatgatgtt         780
ctggtcagta aaaatgcttt ttatctggtt tgtcatgaca gtcaggcaga actgggtaaa        840
atagccgcct ttcgccaatg gatcctggcg aaagccgctg ctgaacaaga aaaattccgc        900
tttcgttatg aacaataa                                                      918
```

<210> SEQ ID NO 16
<211> LENGTH: 305
<212> TYPE: PRT
<213> ORGANISM: Escherichia coli

<400> SEQUENCE: 16

```
Met Ser Lys Arg Leu Pro Pro Leu Asn Ala Leu Arg Val Phe Asp Ala
1               5                   10                  15

Ala Ala Arg His Leu Ser Phe Thr Arg Ala Ala Glu Glu Leu Phe Val
            20                  25                  30

Thr Gln Ala Ala Val Ser His Gln Ile Lys Ser Leu Glu Asp Phe Leu
        35                  40                  45

Gly Leu Lys Leu Phe Arg Arg Arg Asn Arg Ser Leu Leu Leu Thr Glu
    50                  55                  60

Glu Gly Gln Ser Tyr Phe Leu Asp Ile Lys Glu Ile Phe Ser Gln Leu
65                  70                  75                  80

Thr Glu Ala Thr Arg Lys Leu Gln Ala Arg Ser Ala Lys Gly Ala Leu
                85                  90                  95

Thr Val Ser Leu Leu Pro Ser Phe Ala Ile His Trp Leu Val Pro Arg
            100                 105                 110

Leu Ser Ser Phe Asn Ser Ala Tyr Pro Gly Ile Asp Val Arg Ile Gln
        115                 120                 125

Ala Val Asp Arg Gln Glu Asp Lys Leu Ala Asp Val Asp Val Ala
    130                 135                 140
```

```
Ile Phe Tyr Gly Arg Gly Asn Trp Pro Gly Leu Arg Val Glu Lys Leu
145                 150                 155                 160

Tyr Ala Glu Tyr Leu Leu Pro Val Cys Ser Pro Leu Leu Thr Gly
            165                 170                 175

Glu Lys Pro Leu Lys Thr Pro Glu Asp Leu Ala Lys His Thr Leu Leu
            180                 185                 190

His Asp Ala Ser Arg Arg Asp Trp Gln Thr Tyr Thr Arg Gln Leu Gly
            195                 200                 205

Leu Asn His Ile Asn Val Gln Gln Gly Pro Ile Phe Ser His Ser Ala
            210                 215                 220

Met Val Leu Gln Ala Ala Ile His Gly Gln Gly Val Ala Leu Ala Asn
225                 230                 235                 240

Asn Val Met Ala Gln Ser Glu Ile Glu Ala Gly Arg Leu Val Cys Pro
                245                 250                 255

Phe Asn Asp Val Leu Val Ser Lys Asn Ala Phe Tyr Leu Val Cys His
            260                 265                 270

Asp Ser Gln Ala Glu Leu Gly Lys Ile Ala Ala Phe Arg Gln Trp Ile
            275                 280                 285

Leu Ala Lys Ala Ala Ala Glu Gln Glu Lys Phe Arg Phe Arg Tyr Glu
    290                 295                 300

Gln
305

<210> SEQ ID NO 17
<211> LENGTH: 567
<212> TYPE: DNA
<213> ORGANISM: Escherichia coli

<400> SEQUENCE: 17
atggtcaaat ctcaaccgat tttgagatat atcttgcgcg ggattcccgc gattgcagta    60
gcggttctgc tttctgcatg tagtgcaaat aacaccgcaa agaatatgca tcctgagaca   120
cgtgcagtgg gtagtgaaac atcatcactg caagcttctc aggatgaatt tgaaaacctg   180
gttcgtaatg tcgacgtaaa atcgcgaatt atggatcagt atgctgactg gaaaggcgta   240
cgttatcgtc tgggcggcag cactaaaaaa ggtatcgatt gttctggttt cgtacagcgt   300
acattccgtg agcaatttgg cttagaactt ccgcgttcga cttacgaaca gcaggaaatg   360
ggtaaatctg tttcccgcag taatttgcgt acgggtgatt tagttctgtt ccgtgccggt   420
tcaacgggac gccatgtcgg tatttatatc ggcaacaatc agtttgtcca tgcttccacc   480
agcagtggtg ttattatttc cagcatgaat gaaccgtact ggaagaagcg ttacaacgaa   540
gcacgccggg ttctcagccg cagctaa                                       567

<210> SEQ ID NO 18
<211> LENGTH: 188
<212> TYPE: PRT
<213> ORGANISM: Escherichia coli

<400> SEQUENCE: 18

Met Val Lys Ser Gln Pro Ile Leu Arg Tyr Ile Leu Arg Gly Ile Pro
1               5                   10                  15

Ala Ile Ala Val Ala Val Leu Leu Ser Ala Cys Ser Ala Asn Asn Thr
            20                  25                  30

Ala Lys Asn Met His Pro Glu Thr Arg Ala Val Gly Ser Glu Thr Ser
        35                  40                  45
```

```
Ser Leu Gln Ala Ser Gln Asp Glu Phe Glu Asn Leu Val Arg Asn Val
     50                  55                  60

Asp Val Lys Ser Arg Ile Met Asp Gln Tyr Ala Asp Trp Lys Gly Val
 65                  70                  75                  80

Arg Tyr Arg Leu Gly Gly Ser Thr Lys Lys Gly Ile Asp Cys Ser Gly
                 85                  90                  95

Phe Val Gln Arg Thr Phe Arg Glu Gln Phe Gly Leu Glu Leu Pro Arg
                100                 105                 110

Ser Thr Tyr Glu Gln Gln Glu Met Gly Lys Ser Val Ser Arg Ser Asn
            115                 120                 125

Leu Arg Thr Gly Asp Leu Val Leu Phe Arg Ala Gly Ser Thr Gly Arg
    130                 135                 140

His Val Gly Ile Tyr Ile Gly Asn Asn Gln Phe Val His Ala Ser Thr
145                 150                 155                 160

Ser Ser Gly Val Ile Ile Ser Ser Met Asn Glu Pro Tyr Trp Lys Lys
                165                 170                 175

Arg Tyr Asn Glu Ala Arg Arg Val Leu Ser Arg Ser
            180                 185

<210> SEQ ID NO 19
<211> LENGTH: 16
<212> TYPE: PRT
<213> ORGANISM: artificial sequence
<220> FEATURE:
<223> OTHER INFORMATION: synthetic construct peptide linker

<400> SEQUENCE: 19

Gly Pro Glu Glu Ala Ala Lys Lys Glu Glu Ala Ala Lys Lys Pro Ala
 1               5                  10                  15

<210> SEQ ID NO 20
<211> LENGTH: 100
<212> TYPE: DNA
<213> ORGANISM: Escherichia coli

<400> SEQUENCE: 20
tttttatcca taagattagc ggatcctacc tgacgctttt tatcgcaact ctctactgtt      60
tctccatacc cgttttttgg gctaacagga ggaattaacc                           100

<210> SEQ ID NO 21
<211> LENGTH: 591
<212> TYPE: DNA
<213> ORGANISM: Escherichia coli

<400> SEQUENCE: 21
atgaaagtag caaaagacct ggtggtcagc ctggcctatc aggtacgtac agaagacggt      60
gtgttggttg atgagtctcc ggtgagtgcg ccgctggact acctgcatgg tcacggttcc     120
ctgatctctg gcctggaaac ggcgctggaa ggtcatgaag ttggcgacaa atttgatgtc     180
gctgttggcg cgaacgacgc ttacggtcag tacgacgaaa acctggtgca acgtgttcct     240
aaagacgtat ttatgggcgt tgatgaactg caggtaggta tgcgtttcct ggctgaaacc     300
gaccagggtc cggtaccggt tgaaatcact gcggttgaag acgatcacgt cgtggttgat     360
ggtaaccaca tgctggccgg tcagaacctg aaattcaacg ttgaagttgt ggcgattcgc     420
gaagcgactg aagaagaact ggctcatggt cacgttcacg cgcgcacga tcaccaccac      480 gatcacgacc acgacggttg ctgcggcggt catggccacg atcacggtca tgaacacggt     540
ggcgaaggct gctgtggcgg taaaggcaac ggcggttgcg gttgccacta a             591
```

```
<210> SEQ ID NO 22
<211> LENGTH: 196
<212> TYPE: PRT
<213> ORGANISM: Escherichia coli

<400> SEQUENCE: 22

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Cys Cys Gly His Gly His Asp His His Gly
                165                 170                 175

His Glu His Gly Gly Glu Gly Cys Cys Gly Gly Lys Gly Asn Gly Gly
            180                 185                 190

Cys Gly Cys His
        195

<210> SEQ ID NO 23
<211> LENGTH: 8
<212> TYPE: PRT
<213> ORGANISM: Artificial Sequence
<220> FEATURE:
<223> OTHER INFORMATION: Caspase 3 cleavage site

<400> SEQUENCE: 23

Leu Glu Ser Gly Asp Glu Val Asp
1               5

<210> SEQ ID NO 24
<211> LENGTH: 12
<212> TYPE: PRT
<213> ORGANISM: artificial sequence
<220> FEATURE:
<223> OTHER INFORMATION: Synthetic construct

<400> SEQUENCE: 24

Arg Val Pro Asn Lys Thr Val Thr Val Asp Gly Ala
1               5                   10

<210> SEQ ID NO 25
<211> LENGTH: 12
<212> TYPE: PRT
<213> ORGANISM: artificial sequence
```

```
<220> FEATURE:
<223> OTHER INFORMATION: Synthetic construct

<400> SEQUENCE: 25

Asp Arg His Lys Ser Lys Tyr Ser Ser Thr Lys Ser
1               5                   10

<210> SEQ ID NO 26
<211> LENGTH: 12
<212> TYPE: PRT
<213> ORGANISM: artificial sequence
<220> FEATURE:
<223> OTHER INFORMATION: Synthetic construct

<400> SEQUENCE: 26

Lys Asn Phe Pro Gln Gln Lys Glu Phe Pro Leu Ser
1               5                   10

<210> SEQ ID NO 27
<211> LENGTH: 12
<212> TYPE: PRT
<213> ORGANISM: artificial sequence
<220> FEATURE:
<223> OTHER INFORMATION: Synthetic construct

<400> SEQUENCE: 27

Gln Arg Asn Ser Pro Pro Ala Met Ser Arg Arg Asp
1               5                   10

<210> SEQ ID NO 28
<211> LENGTH: 12
<212> TYPE: PRT
<213> ORGANISM: artificial sequence
<220> FEATURE:
<223> OTHER INFORMATION: Synthetic construct

<400> SEQUENCE: 28

Thr Arg Lys Pro Asn Met Pro His Gly Gln Tyr Leu
1               5                   10

<210> SEQ ID NO 29
<211> LENGTH: 12
<212> TYPE: PRT
<213> ORGANISM: artificial sequence
<220> FEATURE:
<223> OTHER INFORMATION: Synthetic construct

<400> SEQUENCE: 29

Lys Pro Pro His Leu Ala Lys Leu Pro Phe Thr Thr
1               5                   10

<210> SEQ ID NO 30
<211> LENGTH: 12
<212> TYPE: PRT
<213> ORGANISM: artificial sequence
<220> FEATURE:
<223> OTHER INFORMATION: Synthetic construct

<400> SEQUENCE: 30

Asn Lys Arg Pro Pro Thr Ser His Arg Ile His Ala
1               5                   10

<210> SEQ ID NO 31
<211> LENGTH: 12
<212> TYPE: PRT
<213> ORGANISM: artificial sequence
<220> FEATURE:
```

<223> OTHER INFORMATION: Synthetic construct

<400> SEQUENCE: 31

Asn Leu Pro Arg Tyr Gln Pro Pro Cys Lys Pro Leu
1               5                   10

<210> SEQ ID NO 32
<211> LENGTH: 12
<212> TYPE: PRT
<213> ORGANISM: artificial sequence
<220> FEATURE:
<223> OTHER INFORMATION: Synthetic construct

<400> SEQUENCE: 32

Arg Pro Pro Trp Lys Lys Pro Ile Pro Pro Ser Glu
1               5                   10

<210> SEQ ID NO 33
<211> LENGTH: 12
<212> TYPE: PRT
<213> ORGANISM: artificial sequence
<220> FEATURE:
<223> OTHER INFORMATION: Synthetic construct

<400> SEQUENCE: 33

Arg Gln Arg Pro Lys Asp His Phe Phe Ser Arg Pro
1               5                   10

<210> SEQ ID NO 34
<211> LENGTH: 12
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa = Thr or Pro
<220> FEATURE:
<221> NAME/KEY: MISC_FEATURE
<222> LOCATION: (12)..(12)
<223> OTHER INFORMATION: Xaa = Thr or Pro

<400> SEQUENCE: 34

Ser Val Pro Asn Lys Xaa Val Thr Val Asp Gly Xaa
1               5                   10

<210> SEQ ID NO 35
<211> LENGTH: 12
<212> TYPE: PRT
<213> ORGANISM: artificial sequence
<220> FEATURE:
<223> OTHER INFORMATION: Synthetic construct

<400> SEQUENCE: 35

Thr Thr Lys Trp Arg His Arg Ala Pro Val Ser Pro
1               5                   10

<210> SEQ ID NO 36
<211> LENGTH: 12
<212> TYPE: PRT
<213> ORGANISM: artificial sequence
<220> FEATURE:
<223> OTHER INFORMATION: Synthetic construct

<400> SEQUENCE: 36

Trp Leu Gly Lys Asn Arg Ile Lys Pro Arg Ala Ser
1               5                   10

<210> SEQ ID NO 37
<211> LENGTH: 12
<212> TYPE: PRT
<213> ORGANISM: artificial sequence
<220> FEATURE:
<223> OTHER INFORMATION: Synthetic construct

<400> SEQUENCE: 37

Ser Asn Phe Lys Thr Pro Leu Pro Leu Thr Gln Ser
1               5                   10

<210> SEQ ID NO 38
<211> LENGTH: 12
<212> TYPE: PRT
<213> ORGANISM: artificial sequence
<220> FEATURE:
<223> OTHER INFORMATION: Synthetic construct

<400> SEQUENCE: 38

Ser Val Ser Val Gly Met Lys Pro Ser Pro Arg Pro
1               5                   10

<210> SEQ ID NO 39
<211> LENGTH: 7
<212> TYPE: PRT
<213> ORGANISM: artificial sequence
<220> FEATURE:
<223> OTHER INFORMATION: Synthetic construct

<400> SEQUENCE: 39

Asp Leu His Thr Val Tyr His
1               5

4
<210> SEQ ID NO 40
<211> LENGTH: 7
<212> TYPE: PRT
<213> ORGANISM: artificial sequence
<220> FEATURE:
<223> OTHER INFORMATION: Synthetic construct

<400> SEQUENCE: 40

His Ile Lys Pro Pro Thr Arg
1               5

<210> SEQ ID NO 41
<211> LENGTH: 7
<212> TYPE: PRT
<213> ORGANISM: artificial sequence
<220> FEATURE:
<223> OTHER INFORMATION: Synthetic construct

<400> SEQUENCE: 41

His Pro Val Trp Pro Ala Ile
1               5

<210> SEQ ID NO 42
<211> LENGTH: 7
<212> TYPE: PRT
<213> ORGANISM: artificial sequence
<220> FEATURE:
<223> OTHER INFORMATION: Synthetic construct

<400> SEQUENCE: 42

Met Pro Leu Tyr Tyr Leu Gln
1               5

```
<210> SEQ ID NO 43
<211> LENGTH: 26
<212> TYPE: PRT
<213> ORGANISM: artificial sequence
<220> FEATURE:
<223> OTHER INFORMATION: Synthetic construct

<400> SEQUENCE: 43

His Leu Thr Val Pro Trp Arg Gly Gly Gly Ser Ala Val Pro Phe Tyr
1               5                   10                  15

Ser His Ser Gln Ile Thr Leu Pro Asn His
            20                  25

<210> SEQ ID NO 44
<211> LENGTH: 41
<212> TYPE: PRT
<213> ORGANISM: artificial sequence
<220> FEATURE:
<223> OTHER INFORMATION: Synthetic construct

<400> SEQUENCE: 44

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
            35                  40

<210> SEQ ID NO 45
<211> LENGTH: 7
<212> TYPE: PRT
<213> ORGANISM: artificial sequence
<220> FEATURE:
<223> OTHER INFORMATION: Synthetic construct

<400> SEQUENCE: 45

Lys His Pro Thr Tyr Arg Gln
1               5

<210> SEQ ID NO 46
<211> LENGTH: 7
<212> TYPE: PRT
<213> ORGANISM: artificial sequence
<220> FEATURE:
<223> OTHER INFORMATION: Synthetic construct

<400> SEQUENCE: 46

His Pro Met Ser Ala Pro Arg
1               5

<210> SEQ ID NO 47
<211> LENGTH: 7
<212> TYPE: PRT
<213> ORGANISM: artificial sequence
<220> FEATURE:
<223> OTHER INFORMATION: Synthetic construct

<400> SEQUENCE: 47

Met Pro Lys Tyr Tyr Leu Gln
1               5

<210> SEQ ID NO 48
<211> LENGTH: 7
<212> TYPE: PRT
<213> ORGANISM: artificial sequence
```

-continued

```
<220> FEATURE:
<223> OTHER INFORMATION: Synthetic construct

<400> SEQUENCE: 48

Met His Ala His Ser Ile Ala
1               5

<210> SEQ ID NO 49
<211> LENGTH: 12
<212> TYPE: PRT
<213> ORGANISM: artificial sequence
<220> FEATURE:
<223> OTHER INFORMATION: Synthetic construct

<400> SEQUENCE: 49

Ala Lys Pro Ile Ser Gln His Leu Gln Arg Gly Ser
1               5                   10

<210> SEQ ID NO 50
<211> LENGTH: 12
<212> TYPE: PRT
<213> ORGANISM: artificial sequence
<220> FEATURE:
<223> OTHER INFORMATION: Synthetic construct

<400> SEQUENCE: 50

Ala Pro Pro Thr Pro Ala Ala Ala Ser Ala Thr Thr
1               5                   10

<210> SEQ ID NO 51
<211> LENGTH: 12
<212> TYPE: PRT
<213> ORGANISM: artificial sequence
<220> FEATURE:
<223> OTHER INFORMATION: Synthetic construct

<400> SEQUENCE: 51

Asp Pro Thr Glu Gly Ala Arg Arg Thr Ile Met Thr
1               5                   10

<210> SEQ ID NO 52
<211> LENGTH: 12
<212> TYPE: PRT
<213> ORGANISM: artificial sequence
<220> FEATURE:
<223> OTHER INFORMATION: Synthetic construct

<400> SEQUENCE: 52

Leu Asp Thr Ser Phe Pro Pro Val Pro Phe His Ala
1               5                   10

<210> SEQ ID NO 53
<211> LENGTH: 12
<212> TYPE: PRT
<213> ORGANISM: artificial sequence
<220> FEATURE:
<223> OTHER INFORMATION: Synthetic construct

<400> SEQUENCE: 53

Leu Asp Thr Ser Phe His Gln Val Pro Phe His Gln
1               5                   10

<210> SEQ ID NO 54
<211> LENGTH: 11
<212> TYPE: PRT
<213> ORGANISM: artificial sequence
<220> FEATURE:
```

<223> OTHER INFORMATION: Synthetic construct

<400> SEQUENCE: 54

Leu Pro Arg Ile Ala Asn Thr Trp Ser Pro Ser
1               5                   10

<210> SEQ ID NO 55
<211> LENGTH: 12
<212> TYPE: PRT
<213> ORGANISM: artificial sequence
<220> FEATURE:
<223> OTHER INFORMATION: Synthetic construct

<400> SEQUENCE: 55

Arg Thr Asn Ala Ala Asp His Pro Ala Ala Val Thr
1               5                   10

<210> SEQ ID NO 56
<211> LENGTH: 12
<212> TYPE: PRT
<213> ORGANISM: artificial sequence
<220> FEATURE:
<223> OTHER INFORMATION: Synthetic construct

<400> SEQUENCE: 56

Ser Leu Asn Trp Val Thr Ile Pro Gly Pro Lys Ile
1               5                   10

<210> SEQ ID NO 57
<211> LENGTH: 12
<212> TYPE: PRT
<213> ORGANISM: artificial sequence
<220> FEATURE:
<223> OTHER INFORMATION: Synthetic construct

<400> SEQUENCE: 57

Thr Asp Met Gln Ala Pro Thr Lys Ser Tyr Ser Asn
1               5                   10

<210> SEQ ID NO 58
<211> LENGTH: 12
<212> TYPE: PRT
<213> ORGANISM: artificial sequence
<220> FEATURE:
<223> OTHER INFORMATION: Synthetic construct

<400> SEQUENCE: 58

Thr Ile Met Thr Lys Ser Pro Ser Leu Ser Cys Gly
1               5                   10

<210> SEQ ID NO 59
<211> LENGTH: 12
<212> TYPE: PRT
<213> ORGANISM: artificial sequence
<220> FEATURE:
<223> OTHER INFORMATION: Synthetic construct

<400> SEQUENCE: 59

Thr Pro Ala Leu Asp Gly Leu Arg Gln Pro Leu Arg
1               5                   10

<210> SEQ ID NO 60
<211> LENGTH: 12
<212> TYPE: PRT
<213> ORGANISM: artificial sequence
<220> FEATURE:
<223> OTHER INFORMATION: Synthetic construct -continued

```
<400> SEQUENCE: 60

Thr Tyr Pro Ala Ser Arg Leu Pro Leu Leu Ala Pro
1               5                   10

<210> SEQ ID NO 61
<211> LENGTH: 12
<212> TYPE: PRT
<213> ORGANISM: artificial sequence
<220> FEATURE:
<223> OTHER INFORMATION: Synthetic construct

<400> SEQUENCE: 61

Ala Lys Thr His Lys His Pro Ala Pro Ser Tyr Ser
1               5                   10

<210> SEQ ID NO 62
<211> LENGTH: 12
<212> TYPE: PRT
<213> ORGANISM: artificial sequence
<220> FEATURE:
<223> OTHER INFORMATION: Synthetic construct

<400> SEQUENCE: 62

Thr Asp Pro Thr Pro Phe Ser Ile Ser Pro Glu Arg
1               5                   10

<210> SEQ ID NO 63
<211> LENGTH: 12
<212> TYPE: PRT
<213> ORGANISM: artificial sequence
<220> FEATURE:
<223> OTHER INFORMATION: Synthetic construct

<400> SEQUENCE: 63

Ser Gln Asn Trp Gln Asp Ser Thr Ser Tyr Ser Asn
1               5                   10

<210> SEQ ID NO 64
<211> LENGTH: 12
<212> TYPE: PRT
<213> ORGANISM: artificial sequence
<220> FEATURE:
<223> OTHER INFORMATION: Synthetic construct

<400> SEQUENCE: 64

Trp His Asp Lys Pro Gln Asn Ser Ser Lys Ser Thr
1               5                   10

<210> SEQ ID NO 65
<211> LENGTH: 12
<212> TYPE: PRT
<213> ORGANISM: artificial sequence
<220> FEATURE:
<223> OTHER INFORMATION: Synthetic construct

<400> SEQUENCE: 65

Leu Asp Val Glu Ser Tyr Lys Gly Thr Ser Met Pro
1               5                   10

<210> SEQ ID NO 66
<211> LENGTH: 7
<212> TYPE: PRT
<213> ORGANISM: artificial sequence
<220> FEATURE:
<223> OTHER INFORMATION: Synthetic construct
```

```
<400> SEQUENCE: 66

Asn Thr Pro Lys Glu Asn Trp
1               5

<210> SEQ ID NO 67
<211> LENGTH: 7
<212> TYPE: PRT
<213> ORGANISM: artificial sequence
<220> FEATURE:
<223> OTHER INFORMATION: Synthetic construct

<400> SEQUENCE: 67

Asn Thr Pro Ala Ser Asn Arg
1               5

<210> SEQ ID NO 68
<211> LENGTH: 7
<212> TYPE: PRT
<213> ORGANISM: artificial sequence
<220> FEATURE:
<223> OTHER INFORMATION: Synthetic construct

<400> SEQUENCE: 68

Pro Arg Gly Met Leu Ser Thr
1               5

<210> SEQ ID NO 69
<211> LENGTH: 7
<212> TYPE: PRT
<213> ORGANISM: artificial sequence
<220> FEATURE:
<223> OTHER INFORMATION: Synthetic construct

<400> SEQUENCE: 69

Pro Pro Thr Tyr Leu Ser Thr
1               5

<210> SEQ ID NO 70
<211> LENGTH: 12
<212> TYPE: PRT
<213> ORGANISM: artificial sequence
<220> FEATURE:
<223> OTHER INFORMATION: Synthetic construct

<400> SEQUENCE: 70

Thr Ile Pro Thr His Arg Gln His Asp Tyr Arg Ser
1               5                   10

<210> SEQ ID NO 71
<211> LENGTH: 7
<212> TYPE: PRT
<213> ORGANISM: artificial sequence
<220> FEATURE:
<223> OTHER INFORMATION: Synthetic construct

<400> SEQUENCE: 71

Thr Pro Pro Thr His Arg Leu
1               5

<210> SEQ ID NO 72
<211> LENGTH: 7
<212> TYPE: PRT
<213> ORGANISM: artificial sequence
<220> FEATURE:
<223> OTHER INFORMATION: Synthetic construct

<400> SEQUENCE: 72
```

```
Leu Pro Thr Met Ser Thr Pro
1               5

<210> SEQ ID NO 73
<211> LENGTH: 7
<212> TYPE: PRT
<213> ORGANISM: artificial sequence
<220> FEATURE:
<223> OTHER INFORMATION: Synthetic construct

<400> SEQUENCE: 73

Leu Gly Thr Asn Ser Thr Pro
1               5

<210> SEQ ID NO 74
<211> LENGTH: 12
<212> TYPE: PRT
<213> ORGANISM: artificial sequence
<220> FEATURE:
<223> OTHER INFORMATION: Synthetic construct

<400> SEQUENCE: 74

Thr Pro Leu Thr Gly Ser Thr Asn Leu Leu Ser Ser
1               5                   10

<210> SEQ ID NO 75
<211> LENGTH: 7
<212> TYPE: PRT
<213> ORGANISM: artificial sequence
<220> FEATURE:
<223> OTHER INFORMATION: Synthetic construct

<400> SEQUENCE: 75

Thr Pro Leu Thr Lys Glu Thr
1               5

<210> SEQ ID NO 76
<211> LENGTH: 7
<212> TYPE: PRT
<213> ORGANISM: artificial sequence
<220> FEATURE:
<223> OTHER INFORMATION: Synthetic construct

<400> SEQUENCE: 76

Lys Gln Ser His Asn Pro Pro
1               5

<210> SEQ ID NO 77
<211> LENGTH: 7
<212> TYPE: PRT
<213> ORGANISM: artificial sequence
<220> FEATURE:
<223> OTHER INFORMATION: Synthetic construct

<400> SEQUENCE: 77

Gln Gln Ser His Asn Pro Pro
1               5

<210> SEQ ID NO 78
<211> LENGTH: 7
<212> TYPE: PRT
<213> ORGANISM: artificial sequence
<220> FEATURE:
<223> OTHER INFORMATION: Synthetic construct

<400> SEQUENCE: 78
```

```
Thr Gln Pro His Asn Pro Pro
1               5

<210> SEQ ID NO 79
<211> LENGTH: 12
<212> TYPE: PRT
<213> ORGANISM: artificial sequence
<220> FEATURE:
<223> OTHER INFORMATION: Synthetic construct

<400> SEQUENCE: 79

Ser Thr Asn Leu Leu Arg Thr Ser Thr Val His Pro
1               5                   10

<210> SEQ ID NO 80
<211> LENGTH: 12
<212> TYPE: PRT
<213> ORGANISM: artificial sequence
<220> FEATURE:
<223> OTHER INFORMATION: Synthetic construct

<400> SEQUENCE: 80

His Thr Gln Pro Ser Tyr Ser Ser Thr Asn Leu Phe
1               5                   10

<210> SEQ ID NO 81
<211> LENGTH: 7
<212> TYPE: PRT
<213> ORGANISM: artificial sequence
<220> FEATURE:
<223> OTHER INFORMATION: Synthetic construct

<400> SEQUENCE: 81

Ser Leu Leu Ser Ser His Ala
1               5

<210> SEQ ID NO 82
<211> LENGTH: 12
<212> TYPE: PRT
<213> ORGANISM: artificial sequence
<220> FEATURE:
<223> OTHER INFORMATION: Synthetic construct

<400> SEQUENCE: 82

Gln Gln Ser Ser Ile Ser Leu Ser Ser His Ala Val
1               5                   10

<210> SEQ ID NO 83
<211> LENGTH: 7
<212> TYPE: PRT
<213> ORGANISM: artificial sequence
<220> FEATURE:
<223> OTHER INFORMATION: Synthetic construct

<400> SEQUENCE: 83

Asn Ala Ser Pro Ser Ser Leu
1               5

<210> SEQ ID NO 84
<211> LENGTH: 7
<212> TYPE: PRT
<213> ORGANISM: artificial sequence
<220> FEATURE:
<223> OTHER INFORMATION: Synthetic construct

<400> SEQUENCE: 84

His Ser Pro Ser Ser Leu Arg
```

```
1               5

<210> SEQ ID NO 85
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= H, R or N
<220> FEATURE:
<221> NAME/KEY: MISC_FEATURE
<222> LOCATION: (2)..(2)
<223> OTHER INFORMATION: X= His, Arg or Asn

<400> SEQUENCE: 85

Lys Xaa Ser His His Thr His
1               5

<210> SEQ ID NO 86
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X = H, R or N
<220> FEATURE:
<221> NAME/KEY: MISC_FEATURE
<222> LOCATION: (2)..(2)
<223> OTHER INFORMATION: X = His, Arg or Asn

<400> SEQUENCE: 86

Glu Xaa Ser His His Thr His
1               5

<210> SEQ ID NO 87
<211> LENGTH: 12
<212> TYPE: PRT
<213> ORGANISM: artificial sequence
<220> FEATURE:
<223> OTHER INFORMATION: Synthetic construct

<400> SEQUENCE: 87

Ser His His Thr His Tyr Gly Gln Pro Gly Pro Val
1               5                   10

<210> SEQ ID NO 88
<211> LENGTH: 7
<212> TYPE: PRT
<213> ORGANISM: artificial sequence
<220> FEATURE:
<223> OTHER INFORMATION: Synthetic construct

<400> SEQUENCE: 88

Leu Glu Ser Thr Ser Leu Leu
1               5

<210> SEQ ID NO 89
<211> LENGTH: 7
<212> TYPE: PRT
<213> ORGANISM: artificial sequence
<220> FEATURE:
<223> OTHER INFORMATION: Synthetic construct

<400> SEQUENCE: 89
```

```
Asp Leu Thr Leu Pro Phe His
1               5

<210> SEQ ID NO 90
<211> LENGTH: 8
<212> TYPE: PRT
<213> ORGANISM: artificial sequence
<220> FEATURE:
<223> OTHER INFORMATION: Synthetic construct

<400> SEQUENCE: 90

Arg Thr Asn Ala Ala Asp His Pro
1               5

<210> SEQ ID NO 91
<211> LENGTH: 12
<212> TYPE: PRT
<213> ORGANISM: artificial sequence
<220> FEATURE:
<223> OTHER INFORMATION: Synthetic construct

<400> SEQUENCE: 91

Ile Pro Trp Trp Asn Ile Arg Ala Pro Leu Asn Ala
1               5                   10

<210> SEQ ID NO 92
<211> LENGTH: 18
<212> TYPE: PRT
<213> ORGANISM: artificial sequence
<220> FEATURE:
<223> OTHER INFORMATION: Synthetic construct

<400> SEQUENCE: 92

Glu Gln Ile Ser Gly Ser Leu Val Ala Ala Pro Trp Glu Gly Glu Gly
1               5                   10                  15

Glu Arg

<210> SEQ ID NO 93
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 93

Thr Pro Pro Glu Leu Leu His Gly Ala Pro Arg Ser
1               5                   10

<210> SEQ ID NO 94
<211> LENGTH: 18
<212> TYPE: PRT
<213> ORGANISM: artificial sequence
<220> FEATURE:
<223> OTHER INFORMATION: Synthetic construct

<400> SEQUENCE: 94

Leu Asp Thr Ser Phe His Gln Val Pro Phe His Gln Lys Arg Lys Arg
1               5                   10                  15

Lys Asp

<210> SEQ ID NO 95
<211> LENGTH: 18
<212> TYPE: PRT
<213> ORGANISM: artificial sequence
<220> FEATURE:
```

```
<223> OTHER INFORMATION: Synthetic construct

<400> SEQUENCE: 95

Glu Gln Ile Ser Gly Ser Leu Val Ala Ala Pro Trp Lys Arg Lys Arg
1               5                   10                  15

Lys Asp

<210> SEQ ID NO 96
<211> LENGTH: 18
<212> TYPE: PRT
<213> ORGANISM: artificial sequence
<220> FEATURE:
<223> OTHER INFORMATION: Synthetic construct

<400> SEQUENCE: 96

Thr Pro Pro Glu Leu Leu His Gly Asp Pro Arg Ser Lys Arg Lys Arg
1               5                   10                  15

Lys Asp

<210> SEQ ID NO 97
<211> LENGTH: 13
<212> TYPE: PRT
<213> ORGANISM: artificial sequence
<220> FEATURE:
<223> OTHER INFORMATION: Synthetic construct

<400> SEQUENCE: 97

Asn Thr Ser Gln Leu Ser Thr Glu Gly Glu Gly Glu Asp
1               5                   10

<210> SEQ ID NO 98
<211> LENGTH: 13
<212> TYPE: PRT
<213> ORGANISM: artificial sequence
<220> FEATURE:
<223> OTHER INFORMATION: Synthetic construct

<400> SEQUENCE: 98

Thr Pro Pro Glu Leu Leu His Gly Asp Pro Arg Ser Cys
1               5                   10

<210> SEQ ID NO 99
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 99

His Ile Asn Lys Thr Asn Pro His Gln Gly Asn His His Ser Glu Lys
1               5                   10                  15

Thr Gln Arg Gln
            20

<210> SEQ ID NO 100
<211> LENGTH: 15
<212> TYPE: PRT
<213> ORGANISM: artificial sequence
<220> FEATURE:
<223> OTHER INFORMATION: Synthetic construct

<400> SEQUENCE: 100

His Ala His Lys Asn Gln Lys Glu Thr His Gln Arg His Ala Ala
1               5                   10                  15
```

```
<210> SEQ ID NO 101
<211> LENGTH: 15
<212> TYPE: PRT
<213> ORGANISM: artificial sequence
<220> FEATURE:
<223> OTHER INFORMATION: Synthetic construct

<400> SEQUENCE: 101

His Glu His Lys Asn Gln Lys Glu Thr His Gln Arg His Ala Ala
1               5                   10                  15

<210> SEQ ID NO 102
<211> LENGTH: 20
<212> TYPE: PRT
<213> ORGANISM: artificial sequence
<220> FEATURE:
<223> OTHER INFORMATION: Synthetic construct

<400> SEQUENCE: 102

His Asn His Met Gln Glu Arg Tyr Thr Glu Pro Gln His Ser Pro Ser
1               5                   10                  15

Val Asn Gly Leu
            20

<210> SEQ ID NO 103
<211> LENGTH: 17
<212> TYPE: PRT
<213> ORGANISM: artificial sequence
<220> FEATURE:
<223> OTHER INFORMATION: Synthetic construct

<400> SEQUENCE: 103

Thr His Ser Thr His Asn His Gly Ser Pro Arg His Thr Asn Ala Asp
1               5                   10                  15

Ala

<210> SEQ ID NO 104
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 104

Gly Ser Cys Val Asp Thr His Lys Ala Asp Ser Cys Val Ala Asn Asn
1               5                   10                  15

Gly Pro Ala Thr
            20

<210> SEQ ID NO 105
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 105

Ala Gln Ser Gln Leu Pro Asp Lys His Ser Gly Leu His Glu Arg Ala
1               5                   10                  15

Pro Gln Arg Tyr
            20

<210> SEQ ID NO 106
<211> LENGTH: 20
```

-continued

```
<212> TYPE: PRT
<213> ORGANISM: artificial sequence
<220> FEATURE:
<223> OTHER INFORMATION: Synthetic construct

<400> SEQUENCE: 106

Ala Gln Ser Gln Leu Pro Ala Lys His Ser Gly Leu His Glu Arg Ala
1               5                   10                  15

Pro Gln Arg Tyr
            20

<210> SEQ ID NO 107
<211> LENGTH: 20
<212> TYPE: PRT
<213> ORGANISM: artificial sequence
<220> FEATURE:
<223> OTHER INFORMATION: Synthetic construct

<400> SEQUENCE: 107

Ala Gln Ser Gln Leu Pro Glu Lys His Ser Gly Leu His Glu Arg Ala
1               5                   10                  15

Pro Gln Arg Tyr
            20

<210> SEQ ID NO 108
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 108

Thr Asp Met Met His Asn His Ser Asp Asn Ser Pro Pro His Arg Arg
1               5                   10                  15

Ser Pro Arg Asn
            20

<210> SEQ ID NO 109
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 109

Thr Pro Pro Glu Leu Ala His Thr Pro His His Leu Ala Gln Thr Arg
1               5                   10                  15

Leu Thr Asp Arg
            20

<210> SEQ ID NO 110
<211> LENGTH: 12
<212> TYPE: PRT
<213> ORGANISM: artificial sequence
<220> FEATURE:
<223> OTHER INFORMATION: Synthetic construct

<400> SEQUENCE: 110

Arg Leu Leu Arg Leu Leu Arg Leu Leu Arg Leu Leu
1               5                   10

<210> SEQ ID NO 111
<211> LENGTH: 12
<212> TYPE: PRT
<213> ORGANISM: artificial sequence
```

```
<220> FEATURE:
<223> OTHER INFORMATION: Synthetic construct

<400> SEQUENCE: 111

Thr Pro Pro Glu Leu Leu His Gly Glu Pro Arg Ser
1               5                   10

<210> SEQ ID NO 112
<211> LENGTH: 12
<212> TYPE: PRT
<213> ORGANISM: artificial sequence
<220> FEATURE:
<223> OTHER INFORMATION: Synthetic construct

<400> SEQUENCE: 112

Thr Pro Pro Glu Leu Leu His Gly Ala Pro Arg Ser
1               5                   10

<210> SEQ ID NO 113
<211> LENGTH: 12
<212> TYPE: PRT
<213> ORGANISM: artificial sequence
<220> FEATURE:
<223> OTHER INFORMATION: Synthetic construct

<400> SEQUENCE: 113

Glu Gln Ile Ser Gly Ser Leu Val Ala Ala Pro Trp
1               5                   10

<210> SEQ ID NO 114
<211> LENGTH: 12
<212> TYPE: PRT
<213> ORGANISM: artificial sequence
<220> FEATURE:
<223> OTHER INFORMATION: Synthetic construct

<400> SEQUENCE: 114

Asn Glu Val Pro Ala Arg Asn Ala Pro Trp Leu Val
1               5                   10

<210> SEQ ID NO 115
<211> LENGTH: 13
<212> TYPE: PRT
<213> ORGANISM: artificial sequence
<220> FEATURE:
<223> OTHER INFORMATION: Synthetic construct

<400> SEQUENCE: 115

Asn Ser Pro Gly Tyr Gln Ala Asp Ser Val Ala Ile Gly
1               5                   10

<210> SEQ ID NO 116
<211> LENGTH: 12
<212> TYPE: PRT
<213> ORGANISM: artificial sequence
<220> FEATURE:
<223> OTHER INFORMATION: Synthetic construct

<400> SEQUENCE: 116

Ala Lys Pro Ile Ser Gln His Leu Gln Arg Gly Ser
1               5                   10

<210> SEQ ID NO 117
<211> LENGTH: 12
<212> TYPE: PRT
<213> ORGANISM: artificial sequence
<220> FEATURE:
```

```
<223> OTHER INFORMATION: Synthetic construct

<400> SEQUENCE: 117

Leu Asp Thr Ser Phe Pro Pro Val Pro Phe His Ala
1               5                   10

<210> SEQ ID NO 118
<211> LENGTH: 12
<212> TYPE: PRT
<213> ORGANISM: artificial sequence
<220> FEATURE:
<223> OTHER INFORMATION: Synthetic construct

<400> SEQUENCE: 118

Ser Leu Asn Trp Val Thr Ile Pro Gly Pro Lys Ile
1               5                   10

<210> SEQ ID NO 119
<211> LENGTH: 12
<212> TYPE: PRT
<213> ORGANISM: artificial sequence
<220> FEATURE:
<223> OTHER INFORMATION: Synthetic construct

<400> SEQUENCE: 119

Thr Gln Asp Ser Ala Gln Lys Ser Pro Ser Pro Leu
1               5                   10

<210> SEQ ID NO 120
<211> LENGTH: 12
<212> TYPE: PRT
<213> ORGANISM: artificial sequence
<220> FEATURE:
<223> OTHER INFORMATION: Synthetic construct

<400> SEQUENCE: 120

Lys Glu Leu Gln Thr Arg Asn Val Val Gln Arg Glu
1               5                   10

<210> SEQ ID NO 121
<211> LENGTH: 12
<212> TYPE: PRT
<213> ORGANISM: artificial sequence
<220> FEATURE:
<223> OTHER INFORMATION: Synthetic construct

<400> SEQUENCE: 121

Gln Arg Asn Ser Pro Pro Ala Met Ser Arg Arg Asp
1               5                   10

<210> SEQ ID NO 122
<211> LENGTH: 12
<212> TYPE: PRT
<213> ORGANISM: artificial sequence
<220> FEATURE:
<223> OTHER INFORMATION: Synthetic construct

<400> SEQUENCE: 122

Thr Pro Thr Ala Asn Gln Phe Thr Gln Ser Val Pro
1               5                   10

<210> SEQ ID NO 123
<211> LENGTH: 12
<212> TYPE: PRT
<213> ORGANISM: artificial sequence
<220> FEATURE:
<223> OTHER INFORMATION: Synthetic construct
```

```
<400> SEQUENCE: 123

Ala Ala Gly Leu Ser Gln Lys His Glu Arg Asn Arg
1               5                   10

<210> SEQ ID NO 124
<211> LENGTH: 12
<212> TYPE: PRT
<213> ORGANISM: artificial sequence
<220> FEATURE:
<223> OTHER INFORMATION: Synthetic construct

<400> SEQUENCE: 124

Glu Thr Val His Gln Thr Pro Leu Ser Asp Arg Pro
1               5                   10

<210> SEQ ID NO 125
<211> LENGTH: 12
<212> TYPE: PRT
<213> ORGANISM: artificial sequence
<220> FEATURE:
<223> OTHER INFORMATION: Synthetic construct

<400> SEQUENCE: 125

Lys Asn Phe Pro Gln Gln Lys Glu Phe Pro Leu Ser
1               5                   10

<210> SEQ ID NO 126
<211> LENGTH: 12
<212> TYPE: PRT
<213> ORGANISM: artificial sequence
<220> FEATURE:
<223> OTHER INFORMATION: Synthetic construct

<400> SEQUENCE: 126

Leu Pro Ala Leu His Ile Gln Arg His Pro Arg Met
1               5                   10

<210> SEQ ID NO 127
<211> LENGTH: 12
<212> TYPE: PRT
<213> ORGANISM: artificial sequence
<220> FEATURE:
<223> OTHER INFORMATION: Synthetic construct

<400> SEQUENCE: 127

Gln Pro Ser His Ser Gln Ser His Asn Leu Arg Ser
1               5                   10

<210> SEQ ID NO 128
<211> LENGTH: 12
<212> TYPE: PRT
<213> ORGANISM: artificial sequence
<220> FEATURE:
<223> OTHER INFORMATION: Synthetic construct

<400> SEQUENCE: 128

Arg Gly Ser Gln Lys Ser Lys Pro Pro Arg Pro Pro
1               5                   10

<210> SEQ ID NO 129
<211> LENGTH: 12
<212> TYPE: PRT
<213> ORGANISM: artificial sequence
<220> FEATURE:
<223> OTHER INFORMATION: Synthetic construct
```

```
<400> SEQUENCE: 129

Thr His Thr Gln Lys Thr Pro Leu Leu Tyr Tyr His
1               5                   10

<210> SEQ ID NO 130
<211> LENGTH: 12
<212> TYPE: PRT
<213> ORGANISM: artificial sequence
<220> FEATURE:
<223> OTHER INFORMATION: Synthetic construct

<400> SEQUENCE: 130

Thr Lys Gly Ser Ser Gln Ala Ile Leu Lys Ser Thr
1               5                   10

<210> SEQ ID NO 131
<211> LENGTH: 7
<212> TYPE: PRT
<213> ORGANISM: artificial sequence
<220> FEATURE:
<223> OTHER INFORMATION: Synthetic construct

<400> SEQUENCE: 131

Thr Ala Ala Thr Thr Ser Pro
1               5

<210> SEQ ID NO 132
<211> LENGTH: 7
<212> TYPE: PRT
<213> ORGANISM: artificial sequence
<220> FEATURE:
<223> OTHER INFORMATION: Synthetic construct

<400> SEQUENCE: 132

Leu Gly Ile Pro Gln Asn Leu
1               5

<210> SEQ ID NO 133
<211> LENGTH: 20
<212> TYPE: PRT
<213> ORGANISM: artificial sequence
<220> FEATURE:
<223> OTHER INFORMATION: Synthetic construct

<400> SEQUENCE: 133

Thr His Ser Thr His Asn His Gly Ser Pro Arg His Thr Asn Ala Asp
1               5                   10                  15

Ala Gly Asn Pro
            20

<210> SEQ ID NO 134
<211> LENGTH: 20
<212> TYPE: PRT
<213> ORGANISM: artificial sequence
<220> FEATURE:
<223> OTHER INFORMATION: Synthetic construct

<400> SEQUENCE: 134

Gln Gln His Lys Val His His Gln Asn Pro Asp Arg Ser Thr Gln Asp
1               5                   10                  15

Ala His His Ser
            20

<210> SEQ ID NO 135
<211> LENGTH: 15
```

```
<212> TYPE: PRT
<213> ORGANISM: artificial sequence
<220> FEATURE:
<223> OTHER INFORMATION: Synthetic construct

<400> SEQUENCE: 135

His His Gly Thr His His Asn Ala Thr Lys Gln Lys Asn His Val
1               5                   10                  15

<210> SEQ ID NO 136
<211> LENGTH: 15
<212> TYPE: PRT
<213> ORGANISM: artificial sequence
<220> FEATURE:
<223> OTHER INFORMATION: Synthetic construct

<400> SEQUENCE: 136

Ser Thr Leu His Lys Tyr Lys Ser Gln Asp Pro Thr Pro His His
1               5                   10                  15

<210> SEQ ID NO 137
<211> LENGTH: 12
<212> TYPE: PRT
<213> ORGANISM: artificial sequence
<220> FEATURE:
<223> OTHER INFORMATION: Synthetic construct

<400> SEQUENCE: 137

Ser Val Ser Val Gly Met Lys Pro Ser Pro Arg Pro
1               5                   10

<210> SEQ ID NO 138
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 138

Thr Pro Pro Thr Asn Val Leu Met Leu Ala Thr Lys
1               5                   10

<210> SEQ ID NO 139
<211> LENGTH: 12
<212> TYPE: PRT
<213> ORGANISM: artificial sequence
<220> FEATURE:
<223> OTHER INFORMATION: Synthetic construct

<400> SEQUENCE: 139

Thr Pro Pro Glu Leu Leu His Gly Asp Pro Arg Ser
1               5                   10

<210> SEQ ID NO 140
<211> LENGTH: 7
<212> TYPE: PRT
<213> ORGANISM: artificial sequence
<220> FEATURE:
<223> OTHER INFORMATION: synthetic hair-binding peptide

<400> SEQUENCE: 140

Asn Thr Ser Gln Leu Ser Thr
1               5

<210> SEQ ID NO 141
<211> LENGTH: 15
<212> TYPE: PRT
```

<213> ORGANISM: artificial sequence
<220> FEATURE:
<223> OTHER INFORMATION: Synthetic construct

<400> SEQUENCE: 141

Ser Thr Leu His Lys Tyr Lys Ser Gln Asp Pro Thr Pro His His
1               5                   10                  15

<210> SEQ ID NO 142
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 142

Gly Met Pro Ala Met His Trp Ile His Pro Phe Ala
1               5                   10

<210> SEQ ID NO 143
<211> LENGTH: 15
<212> TYPE: PRT
<213> ORGANISM: artificial sequence
<220> FEATURE:
<223> OTHER INFORMATION: synthetic hair-binding peptide

<400> SEQUENCE: 143

His Asp His Lys Asn Gln Lys Glu Thr His Gln Arg His Ala Ala
1               5                   10                  15

<210> SEQ ID NO 144
<211> LENGTH: 20
<212> TYPE: PRT
<213> ORGANISM: artificial sequence
<220> FEATURE:
<223> OTHER INFORMATION: Synthetic construct

<400> SEQUENCE: 144

His Asn His Met Gln Glu Arg Tyr Thr Asp Pro Gln His Ser Pro Ser
1               5                   10                  15

Val Asn Gly Leu
            20

<210> SEQ ID NO 145
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 145

Thr Ala Glu Ile Gln Ser Ser Lys Asn Pro Asn Pro His Pro Gln Arg
1               5                   10                  15

Ser Trp Thr Asn
            20

<210> SEQ ID NO 146
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 146

Ser Ser Ala Asp Phe Ala Ser Phe Gly Phe Phe Gly Phe Ser Ala Ala
1               5                   10                  15

-continued

```
Ser Ala Asp Ser Arg
            20

<210> SEQ ID NO 147
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 147

Ser Ser Phe Ala Glu Ala Trp Ser Arg Ala Trp Pro Arg Ala Glu Val
1               5                   10                  15

Phe Phe Pro Ser Arg Gly Tyr
            20

<210> SEQ ID NO 148
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 148

Ser Ser Phe Ser Val Asn Glu Pro His Ala Trp Met Ala Pro Leu Ser
1               5                   10                  15

Arg

<210> SEQ ID NO 149
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 149

Ser Ser Phe Ser Trp Val Tyr Gly His Gly Gly Leu Gly Phe Ala Ser
1               5                   10                  15

Arg

<210> SEQ ID NO 150
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 150

Ser Ser Phe Val Ser Trp Ser Pro Tyr Lys Ser Pro Pro Glu Leu Ser
1               5                   10                  15

Arg

<210> SEQ ID NO 151
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 151

Ser Ser Phe Tyr Gly Ser Ser Ala Phe Val Ser Ser Gly Val Ser Val
1               5                   10                  15

Ala Tyr Gly Ser Arg
```

<210> SEQ ID NO 152
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 152

Ser Ser Gly Ser Val Ala Val Ser Ala Glu Ala Ser Trp Phe Ser Gly
1               5                   10                  15

Val Ala Ala Ser Arg
            20

<210> SEQ ID NO 153
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 153

Ser Ser His Asp Glu His Tyr Gln Tyr His Tyr Tyr Ser Ser Arg
1               5                   10                  15

<210> SEQ ID NO 154
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 154

Ser Ser His Tyr Tyr Tyr Asn Asp Tyr Asp His Gln Ser Ser Arg
1               5                   10                  15

<210> SEQ ID NO 155
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 155

Ser Ser Leu Phe Asn Met Tyr Gly His Gln Ser Val Leu Gly Pro Ser
1               5                   10                  15

Arg

<210> SEQ ID NO 156
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 156

Ser Ser Leu Phe Ser Asp Val His Tyr Gly Ser Asn Lys Ala Leu Ser
1               5                   10                  15

Arg

<210> SEQ ID NO 157
<211> LENGTH: 17
<212> TYPE: PRT
<213> ORGANISM: artificial sequence

```
<220> FEATURE:
<223> OTHER INFORMATION: Dyed-hair-bindg peptide

<400> SEQUENCE: 157

Ser Ser Leu Leu Ser Asp Phe His Tyr Gly Asp Met Trp Asp Ala Ser
1               5                   10                  15

Arg

<210> SEQ ID NO 158
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 158

Ser Ser Asn Tyr Asn Tyr Asn Tyr Gln Tyr Ser Ser Arg
1               5                   10                  15

<210> SEQ ID NO 159
<211> LENGTH: 21
<212> TYPE: PRT
<213> ORGANISM: artificial sequence
<220> FEATURE:
<223> OTHER INFORMATION: synethetic construct

<400> SEQUENCE: 159

Ser Ser Asn Tyr Asn Tyr Asn Tyr Gln Tyr Ser Ser Arg Glu
1               5                   10                  15

Gly Glu Gly Glu Arg
            20

<210> SEQ ID NO 160
<211> LENGTH: 21
<212> TYPE: PRT
<213> ORGANISM: ARTIFICIAL SEQUENCE
<220> FEATURE:
<223> OTHER INFORMATION: Synthetic construct

<400> SEQUENCE: 160

Ser Ser Asn Tyr Asn Tyr Asn Tyr Gln Tyr Ser Ser Arg Lys
1               5                   10                  15

Arg Lys Arg Lys Asp
            20

<210> SEQ ID NO 161
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 161

Ser Ser Gln Tyr Tyr Gln Asp Tyr Gln Tyr Tyr His Ser Ser Arg
1               5                   10                  15

<210> SEQ ID NO 162
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 162

Ser Ser Ser Cys Met Gly Ser His Asn Pro Arg Met Ser Val Glu Glu
```

```
                1               5                  10                 15
Ser Thr Arg Asn Cys Ser Arg
            20

<210> SEQ ID NO 163
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 163

Ser Ser Ser Cys Asn Asn Asn Trp Phe Tyr Ser Ser Thr Leu Pro Gly
1               5                   10                  15

Gly Asp His Ala Cys Ser Arg
            20

<210> SEQ ID NO 164
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 164

Ser Ser Ser Cys Tyr Asp Val Glu Cys Ser Ser Phe Val Ala Trp Met
1               5                   10                  15

Arg Gly Pro Ser Ser Ser Arg
            20

<210> SEQ ID NO 165
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 165

Ser Ser Ser Phe Ala Ala Ser Ser Ala Phe Ser Phe Leu Val Asp Ala
1               5                   10                  15

Val Ala Trp Ser Arg
            20

<210> SEQ ID NO 166
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 166

Ser Ser Ser Phe Ala Tyr Leu Val Pro Asp Asp Gly Trp Leu Ser Ser
1               5                   10                  15

Arg

<210> SEQ ID NO 167
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 167

Ser Ser Ser Gly Ala Val Phe Ser Ser Gly Gly Ala Asp Ala Gly Trp
```

```
1               5               10              15
Gly Val Trp Ser Arg
            20

<210> SEQ ID NO 168
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 168

Ser Ser Ser Ser Ala Asp Ala Ala Tyr Gly His Cys Cys Gly Ala Gly
1               5                   10                  15

Phe Ser Thr Phe Ser Ser Arg
            20

<210> SEQ ID NO 169
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 169

Ser Ser Ser Ser Asp Val His Asn Ser Ile Ile Gly Trp Asp Phe Tyr
1               5                   10                  15

His Ser Arg Gly Ser Ser Arg
            20

<210> SEQ ID NO 170
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 170

Ser Ser Ser Ser Leu Asp Phe Phe Ser Tyr Ser Ala Phe Ser Gly Gly
1               5                   10                  15

Val Ala Glu Ser Arg
            20

<210> SEQ ID NO 171
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 171

Ser Ser Ser Ser Asn Asp Ser Asn Val Ser Trp Phe His Tyr Tyr Ala
1               5                   10                  15

Ser Gly Leu Thr Ser Ser Arg
            20

<210> SEQ ID NO 172
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 172
```

```
Ser Ser Val Asp Tyr Glu Val Pro Leu Ala Val Ala Ala Glu Trp Gly
1               5                   10                  15

Phe Ser Val Ser Arg
                20
```

<210> SEQ ID NO 173
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 173

```
Ser Ser Tyr His Tyr Asp Tyr Asp His Tyr Tyr Glu Ser Ser Arg
1               5                   10                  15
```

<210> SEQ ID NO 174
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 174

```
Ser Ser Tyr Tyr Asn Tyr His Tyr Gln Tyr Gln Asp Ser Ser Arg
1               5                   10                  15
```

<210> SEQ ID NO 175
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 175

```
Ser Ser Tyr Tyr Tyr Asp Tyr Tyr Gln Gln Asp Tyr Ser Ser Arg
1               5                   10                  15
```

<210> SEQ ID NO 176
<211> LENGTH: 12
<212> TYPE: PRT
<213> ORGANISM: artificial sequence
<220> FEATURE:
<223> OTHER INFORMATION: Synthetic construct

<400> SEQUENCE: 176

```
Lys Arg Gly Arg His Lys Arg Pro Lys Arg His Lys
1               5                   10
```

<210> SEQ ID NO 177
<211> LENGTH: 7
<212> TYPE: PRT
<213> ORGANISM: artificial sequence
<220> FEATURE:
<223> OTHER INFORMATION: Synthetic construct

<400> SEQUENCE: 177

```
Arg Leu Leu Arg Leu Leu Arg
1               5
```

<210> SEQ ID NO 178
<211> LENGTH: 12
<212> TYPE: PRT
<213> ORGANISM: artificial sequence
<220> FEATURE:
<223> OTHER INFORMATION: Synthetic construct

```
<400> SEQUENCE: 178

His Lys Pro Arg Gly Gly Arg Lys Lys Ala Leu His
1               5                   10

<210> SEQ ID NO 179
<211> LENGTH: 18
<212> TYPE: PRT
<213> ORGANISM: artificial sequence
<220> FEATURE:
<223> OTHER INFORMATION: Synthetic construct

<400> SEQUENCE: 179

Lys Pro Arg Pro Pro His Gly Lys Lys His Arg Pro Lys His Arg Pro
1               5                   10                  15

Lys Lys

<210> SEQ ID NO 180
<211> LENGTH: 18
<212> TYPE: PRT
<213> ORGANISM: artificial sequence
<220> FEATURE:
<223> OTHER INFORMATION: Synthetic construct

<400> SEQUENCE: 180

Arg Gly Arg Pro Lys Lys Gly His Gly Lys Arg Pro Gly His Arg Ala
1               5                   10                  15

Arg Lys

<210> SEQ ID NO 181
<211> LENGTH: 12
<212> TYPE: PRT
<213> ORGANISM: artificial sequence
<220> FEATURE:
<223> OTHER INFORMATION: Synthetic construct

<400> SEQUENCE: 181

Thr Pro Phe His Ser Pro Glu Asn Ala Pro Gly Ser
1               5                   10

<210> SEQ ID NO 182
<211> LENGTH: 13
<212> TYPE: PRT
<213> ORGANISM: artificial sequence
<220> FEATURE:
<223> OTHER INFORMATION: Synthetic construct

<400> SEQUENCE: 182

Thr Pro Phe His Ser Pro Glu Asn Ala Pro Gly Ser Lys
1               5                   10

<210> SEQ ID NO 183
<211> LENGTH: 16
<212> TYPE: PRT
<213> ORGANISM: artificial sequence
<220> FEATURE:
<223> OTHER INFORMATION: Synthetic construct

<400> SEQUENCE: 183

Thr Pro Phe His Ser Pro Glu Asn Ala Pro Gly Ser Gly Gly Gly Ser
1               5                   10                  15

<210> SEQ ID NO 184
<211> LENGTH: 17
<212> TYPE: PRT
<213> ORGANISM: artificial sequence
```

```
<220> FEATURE:
<223> OTHER INFORMATION: Synthetic construct

<400> SEQUENCE: 184

Thr Pro Phe His Ser Pro Glu Asn Ala Pro Gly Ser Gly Gly Ser
1               5                   10                  15

Ser

<210> SEQ ID NO 185
<211> LENGTH: 15
<212> TYPE: PRT
<213> ORGANISM: artificial sequence
<220> FEATURE:
<223> OTHER INFORMATION: Synthetic construct

<400> SEQUENCE: 185

Thr Pro Phe His Ser Pro Glu Asn Ala Pro Gly Ser Gly Gly Gly
1               5                   10                  15

<210> SEQ ID NO 186
<211> LENGTH: 7
<212> TYPE: PRT
<213> ORGANISM: artificial sequence
<220> FEATURE:
<223> OTHER INFORMATION: Synthetic construct

<400> SEQUENCE: 186

Phe Thr Gln Ser Leu Pro Arg
1               5

<210> SEQ ID NO 187
<211> LENGTH: 12
<212> TYPE: PRT
<213> ORGANISM: artificial sequence
<220> FEATURE:
<223> OTHER INFORMATION: Synthetic construct

<400> SEQUENCE: 187

Lys Gln Ala Thr Phe Pro Pro Asn Pro Thr Ala Tyr
1               5                   10

<210> SEQ ID NO 188
<211> LENGTH: 12
<212> TYPE: PRT
<213> ORGANISM: artificial sequence
<220> FEATURE:
<223> OTHER INFORMATION: Synthetic construct

<400> SEQUENCE: 188

His Gly His Met Val Ser Thr Ser Gln Leu Ser Ile
1               5                   10

<210> SEQ ID NO 189
<211> LENGTH: 7
<212> TYPE: PRT
<213> ORGANISM: artificial sequence
<220> FEATURE:
<223> OTHER INFORMATION: Synthetic construct

<400> SEQUENCE: 189

Leu Ser Pro Ser Arg Met Lys
1               5

<210> SEQ ID NO 190
<211> LENGTH: 7
<212> TYPE: PRT
```

```
<213> ORGANISM: artificial sequence
<220> FEATURE:
<223> OTHER INFORMATION: Synthetic construct

<400> SEQUENCE: 190

Leu Pro Ile Pro Arg Met Lys
1               5

<210> SEQ ID NO 191
<211> LENGTH: 7
<212> TYPE: PRT
<213> ORGANISM: artificial sequence
<220> FEATURE:
<223> OTHER INFORMATION: Synthetic construct

<400> SEQUENCE: 191

His Gln Arg Pro Tyr Leu Thr
1               5

<210> SEQ ID NO 192
<211> LENGTH: 7
<212> TYPE: PRT
<213> ORGANISM: artificial sequence
<220> FEATURE:
<223> OTHER INFORMATION: Synthetic construct

<400> SEQUENCE: 192

Phe Pro Pro Leu Leu Arg Leu
1               5

<210> SEQ ID NO 193
<211> LENGTH: 7
<212> TYPE: PRT
<213> ORGANISM: artificial sequence
<220> FEATURE:
<223> OTHER INFORMATION: Synthetic construct

<400> SEQUENCE: 193

Gln Ala Thr Phe Met Tyr Asn
1               5

<210> SEQ ID NO 194
<211> LENGTH: 11
<212> TYPE: PRT
<213> ORGANISM: artificial sequence
<220> FEATURE:
<223> OTHER INFORMATION: Synthetic construct

<400> SEQUENCE: 194

Val Leu Thr Ser Gln Leu Pro Asn His Ser Met
1               5                   10

<210> SEQ ID NO 195
<211> LENGTH: 7
<212> TYPE: PRT
<213> ORGANISM: artificial sequence
<220> FEATURE:
<223> OTHER INFORMATION: Synthetic construct

<400> SEQUENCE: 195

His Ser Thr Ala Tyr Leu Thr
1               5

<210> SEQ ID NO 196
<211> LENGTH: 12
<212> TYPE: PRT
<213> ORGANISM: artificial sequence
```

```
<220> FEATURE:
<223> OTHER INFORMATION: Synthetic construct

<400> SEQUENCE: 196

Ala Pro Gln Gln Arg Pro Met Lys Thr Phe Asn Thr
1               5                   10

<210> SEQ ID NO 197
<211> LENGTH: 12
<212> TYPE: PRT
<213> ORGANISM: artificial sequence
<220> FEATURE:
<223> OTHER INFORMATION: Synthetic construct

<400> SEQUENCE: 197

Ala Pro Gln Gln Arg Pro Met Lys Thr Val Gln Tyr
1               5                   10

<210> SEQ ID NO 198
<211> LENGTH: 7
<212> TYPE: PRT
<213> ORGANISM: artificial sequence
<220> FEATURE:
<223> OTHER INFORMATION: Synthetic construct

<400> SEQUENCE: 198

Pro Pro Trp Leu Asp Leu Leu
1               5

<210> SEQ ID NO 199
<211> LENGTH: 7
<212> TYPE: PRT
<213> ORGANISM: artificial sequence
<220> FEATURE:
<223> OTHER INFORMATION: Synthetic construct

<400> SEQUENCE: 199

Pro Pro Trp Thr Phe Pro Leu
1               5

<210> SEQ ID NO 200
<211> LENGTH: 7
<212> TYPE: PRT
<213> ORGANISM: artificial sequence
<220> FEATURE:
<223> OTHER INFORMATION: Synthetic construct

<400> SEQUENCE: 200

Ser Val Thr His Leu Thr Ser
1               5

<210> SEQ ID NO 201
<211> LENGTH: 7
<212> TYPE: PRT
<213> ORGANISM: artificial sequence
<220> FEATURE:
<223> OTHER INFORMATION: Synthetic construct

<400> SEQUENCE: 201

Val Ile Thr Arg Leu Thr Ser
1               5

<210> SEQ ID NO 202
<211> LENGTH: 12
<212> TYPE: PRT
<213> ORGANISM: artificial sequence
<220> FEATURE:
```

-continued

<223> OTHER INFORMATION: Synthetic construct

<400> SEQUENCE: 202

Asp Leu Lys Pro Pro Leu Leu Ala Leu Ser Lys Val
1               5                   10

<210> SEQ ID NO 203
<211> LENGTH: 12
<212> TYPE: PRT
<213> ORGANISM: artificial sequence
<220> FEATURE:
<223> OTHER INFORMATION: Synthetic construct

<400> SEQUENCE: 203

Ser His Pro Ser Gly Ala Leu Gln Glu Gly Thr Phe
1               5                   10

<210> SEQ ID NO 204
<211> LENGTH: 12
<212> TYPE: PRT
<213> ORGANISM: artificial sequence
<220> FEATURE:
<223> OTHER INFORMATION: Synthetic construct

<400> SEQUENCE: 204

Phe Pro Leu Thr Ser Lys Pro Ser Gly Ala Cys Thr
1               5                   10

<210> SEQ ID NO 205
<211> LENGTH: 12
<212> TYPE: PRT
<213> ORGANISM: artificial sequence
<220> FEATURE:
<223> OTHER INFORMATION: Synthetic construct

<400> SEQUENCE: 205

Asp Leu Lys Pro Pro Leu Leu Ala Leu Ser Lys Val
1               5                   10

<210> SEQ ID NO 206
<211> LENGTH: 7
<212> TYPE: PRT
<213> ORGANISM: artificial sequence
<220> FEATURE:
<223> OTHER INFORMATION: Synthetic construct

<400> SEQUENCE: 206

Pro Leu Leu Ala Leu His Ser
1               5

<210> SEQ ID NO 207
<211> LENGTH: 7
<212> TYPE: PRT
<213> ORGANISM: artificial sequence
<220> FEATURE:
<223> OTHER INFORMATION: Synthetic construct

<400> SEQUENCE: 207

Val Pro Ile Ser Thr Gln Ile
1               5

<210> SEQ ID NO 208
<211> LENGTH: 12
<212> TYPE: PRT
<213> ORGANISM: artificial sequence
<220> FEATURE:
<223> OTHER INFORMATION: Synthetic construct

```
<400> SEQUENCE: 208

Tyr Ala Lys Gln His Tyr Pro Ile Ser Thr Phe Lys
1               5                   10

<210> SEQ ID NO 209
<211> LENGTH: 7
<212> TYPE: PRT
<213> ORGANISM: artificial sequence
<220> FEATURE:
<223> OTHER INFORMATION: Synthetic construct

<400> SEQUENCE: 209

His Ser Thr Ala Tyr Leu Thr
1               5

<210> SEQ ID NO 210
<211> LENGTH: 12
<212> TYPE: PRT
<213> ORGANISM: artificial sequence
<220> FEATURE:
<223> OTHER INFORMATION: Synthetic construct

<400> SEQUENCE: 210

Ser Thr Ala Tyr Leu Val Ala Met Ser Ala Ala Pro
1               5                   10

<210> SEQ ID NO 211
<211> LENGTH: 12
<212> TYPE: PRT
<213> ORGANISM: artificial sequence
<220> FEATURE:
<223> OTHER INFORMATION: Synthetic construct

<400> SEQUENCE: 211

Ser Val Ser Val Gly Met Lys Pro Ser Pro Arg Pro
1               5                   10

<210> SEQ ID NO 212
<211> LENGTH: 12
<212> TYPE: PRT
<213> ORGANISM: artificial sequence
<220> FEATURE:
<223> OTHER INFORMATION: Synthetic construct

<400> SEQUENCE: 212

Thr Met Gly Phe Thr Ala Pro Arg Phe Pro His Tyr
1               5                   10

<210> SEQ ID NO 213
<211> LENGTH: 12
<212> TYPE: PRT
<213> ORGANISM: artificial sequence
<220> FEATURE:
<223> OTHER INFORMATION: Synthetic construct

<400> SEQUENCE: 213

Asn Leu Gln His Ser Val Gly Thr Ser Pro Val Trp
1               5                   10

<210> SEQ ID NO 214
<211> LENGTH: 15
<212> TYPE: PRT
<213> ORGANISM: artificial sequence
<220> FEATURE:
<223> OTHER INFORMATION: Synthetic construct
```

```
<400> SEQUENCE: 214

Gln Leu Ser Tyr His Ala Tyr Pro Gln Ala Asn His His Ala Pro
1               5                   10                  15

<210> SEQ ID NO 215
<211> LENGTH: 12
<212> TYPE: PRT
<213> ORGANISM: artificial sequence
<220> FEATURE:
<223> OTHER INFORMATION: Synthetic construct

<400> SEQUENCE: 215

Asn Gln Ala Ala Ser Ile Thr Lys Arg Val Pro Tyr
1               5                   10

<210> SEQ ID NO 216
<211> LENGTH: 14
<212> TYPE: PRT
<213> ORGANISM: artificial sequence
<220> FEATURE:
<223> OTHER INFORMATION: Synthetic construct

<400> SEQUENCE: 216

Ser Gly Cys His Leu Val Tyr Asp Asn Gly Phe Cys Asp His
1               5                   10

<210> SEQ ID NO 217
<211> LENGTH: 14
<212> TYPE: PRT
<213> ORGANISM: artificial sequence
<220> FEATURE:
<223> OTHER INFORMATION: Synthetic construct

<400> SEQUENCE: 217

Ala Ser Cys Pro Ser Ala Ser His Ala Asp Pro Cys Ala His
1               5                   10

<210> SEQ ID NO 218
<211> LENGTH: 14
<212> TYPE: PRT
<213> ORGANISM: artificial sequence
<220> FEATURE:
<223> OTHER INFORMATION: Synthetic construct

<400> SEQUENCE: 218

Asn Leu Cys Asp Ser Ala Arg Asp Ser Pro Arg Cys Lys Val
1               5                   10

<210> SEQ ID NO 219
<211> LENGTH: 12
<212> TYPE: PRT
<213> ORGANISM: artificial sequence
<220> FEATURE:
<223> OTHER INFORMATION: Synthetic construct

<400> SEQUENCE: 219

Asn His Ser Asn Trp Lys Thr Ala Ala Asp Phe Leu
1               5                   10

<210> SEQ ID NO 220
<211> LENGTH: 12
<212> TYPE: PRT
<213> ORGANISM: artificial sequence
<220> FEATURE:
<223> OTHER INFORMATION: Synthetic construct

<400> SEQUENCE: 220
```

```
Gly Ser Ser Thr Val Gly Arg Pro Leu Ser Tyr Glu
1               5                   10

<210> SEQ ID NO 221
<211> LENGTH: 12
<212> TYPE: PRT
<213> ORGANISM: artificial sequence
<220> FEATURE:
<223> OTHER INFORMATION: Synthetic construct

<400> SEQUENCE: 221

Ser Asp Thr Ile Ser Arg Leu His Val Ser Met Thr
1               5                   10

<210> SEQ ID NO 222
<211> LENGTH: 12
<212> TYPE: PRT
<213> ORGANISM: artificial sequence
<220> FEATURE:
<223> OTHER INFORMATION: Synthetic construct

<400> SEQUENCE: 222

Ser Pro Leu Thr Val Pro Tyr Glu Arg Lys Leu Leu
1               5                   10

<210> SEQ ID NO 223
<211> LENGTH: 12
<212> TYPE: PRT
<213> ORGANISM: artificial sequence
<220> FEATURE:
<223> OTHER INFORMATION: Synthetic construct

<400> SEQUENCE: 223

Ser Pro Tyr Pro Ser Trp Ser Thr Pro Ala Gly Arg
1               5                   10

<210> SEQ ID NO 224
<211> LENGTH: 12
<212> TYPE: PRT
<213> ORGANISM: artificial sequence
<220> FEATURE:
<223> OTHER INFORMATION: Synthetic construct

<400> SEQUENCE: 224

Val Gln Pro Ile Thr Asn Thr Arg Tyr Glu Gly Gly
1               5                   10

<210> SEQ ID NO 225
<211> LENGTH: 12
<212> TYPE: PRT
<213> ORGANISM: artificial sequence
<220> FEATURE:
<223> OTHER INFORMATION: Synthetic construct

<400> SEQUENCE: 225

Trp Pro Met His Pro Glu Lys Gly Ser Arg Trp Ser
1               5                   10

<210> SEQ ID NO 226
<211> LENGTH: 14
<212> TYPE: PRT
<213> ORGANISM: artificial sequence
<220> FEATURE:
<223> OTHER INFORMATION: Synthetic construct

<400> SEQUENCE: 226
```

```
Asp Ala Cys Ser Gly Asn Gly His Pro Asn Asn Cys Asp Arg
1               5                   10
```

<210> SEQ ID NO 227
<211> LENGTH: 14
<212> TYPE: PRT
<213> ORGANISM: artificial sequence
<220> FEATURE:
<223> OTHER INFORMATION: Synthetic construct

<400> SEQUENCE: 227

```
Asp His Cys Leu Gly Arg Gln Leu Gln Pro Val Cys Tyr Pro
1               5                   10
```

<210> SEQ ID NO 228
<211> LENGTH: 14
<212> TYPE: PRT
<213> ORGANISM: artificial sequence
<220> FEATURE:
<223> OTHER INFORMATION: Synthetic construct

<400> SEQUENCE: 228

```
Asp Trp Cys Asp Thr Ile Ile Pro Gly Arg Thr Cys His Gly
1               5                   10
```

<210> SEQ ID NO 229
<211> LENGTH: 12
<212> TYPE: PRT
<213> ORGANISM: artificial sequence
<220> FEATURE:
<223> OTHER INFORMATION: Synthetic construct

<400> SEQUENCE: 229

```
Ala Leu Pro Arg Ile Ala Asn Thr Trp Ser Pro Ser
1               5                   10
```

<210> SEQ ID NO 230
<211> LENGTH: 12
<212> TYPE: PRT
<213> ORGANISM: artificial sequence
<220> FEATURE:
<223> OTHER INFORMATION: Synthetic construct

<400> SEQUENCE: 230

```
Tyr Pro Ser Phe Ser Pro Thr Tyr Arg Pro Ala Phe
1               5                   10
```

<210> SEQ ID NO 231
<211> LENGTH: 20
<212> TYPE: PRT
<213> ORGANISM: artificial sequence
<220> FEATURE:
<223> OTHER INFORMATION: Synthetic construct

<400> SEQUENCE: 231

```
Ala His Pro Glu Ser Leu Gly Ile Lys Tyr Ala Leu Asp Gly Asn Ser
1               5                   10                  15

Asp Pro His Ala
            20
```

<210> SEQ ID NO 232
<211> LENGTH: 20
<212> TYPE: PRT
<213> ORGANISM: artificial sequence
<220> FEATURE:
<223> OTHER INFORMATION: Synthetic construct

```
<400> SEQUENCE: 232

Ala Ser Val Ser Asn Tyr Pro Pro Ile His His Leu Ala Thr Ser Asn
1               5                   10                  15

Thr Thr Val Asn
            20

<210> SEQ ID NO 233
<211> LENGTH: 14
<212> TYPE: PRT
<213> ORGANISM: artificial sequence
<220> FEATURE:
<223> OTHER INFORMATION: Synthetic construct

<400> SEQUENCE: 233

Asp Glu Cys Met Glu Pro Leu Asn Ala Ala His Cys Trp Arg
1               5                   10

<210> SEQ ID NO 234
<211> LENGTH: 14
<212> TYPE: PRT
<213> ORGANISM: artificial sequence
<220> FEATURE:
<223> OTHER INFORMATION: Synthetic construct

<400> SEQUENCE: 234

Asp Glu Cys Met His Gly Ser Asp Val Glu Phe Cys Thr Ser
1               5                   10

<210> SEQ ID NO 235
<211> LENGTH: 14
<212> TYPE: PRT
<213> ORGANISM: artificial sequence
<220> FEATURE:
<223> OTHER INFORMATION: Synthetic construct

<400> SEQUENCE: 235

Asp Leu Cys Ser Met Gln Met Met Asn Thr Gly Cys His Tyr
1               5                   10

<210> SEQ ID NO 236
<211> LENGTH: 14
<212> TYPE: PRT
<213> ORGANISM: artificial sequence
<220> FEATURE:
<223> OTHER INFORMATION: Synthetic construct

<400> SEQUENCE: 236

Asp Leu Cys Ser Ser Pro Ser Thr Trp Gly Ser Cys Ile Arg
1               5                   10

<210> SEQ ID NO 237
<211> LENGTH: 20
<212> TYPE: PRT
<213> ORGANISM: artificial sequence
<220> FEATURE:
<223> OTHER INFORMATION: Synthetic construct

<400> SEQUENCE: 237

Asp Pro Asn Glu Ser Asn Tyr Glu Asn Ala Thr Thr Val Ser Gln Pro
1               5                   10                  15

Thr Arg His Leu
            20

<210> SEQ ID NO 238
<211> LENGTH: 20
```

```
<212> TYPE: PRT
<213> ORGANISM: artificial sequence
<220> FEATURE:
<223> OTHER INFORMATION: Synthetic construct

<400> SEQUENCE: 238

Glu Pro Thr His Pro Thr Met Arg Ala Gln Met His Gln Ser Leu Arg
1               5                   10                  15

Ser Ser Ser Pro
            20

<210> SEQ ID NO 239
<211> LENGTH: 20
<212> TYPE: PRT
<213> ORGANISM: artificial sequence
<220> FEATURE:
<223> OTHER INFORMATION: Synthetic construct

<400> SEQUENCE: 239

Gly Asn Thr Asp Thr Thr Pro Pro Asn Ala Val Met Glu Pro Thr Val
1               5                   10                  15

Gln His Lys Trp
            20

<210> SEQ ID NO 240
<211> LENGTH: 15
<212> TYPE: PRT
<213> ORGANISM: artificial sequence
<220> FEATURE:
<223> OTHER INFORMATION: Synthetic construct

<400> SEQUENCE: 240

Asn Gly Pro Asp Met Val Gln Ser Val Gly Lys His Lys Asn Ser
1               5                   10                  15

<210> SEQ ID NO 241
<211> LENGTH: 15
<212> TYPE: PRT
<213> ORGANISM: artificial sequence
<220> FEATURE:
<223> OTHER INFORMATION: Synthetic construct

<400> SEQUENCE: 241

Asn Gly Pro Glu Val Arg Gln Ile Pro Ala Asn Phe Glu Lys Leu
1               5                   10                  15

<210> SEQ ID NO 242
<211> LENGTH: 20
<212> TYPE: PRT
<213> ORGANISM: artificial sequence
<220> FEATURE:
<223> OTHER INFORMATION: Synthetic construct

<400> SEQUENCE: 242

Asn Asn Thr Ser Ala Asp Asn Pro Pro Glu Thr Asp Ser Lys His His
1               5                   10                  15

Leu Ser Met Ser
            20

<210> SEQ ID NO 243
<211> LENGTH: 20
<212> TYPE: PRT
<213> ORGANISM: artificial sequence
<220> FEATURE:
<223> OTHER INFORMATION: Synthetic construct
```

-continued

```
<400> SEQUENCE: 243

Asn Asn Thr Trp Pro Glu Gly Ala Gly His Thr Met Pro Ser Thr Asn
1               5                   10                  15

Ile Arg Gln Ala
            20

<210> SEQ ID NO 244
<211> LENGTH: 20
<212> TYPE: PRT
<213> ORGANISM: artificial sequence
<220> FEATURE:
<223> OTHER INFORMATION: Synthetic construct

<400> SEQUENCE: 244

Asn Pro Thr Ala Thr Pro His Met Lys Asp Pro Met His Ser Asn Ala
1               5                   10                  15

His Ser Ser Ala
            20

<210> SEQ ID NO 245
<211> LENGTH: 20
<212> TYPE: PRT
<213> ORGANISM: artificial sequence
<220> FEATURE:
<223> OTHER INFORMATION: Synthetic construct

<400> SEQUENCE: 245

Asn Pro Thr Asp His Ile Pro Ala Asn Ser Thr Asn Ser Arg Val Ser
1               5                   10                  15

Lys Gly Asn Thr
            20

<210> SEQ ID NO 246
<211> LENGTH: 15
<212> TYPE: PRT
<213> ORGANISM: artificial sequence
<220> FEATURE:
<223> OTHER INFORMATION: Synthetic construct

<400> SEQUENCE: 246

Asn Pro Thr Asp Ser Thr His Met Met His Ala Arg Asn His Glu
1               5                   10                  15

<210> SEQ ID NO 247
<211> LENGTH: 14
<212> TYPE: PRT
<213> ORGANISM: artificial sequence
<220> FEATURE:
<223> OTHER INFORMATION: Synthetic construct

<400> SEQUENCE: 247

Gln His Cys Ile Thr Glu Arg Leu His Pro Pro Cys Thr Lys
1               5                   10

<210> SEQ ID NO 248
<211> LENGTH: 14
<212> TYPE: PRT
<213> ORGANISM: artificial sequence
<220> FEATURE:
<223> OTHER INFORMATION: Synthetic construct

<400> SEQUENCE: 248

Thr Pro Cys Ala Pro Ala Ser Phe Asn Pro His Cys Ser Arg
1               5                   10
```

```
<210> SEQ ID NO 249
<211> LENGTH: 14
<212> TYPE: PRT
<213> ORGANISM: artificial sequence
<220> FEATURE:
<223> OTHER INFORMATION: Synthetic construct

<400> SEQUENCE: 249

Thr Pro Cys Ala Thr Tyr Pro His Phe Ser Gly Cys Arg Ala
1               5                   10

<210> SEQ ID NO 250
<211> LENGTH: 20
<212> TYPE: PRT
<213> ORGANISM: artificial sequence
<220> FEATURE:
<223> OTHER INFORMATION: Synthetic construct

<400> SEQUENCE: 250

Trp Cys Thr Asp Phe Cys Thr Arg Ser Thr Pro Thr Ser Thr Ser Arg
1               5                   10                  15

Ser Thr Thr Ser
            20

<210> SEQ ID NO 251
<211> LENGTH: 20
<212> TYPE: PRT
<213> ORGANISM: artificial sequence
<220> FEATURE:
<223> OTHER INFORMATION: Synthetic construct

<400> SEQUENCE: 251

Ala Pro Pro Leu Lys Thr Tyr Met Gln Glu Arg Glu Leu Thr Met Ser
1               5                   10                  15

Gln Asn Lys Asp
            20

<210> SEQ ID NO 252
<211> LENGTH: 20
<212> TYPE: PRT
<213> ORGANISM: artificial sequence
<220> FEATURE:
<223> OTHER INFORMATION: Synthetic construct

<400> SEQUENCE: 252

Glu Pro Pro Thr Arg Thr Arg Val Asn Asn His Thr Val Thr Val Gln
1               5                   10                  15

Ala Gln Gln His
            20

<210> SEQ ID NO 253
<211> LENGTH: 14
<212> TYPE: PRT
<213> ORGANISM: artificial sequence
<220> FEATURE:
<223> OTHER INFORMATION: Synthetic construct

<400> SEQUENCE: 253

Gly Tyr Cys Leu Arg Gly Asp Glu Pro Ala Val Cys Ser Gly
1               5                   10

<210> SEQ ID NO 254
<211> LENGTH: 20
<212> TYPE: PRT
<213> ORGANISM: artificial sequence
```

```
<220> FEATURE:
<223> OTHER INFORMATION: Synthetic construct

<400> SEQUENCE: 254

Leu Ser Ser Lys Asp Phe Gly Val Thr Asn Thr Asp Gln Arg Thr Tyr
1               5                   10                  15

Asp Tyr Thr Thr
            20

<210> SEQ ID NO 255
<211> LENGTH: 14
<212> TYPE: PRT
<213> ORGANISM: artificial sequence
<220> FEATURE:
<223> OTHER INFORMATION: Synthetic construct

<400> SEQUENCE: 255

Asn Phe Cys Glu Thr Gln Leu Asp Leu Ser Val Cys Thr Val
1               5                   10

<210> SEQ ID NO 256
<211> LENGTH: 14
<212> TYPE: PRT
<213> ORGANISM: artificial sequence
<220> FEATURE:
<223> OTHER INFORMATION: Synthetic construct

<400> SEQUENCE: 256

Asn Thr Cys Gln Pro Thr Lys Asn Ala Thr Pro Cys Ser Ala
1               5                   10

<210> SEQ ID NO 257
<211> LENGTH: 20
<212> TYPE: PRT
<213> ORGANISM: artificial sequence
<220> FEATURE:
<223> OTHER INFORMATION: Synthetic construct

<400> SEQUENCE: 257

Pro Ser Glu Pro Glu Arg Arg Asp Arg Asn Ile Ala Ala Asn Ala Gly
1               5                   10                  15

Arg Phe Asn Thr
            20

<210> SEQ ID NO 258
<211> LENGTH: 18
<212> TYPE: PRT
<213> ORGANISM: artificial sequence
<220> FEATURE:
<223> OTHER INFORMATION: Synthetic construct

<400> SEQUENCE: 258

Thr His Asn Met Ser His Phe Pro Pro Ser Gly His Pro Lys Arg Thr
1               5                   10                  15

Ala Thr

<210> SEQ ID NO 259
<211> LENGTH: 14
<212> TYPE: PRT
<213> ORGANISM: artificial sequence
<220> FEATURE:
<223> OTHER INFORMATION: Synthetic construct

<400> SEQUENCE: 259

Thr Thr Cys Pro Thr Met Gly Thr Tyr His Val Cys Trp Leu
```

```
<210> SEQ ID NO 260
<211> LENGTH: 20
<212> TYPE: PRT
<213> ORGANISM: artificial sequence
<220> FEATURE:
<223> OTHER INFORMATION: Synthetic construct

<400> SEQUENCE: 260

Tyr Cys Ala Asp His Thr Pro Asp Pro Ala Asn Pro Asn Lys Ile Cys
1               5                   10                  15

Gly Tyr Ser His
            20

<210> SEQ ID NO 261
<211> LENGTH: 20
<212> TYPE: PRT
<213> ORGANISM: artificial sequence
<220> FEATURE:
<223> OTHER INFORMATION: Synthetic construct

<400> SEQUENCE: 261

Ala Ala Asn Pro His Thr Glu Trp Asp Arg Asp Ala Phe Gln Leu Ala
1               5                   10                  15

Met Pro Pro Lys
            20

<210> SEQ ID NO 262
<211> LENGTH: 20
<212> TYPE: PRT
<213> ORGANISM: artificial sequence
<220> FEATURE:
<223> OTHER INFORMATION: Synthetic construct

<400> SEQUENCE: 262

Asp Leu His Pro Met Asp Pro Ser Asn Lys Arg Pro Asp Asn Pro Ser
1               5                   10                  15

Asp Leu His Thr
            20

<210> SEQ ID NO 263
<211> LENGTH: 14
<212> TYPE: PRT
<213> ORGANISM: artificial sequence
<220> FEATURE:
<223> OTHER INFORMATION: Synthetic construct

<400> SEQUENCE: 263

Glu Ser Cys Val Ser Asn Ala Leu Met Asn Gln Cys Ile Tyr
1               5                   10

<210> SEQ ID NO 264
<211> LENGTH: 20
<212> TYPE: PRT
<213> ORGANISM: artificial sequence
<220> FEATURE:
<223> OTHER INFORMATION: Synthetic construct

<400> SEQUENCE: 264

His Asn Lys Ala Asp Ser Trp Asp Pro Asp Leu Pro Pro His Ala Gly
1               5                   10                  15

Met Ser Leu Gly
            20
```

<210> SEQ ID NO 265
<211> LENGTH: 20
<212> TYPE: PRT
<213> ORGANISM: artificial sequence
<220> FEATURE:
<223> OTHER INFORMATION: Synthetic construct

<400> SEQUENCE: 265

Leu Asn Asp Gln Arg Lys Pro Gly Pro Thr Met Pro Thr His Ser
1               5                   10                  15

Pro Ala Val Gly
            20

<210> SEQ ID NO 266
<211> LENGTH: 14
<212> TYPE: PRT
<213> ORGANISM: artificial sequence
<220> FEATURE:
<223> OTHER INFORMATION: Synthetic construct

<400> SEQUENCE: 266

Asn Thr Cys Ala Thr Ser Pro Asn Ser Tyr Thr Cys Ser Asn
1               5                   10

<210> SEQ ID NO 267
<211> LENGTH: 14
<212> TYPE: PRT
<213> ORGANISM: artificial sequence
<220> FEATURE:
<223> OTHER INFORMATION: Synthetic construct

<400> SEQUENCE: 267

Ser Asp Cys Thr Ala Gly Leu Val Pro Pro Leu Cys Ala Thr
1               5                   10

<210> SEQ ID NO 268
<211> LENGTH: 20
<212> TYPE: PRT
<213> ORGANISM: artificial sequence
<220> FEATURE:
<223> OTHER INFORMATION: Synthetic construct

<400> SEQUENCE: 268

Thr Ile Glu Ser Ser Gln His Ser Arg Thr His Gln Gln Asn Tyr Gly
1               5                   10                  15

Ser Thr Lys Thr
            20

<210> SEQ ID NO 269
<211> LENGTH: 20
<212> TYPE: PRT
<213> ORGANISM: artificial sequence
<220> FEATURE:
<223> OTHER INFORMATION: Synthetic construct

<400> SEQUENCE: 269

Val Gly Thr Met Lys Gln His Pro Thr Thr Thr Gln Pro Pro Arg Val
1               5                   10                  15

Ser Ala Thr Asn
            20

<210> SEQ ID NO 270
<211> LENGTH: 20
<212> TYPE: PRT
<213> ORGANISM: artificial sequence

```
<220> FEATURE:
<223> OTHER INFORMATION: Synthetic construct

<400> SEQUENCE: 270

Tyr Ser Glu Thr Pro Asn Asp Gln Lys Pro Asn Pro His Tyr Lys Val
1               5                   10                  15

Ser Gly Thr Lys
            20

<210> SEQ ID NO 271
<211> LENGTH: 12
<212> TYPE: PRT
<213> ORGANISM: Artificial sequence
<220> FEATURE:
<223> OTHER INFORMATION: Polymethylmethacrylate binding peptides

<400> SEQUENCE: 271

Ile Pro Trp Trp Asn Ile Arg Ala Pro Leu Asn Ala
1               5                   10

<210> SEQ ID NO 272
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 272

Thr Ala Val Met Asn Val Val Asn Asn Gln Leu Ser
1               5                   10

<210> SEQ ID NO 273
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 273

Val Pro Trp Trp Ala Pro Ser Lys Leu Ser Met Gln
1               5                   10

<210> SEQ ID NO 274
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 274

Met Val Met Ala Pro His Thr Pro Arg Ala Arg Ser
1               5                   10

<210> SEQ ID NO 275
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 275

Thr Tyr Pro Asn Trp Ala His Leu Leu Ser His Tyr
1               5                   10

<210> SEQ ID NO 276
<211> LENGTH: 7
```

```
<212> TYPE: PRT
<213> ORGANISM: Artificial Sequence
<220> FEATURE:
<223> OTHER INFORMATION: Polymethylmethacrylate-binding peptide

<400> SEQUENCE: 276

Thr Pro Trp Trp Arg Ile Thr
1               5

<210> SEQ ID NO 277
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 277

Asp Leu Thr Leu Pro Phe His
1               5

<210> SEQ ID NO 278
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 278

Gly Thr Ser Ile Pro Ala Met
1               5

<210> SEQ ID NO 279
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 279

His His Lys His Val Val Ala
1               5

<210> SEQ ID NO 280
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 280

His His His Lys His Phe Met
1               5

<210> SEQ ID NO 281
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 281

His His His Arg His Gln Gly
1               5

<210> SEQ ID NO 282
<211> LENGTH: 7
<212> TYPE: PRT
```

```
<213> ORGANISM: Artificial Sequence
<220> FEATURE:
<223> OTHER INFORMATION: Polymethylmethacrylate-binding peptide

<400> SEQUENCE: 282

His His Trp His Ala Pro Arg
1               5

<210> SEQ ID NO 283
<211> LENGTH: 12
<212> TYPE: PRT
<213> ORGANISM: Artificial Sequence
<220> FEATURE:
<223> OTHER INFORMATION: Shampoo-resistant, PMMA-binding peptide

<400> SEQUENCE: 283

Ala Pro Trp His Leu Ser Ser Gln Tyr Ser Gly Thr
1               5                   10

<210> SEQ ID NO 284
<211> LENGTH: 14
<212> TYPE: PRT
<213> ORGANISM: Artificial Sequence
<220> FEATURE:
<223> OTHER INFORMATION: Shampoo-resistant PMMA-binding peptide

<400> SEQUENCE: 284

Gly Tyr Cys Leu Arg Val Asp Glu Pro Thr Val Cys Ser Gly
1               5                   10

<210> SEQ ID NO 285
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 285

His Ile His Pro Ser Asp Asn Phe Pro His Lys Asn Arg Thr His
1               5                   10                  15

<210> SEQ ID NO 286
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 286

His Thr His His Asp Thr His Lys Pro Trp Pro Thr Asp Asp His Arg
1               5                   10                  15

Asn Ser Ser Val
            20

<210> SEQ ID NO 287
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 287

Pro Glu Asp Arg Pro Ser Arg Thr Asn Ala Leu His His Asn Ala His
1               5                   10                  15

His His Asn Ala
            20
```

<210> SEQ ID NO 288
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 288

```
Thr Pro His Asn His Ala Thr Thr Asn His His Ala Gly Lys Lys
1               5                   10                  15
```

<210> SEQ ID NO 289
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 289

```
Glu Met Val Lys Asp Ser Asn Gln Arg Asn Thr Arg Ile Ser Ser
1               5                   10                  15
```

<210> SEQ ID NO 290
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 290

```
His Tyr Ser Arg Tyr Asn Pro Gly Pro His Pro Leu
1               5                   10
```

<210> SEQ ID NO 291
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 291

```
Ile Asp Thr Phe Tyr Met Ser Thr Met Ser His Ser
1               5                   10
```

<210> SEQ ID NO 292
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 292

```
Pro Met Lys Glu Ala Thr His Pro Val Pro Pro His Lys His Ser Glu
1               5                   10                  15

Thr Pro Thr Ala
            20
```

<210> SEQ ID NO 293
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 293

```
Tyr Gln Thr Ser Ser Pro Ala Lys Gln Ser Val Gly
1               5                   10
```

<210> SEQ ID NO 294
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 294

```
His Leu Pro Ser Tyr Gln Ile Thr Gln Thr His Ala Gln Tyr Arg
1               5                   10                  15
```

<210> SEQ ID NO 295
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 295

```
Thr Thr Pro Lys Thr Thr Tyr His Gln Ser Arg Ala Pro Val Thr Ala
1               5                   10                  15

Met Ser Glu Val
            20
```

<210> SEQ ID NO 296
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 296

```
Asp Arg Ile His His Lys Ser His His Val Thr Thr Asn His Phe
1               5                   10                  15
```

<210> SEQ ID NO 297
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 297

```
Trp Ala Pro Glu Lys Asp Tyr Met Gln Leu Met Lys
1               5                   10
```

<210> SEQ ID NO 298
<211> LENGTH: 12
<212> TYPE: PRT
<213> ORGANISM: Artificial sequence
<220> FEATURE:
<223> OTHER INFORMATION: Polypropylene-binding peptides

<400> SEQUENCE: 298

```
Thr Ser Asp Ile Lys Ser Arg Ser Pro His His Arg
1               5                   10
```

<210> SEQ ID NO 299
<211> LENGTH: 12
<212> TYPE: PRT
<213> ORGANISM: Artificial Sequence
<220> FEATURE:
<223> OTHER INFORMATION: Polypropylenebinding peptide

```
<400> SEQUENCE: 299

His Thr Gln Asn Met Arg Met Tyr Glu Pro Trp Phe
1               5                   10

<210> SEQ ID NO 300
<211> LENGTH: 7
<212> TYPE: PRT
<213> ORGANISM: Artificial Sequence
<220> FEATURE:
<223> OTHER INFORMATION: Polypropylene-binding peptide

<400> SEQUENCE: 300

Leu Pro Pro Gly Ser Leu Ala
1               5

<210> SEQ ID NO 301
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 301

Met Pro Ala Val Met Ser Ser Ala Gln Val Pro Arg
1               5                   10

<210> SEQ ID NO 302
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 302

Asn Gln Ser Phe Leu Pro Leu Asp Phe Pro Phe Arg
1               5                   10

<210> SEQ ID NO 303
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 303

Ser Ile Leu Ser Thr Met Ser Pro His Gly Ala Thr
1               5                   10

<210> SEQ ID NO 304
<211> LENGTH: 12
<212> TYPE: PRT
<213> ORGANISM: Artificial Sequence
<220> FEATURE:
<223> OTHER INFORMATION: Polypropylenebinding peptide

<400> SEQUENCE: 304

Ser Met Lys Tyr Ser His Ser Thr Ala Pro Ala Leu
1               5                   10

<210> SEQ ID NO 305
<211> LENGTH: 12
<212> TYPE: PRT
<213> ORGANISM: Artificial sequence
<220> FEATURE:
<223> OTHER INFORMATION: Polytetrafluoroethylene-binding peptides

<400> SEQUENCE: 305
```

```
Glu Ser Ser Tyr Ser Trp Ser Pro Ala Arg Leu Ser
1               5                   10
```

<210> SEQ ID NO 306
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 306

```
Gly Pro Leu Lys Leu Leu His Ala Trp Trp Gln Pro
1               5                   10
```

<210> SEQ ID NO 307
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 307

```
Asn Ala Leu Thr Arg Pro Val
1               5
```

<210> SEQ ID NO 308
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 308

```
Ser Ala Pro Ser Ser Lys Asn
1               5
```

<210> SEQ ID NO 309
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 309

```
Ser Val Ser Val Gly Met Lys Pro Ser Pro Arg Pro
1               5                   10
```

<210> SEQ ID NO 310
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 310

```
Ser Tyr Tyr Ser Leu Pro Pro Ile Phe His Ile Pro
1               5                   10
```

<210> SEQ ID NO 311
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 311

```
Thr Phe Thr Pro Tyr Ser Ile Thr His Ala Leu Leu
1               5                   10

<210> SEQ ID NO 312
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 312

Thr Met Gly Phe Thr Ala Pro Arg Phe Pro His Tyr
1               5                   10

<210> SEQ ID NO 313
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 313

Thr Asn Pro Phe Pro Pro Pro Ser Ser Pro Ala
1               5                   10

<210> SEQ ID NO 314
<211> LENGTH: 12
<212> TYPE: PRT
<213> ORGANISM: Artificial sequence
<220> FEATURE:
<223> OTHER INFORMATION: Polyethylene-binding peptides

<400> SEQUENCE: 314

His Asn Lys Ser Ser Pro Leu Thr Ala Ala Leu Pro
1               5                   10

<210> SEQ ID NO 315
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 315

Leu Pro Pro Trp Lys His Lys Thr Ser Gly Val Ala
1               5                   10

<210> SEQ ID NO 316
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 316

Leu Pro Trp Trp Leu Arg Asp Ser Tyr Leu Leu Pro
1               5                   10

<210> SEQ ID NO 317
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 317

Val Pro Trp Trp Lys His Pro Pro Leu Pro Val Pro
```

```
<210> SEQ ID NO 318
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 318

His His Lys Gln Trp His Asn His Pro His His Ala
1               5                   10

<210> SEQ ID NO 319
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 319

His Ile Phe Ser Ser Trp His Gln Met Trp His Arg
1               5                   10

<210> SEQ ID NO 320
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 320

Trp Pro Ala Trp Lys Thr His Pro Ile Leu Arg Met
1               5                   10

<210> SEQ ID NO 321
<211> LENGTH: 7
<212> TYPE: PRT
<213> ORGANISM: Artificial sequence
<220> FEATURE:
<223> OTHER INFORMATION: Nylon-binding peptides

<400> SEQUENCE: 321

Lys Thr Pro Pro Thr Arg Pro
1               5

<210> SEQ ID NO 322
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 322

Val Ile Asn Pro Asn Leu Asp
1               5

<210> SEQ ID NO 323
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 323

Lys Val Trp Ile Val Ser Thr
1               5
```

-continued

```
<210> SEQ ID NO 324
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 324

Ala Glu Pro Val Ala Met Leu
1               5

<210> SEQ ID NO 325
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 325

Ala Glu Leu Val Ala Met Leu
1               5

<210> SEQ ID NO 326
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 326

His Ser Leu Arg Leu Asp Trp
1               5

<210> SEQ ID NO 327
<211> LENGTH: 13
<212> TYPE: PRT
<213> ORGANISM: Artificial sequence
<220> FEATURE:
<223> OTHER INFORMATION: Polystyrene-binding peptide

<400> SEQUENCE: 327

Thr Ser Thr Ala Ser Pro Thr Met Gln Ser Lys Ile Arg
1               5                   10

<210> SEQ ID NO 328
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 328

Lys Arg Asn His Trp Gln Arg Met His Leu Ser Ala
1               5                   10

<210> SEQ ID NO 329
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 329

Ser His Ala Thr Pro Pro Gln Gly Leu Gly Pro Gln
1               5                   10
```

```
<210> SEQ ID NO 330
<211> LENGTH: 20
<212> TYPE: PRT
<213> ORGANISM: artificial sequence
<220> FEATURE:
<223> OTHER INFORMATION: cellulose acetate-binding peptide

<400> SEQUENCE: 330

Ala Thr Thr Pro Pro Ser Gly Lys Ala Ala His Ser Ala Ala Arg
1               5                   10                  15

Gln Lys Gly Asn
            20

<210> SEQ ID NO 331
<211> LENGTH: 15
<212> TYPE: PRT
<213> ORGANISM: artificial sequence
<220> FEATURE:
<223> OTHER INFORMATION: cellulose acetate-binding peptide

<400> SEQUENCE: 331

Asp Thr Ile His Pro Asn Lys Met Lys Ser Pro Ser Ser Pro Leu
1               5                   10                  15

<210> SEQ ID NO 332
<211> LENGTH: 20
<212> TYPE: PRT
<213> ORGANISM: artificial sequence
<220> FEATURE:
<223> OTHER INFORMATION: cellulose aceteate-binding peptide

<400> SEQUENCE: 332

Asn Gly Asn Asn His Thr Asp Ile Pro Asn Arg Ser Ser Tyr Thr Gly
1               5                   10                  15

Gly Ser Phe Ala
            20

<210> SEQ ID NO 333
<211> LENGTH: 15
<212> TYPE: PRT
<213> ORGANISM: ARTIFICIAL SEQUENCE
<220> FEATURE:
<223> OTHER INFORMATION: synthetic cellulose acetate-binding peptide

<400> SEQUENCE: 333

Ser Asp Glu Thr Gly Pro Gln Ile Pro His Arg Arg Pro Thr Trp
1               5                   10                  15

<210> SEQ ID NO 334
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 334

Met Pro Pro Pro Leu Met Gln
1               5

<210> SEQ ID NO 335
<211> LENGTH: 7
<212> TYPE: PRT
<213> ORGANISM: Artificial Sequence
<220> FEATURE:
<223> OTHER INFORMATION: Pigment-binding peptide
```

```
<400> SEQUENCE: 335

Phe His Glu Asn Trp Pro Ser
1               5

<210> SEQ ID NO 336
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 336

Arg Thr Ala Pro Thr Thr Pro Leu Leu Leu Ser Leu
1               5                   10

<210> SEQ ID NO 337
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 337

Trp His Leu Ser Trp Ser Pro Val Pro Leu Pro Thr
1               5                   10

<210> SEQ ID NO 338
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 338

Pro His Ala Arg Leu Val Gly
1               5

<210> SEQ ID NO 339
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 339

Asn Ile Pro Tyr His His Pro
1               5

<210> SEQ ID NO 340
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 340

Thr Thr Met Pro Ala Ile Pro
1               5

<210> SEQ ID NO 341
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 341
```

```
His Asn Leu Pro Pro Arg Ser
1               5

<210> SEQ ID NO 342
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 342

Ala His Lys Thr Gln Met Gly Val Arg Gln Pro Ala
1               5                   10

<210> SEQ ID NO 343
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 343

Ala Asp Asn Val Gln Met Gly Val Ser His Thr Pro
1               5                   10

<210> SEQ ID NO 344
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 344

Ala His Asn Ala Gln Met Gly Val Ser His Pro Pro
1               5                   10

<210> SEQ ID NO 345
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 345

Ala Asp Tyr Val Gly Met Gly Val Ser His Arg Pro
1               5                   10

<210> SEQ ID NO 346
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 346

Ser Val Ser Val Gly Met Lys Pro Ser Pro Arg Pro
1               5                   10

<210> SEQ ID NO 347
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 347
```

```
Tyr Pro Asn Thr Ala Leu Val
1               5

<210> SEQ ID NO 348
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 348

Val Ala Thr Arg Ile Val Ser
1               5

<210> SEQ ID NO 349
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 349

His Ser Leu Lys Asn Ser Met Leu Thr Val Met Ala
1               5                   10

<210> SEQ ID NO 350
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 350

Asn Tyr Pro Thr Gln Ala Pro
1               5

<210> SEQ ID NO 351
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 351

Lys Cys Cys Tyr Ser Val Gly
1               5

<210> SEQ ID NO 352
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 352

Arg His Asp Leu Asn Thr Trp Leu Pro Pro Val Lys
1               5                   10

<210> SEQ ID NO 353
<211> LENGTH: 12
<212> TYPE: PRT
<213> ORGANISM: Pigment-binding peptide

<400> SEQUENCE: 353

Glu Ile Ser Leu Pro Ala Lys Leu Pro Ser Ala Ser
1               5                   10
```

```
<210> SEQ ID NO 354
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 354

Ser Asp Tyr Val Gly Met Arg Pro Ser Pro Arg His
1               5                   10

<210> SEQ ID NO 355
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 355

Ser Asp Tyr Val Gly Met Arg Leu Ser Pro Ser Gln
1               5                   10

<210> SEQ ID NO 356
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 356

Ser Val Ser Val Gly Ile Gln Pro Ser Pro Arg Pro
1               5                   10

<210> SEQ ID NO 357
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 357

Tyr Val Ser Val Gly Ile Lys Pro Ser Pro Arg Pro
1               5                   10

<210> SEQ ID NO 358
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 358

Tyr Val Cys Glu Gly Ile His Pro Cys Pro Arg Pro
1               5                   10

<210> SEQ ID NO 359
<211> LENGTH: 12
<212> TYPE: PRT
<213> ORGANISM: artificial sequence
<220> FEATURE:
<223> OTHER INFORMATION: synthetic iron oxide pigment binding peptide

<400> SEQUENCE: 359

Trp Ala Pro Glu Lys Asp His Met Gln Leu Met Lys
1               5                   10
```

-continued

```
<210> SEQ ID NO 360
<211> LENGTH: 12
<212> TYPE: PRT
<213> ORGANISM: artificial sequence
<220> FEATURE:
<223> OTHER INFORMATION: Iron oxide-binding peptide

<400> SEQUENCE: 360

Trp Ala Pro Glu Lys Asp Tyr Met Gln Leu Met Lys
1               5                   10

<210> SEQ ID NO 361
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 361

Cys Pro Leu Asp Thr Pro Thr His Lys Thr Lys His Glu Tyr Lys Thr
1               5                   10                  15

Arg Cys Arg His
            20

<210> SEQ ID NO 362
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 362

Asp His Asp His Pro Arg Leu His Lys Arg Gln Glu Lys Ser Glu His
1               5                   10                  15

Leu His

<210> SEQ ID NO 363
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 363

Asp Ser His His Asn His His Lys Gln Asp Ser Arg Pro Gln His Arg
1               5                   10                  15

Lys Thr Pro Asn
            20

<210> SEQ ID NO 364
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 364

Glu Gly Gly Asn Ala Pro His His Lys Pro His His Arg Lys His
1               5                   10                  15

<210> SEQ ID NO 365
<211> LENGTH: 18
<212> TYPE: PRT
<213> ORGANISM: artificial sequence
<220> FEATURE:
<223> OTHER INFORMATION: Iron oxide-binding peptide
```

```
<400> SEQUENCE: 365

His Asp Ser His Arg Pro Leu Thr Gln His Gly His Arg His Ser His
1               5                   10                  15

Val Pro

<210> SEQ ID NO 366
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 366

His Asp Ser Asn His Cys Ser His Ser Thr Arg Arg Pro Asn Cys Ala
1               5                   10                  15

Arg Thr

<210> SEQ ID NO 367
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 367

Ala Thr Arg Val Asp Asn Thr Pro Ala Ser Asn Pro Pro Ser Leu
1               5                   10                  15

<210> SEQ ID NO 368
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 368

Asp Gly Ile Lys Pro Phe His Leu Met Thr Pro Thr Leu Ala Asn
1               5                   10                  15

<210> SEQ ID NO 369
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 369

Asp Ile Thr Pro Pro Gly Ser Thr His His Arg Lys Pro His Arg His
1               5                   10                  15

Gln His

<210> SEQ ID NO 370
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 370

Asp Asn Leu Trp Pro Gln Pro Leu Asn Val Glu Asp Asp Arg Tyr
1               5                   10                  15

<210> SEQ ID NO 371
```

```
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 371

Glu Asn Glu Lys His Arg His Asn Thr His Glu Ala Leu His Ser His
1               5                   10                  15

Phe Lys

<210> SEQ ID NO 372
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 372

Gly Ala Ile Trp Pro Ala Ser Ser Ala Leu Met Thr Glu His Asn Pro
1               5                   10                  15

Thr Asp Asn His
            20

<210> SEQ ID NO 373
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 373

Gly Asp Thr Asn Gln Asp Thr Val Met Trp Tyr Tyr Thr Val Asn
1               5                   10                  15

<210> SEQ ID NO 374
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 374

His Asn Gly Pro Tyr Gly Met Leu Ser Thr Gly Lys Ile His Phe
1               5                   10                  15

<210> SEQ ID NO 375
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 375

Leu Asp Gly Gly Tyr Arg Asp Thr Pro Asp Asn Tyr Leu Lys Gly
1               5                   10                  15

<210> SEQ ID NO 376
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 376

Leu His Thr Lys Thr Glu Asn Ser His Thr Asn Met Lys Thr Thr
```

```
<210> SEQ ID NO 377
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 377

Asn Ala Gln Tyr Asp Pro Pro Thr Leu Asn Lys Gly Ala Val Arg Lys
1               5                   10                  15

Ala Ala Ser Thr
            20

<210> SEQ ID NO 378
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 378

Asn Gly Asn Asn His Thr Asp Ile Pro Asn Arg Ser Ser Tyr Thr
1               5                   10                  15

<210> SEQ ID NO 379
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 379

Gln Ser Thr Asn His His His Pro His Ala Lys His Pro Arg Val Asn
1               5                   10                  15

Thr His

<210> SEQ ID NO 380
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 380

Ser Asn Asn Asp Tyr Val Gly Thr Tyr Pro Ala Thr Ala Ile Gln
1               5                   10                  15

<210> SEQ ID NO 381
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 381

Ser Thr Gln His Asn Leu His Asp Arg Asn Ile Tyr Phe Val Ser
1               5                   10                  15

<210> SEQ ID NO 382
<211> LENGTH: 20
<212> TYPE: PRT
<213> ORGANISM: artificial sequence
<220> FEATURE:
<223> OTHER INFORMATION: Iron oxide-binding peptide
```

<400> SEQUENCE: 382

Thr Ala Asn Asn Lys Thr Pro Ala Gly Ala Pro Asn Ala Ala Val Gly
1               5                   10                  15

Leu Ala Gln Arg
            20

<210> SEQ ID NO 383
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 383

Thr Glu Pro Thr Arg Ile Ser Asn Tyr Arg Ser Ile Pro Asn Asp
1               5                   10                  15

<210> SEQ ID NO 384
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 384

Thr His Asn Pro Arg Glu His Ala Arg His His His Asn Glu Tyr
1               5                   10                  15

Lys His

<210> SEQ ID NO 385
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 385

Thr His Pro Pro Cys Trp Tyr Glu Thr Asn Cys Ile Val Gln Glu
1               5                   10                  15

<210> SEQ ID NO 386
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 386

Thr Thr Asn Pro His Lys Pro Ala Ser His His His Asp His Arg Pro
1               5                   10                  15

Ala Leu Arg His
            20

<210> SEQ ID NO 387
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 387

Trp Leu Val Ala Asp Asn Ala Thr Asp Gly His Ser His Gln Lys
1               5                   10                  15

```
<210> SEQ ID NO 388
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 388

Tyr Thr Asp Ser Met Ser Asp Gln Thr Pro Glu Phe Ala Lys Tyr
1               5                   10                  15

<210> SEQ ID NO 389
<211> LENGTH: 7
<212> TYPE: PRT
<213> ORGANISM: Artificial Sequence
<220> FEATURE:
<223> OTHER INFORMATION: Print Media Binding Peptide

<400> SEQUENCE: 389

Ser Ile Leu Pro Tyr Pro Tyr
1               5

<210> SEQ ID NO 390
<211> LENGTH: 7
<212> TYPE: PRT
<213> ORGANISM: Artificial Sequence
<220> FEATURE:
<223> OTHER INFORMATION: Cotton Binding Peptide

<400> SEQUENCE: 390

Ser Thr Ala Ser Tyr Thr Arg
1               5

<210> SEQ ID NO 391
<211> LENGTH: 7
<212> TYPE: PRT
<213> ORGANISM: Artificial Sequence
<220> FEATURE:
<223> OTHER INFORMATION: Polyester/Cotton Binding Peptide

<400> SEQUENCE: 391

Leu Pro Val Arg Pro Trp Thr
1               5

<210> SEQ ID NO 392
<211> LENGTH: 7
<212> TYPE: PRT
<213> ORGANISM: Artificial Sequence
<220> FEATURE:
<223> OTHER INFORMATION: Paper Binding Peptide

<400> SEQUENCE: 392

Gly Asn Thr Pro Ser Arg Ala
1               5

<210> SEQ ID NO 393
<211> LENGTH: 7
<212> TYPE: PRT
<213> ORGANISM: Artificial Sequence
<220> FEATURE:
<223> OTHER INFORMATION: Paper Binding Peptide

<400> SEQUENCE: 393

His Ala Ile Tyr Pro Arg His
1               5
```

```
<210> SEQ ID NO 394
<211> LENGTH: 7
<212> TYPE: PRT
<213> ORGANISM: Artificial Sequence
<220> FEATURE:
<223> OTHER INFORMATION: Paper Binding Peptide

<400> SEQUENCE: 394

Tyr Gln Asp Ser Ala Lys Thr
1               5

<210> SEQ ID NO 395
<211> LENGTH: 7
<212> TYPE: PRT
<213> ORGANISM: Artificial Sequence
<220> FEATURE:
<223> OTHER INFORMATION: Cellulose Binding Peptide

<400> SEQUENCE: 395

Val Pro Arg Val Thr Ser Ile
1               5

<210> SEQ ID NO 396
<211> LENGTH: 7
<212> TYPE: PRT
<213> ORGANISM: Artificial Sequence
<220> FEATURE:
<223> OTHER INFORMATION: Cellulose Binding Peptide

<400> SEQUENCE: 396

Met Ala Asn His Asn Leu Ser
1               5

<210> SEQ ID NO 397
<211> LENGTH: 7
<212> TYPE: PRT
<213> ORGANISM: Artificial Sequence
<220> FEATURE:
<223> OTHER INFORMATION: Pigment Binding and Cellulose Binding Peptide

<400> SEQUENCE: 397

Phe His Glu Asn Trp Pro Ser
1               5

<210> SEQ ID NO 398
<211> LENGTH: 12
<212> TYPE: PRT
<213> ORGANISM: Artificial Sequence
<220> FEATURE:
<223> OTHER INFORMATION: Cellulose Binding Peptide

<400> SEQUENCE: 398

Thr His Lys Thr Ser Thr Gln Arg Leu Leu Ala Ala
1               5                   10

<210> SEQ ID NO 399
<211> LENGTH: 12
<212> TYPE: PRT
<213> ORGANISM: Artificial Sequence
<220> FEATURE:
<223> OTHER INFORMATION: Cellulose Binding Peptide

<400> SEQUENCE: 399

Lys Cys Cys Tyr Val Asn Val Gly Ser Val Phe Ser
1               5                   10

<210> SEQ ID NO 400
```

<211> LENGTH: 12
<212> TYPE: PRT
<213> ORGANISM: Artificial Sequence
<220> FEATURE:
<223> OTHER INFORMATION: Cellulose Binding Peptide

<400> SEQUENCE: 400

Ala His Met Gln Phe Arg Thr Ser Leu Thr Pro His
1               5                   10

<210> SEQ ID NO 401
<211> LENGTH: 27
<212> TYPE: PRT
<213> ORGANISM: artificial sequence
<220> FEATURE:
<223> OTHER INFORMATION: Clay-binding peptide

<400> SEQUENCE: 401

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 402
<211> LENGTH: 27
<212> TYPE: PRT
<213> ORGANISM: artificial sequence
<220> FEATURE:
<223> OTHER INFORMATION: Clay-binding peptide

<400> SEQUENCE: 402

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25

<210> SEQ ID NO 403
<211> LENGTH: 27
<212> TYPE: PRT
<213> ORGANISM: artificial sequence
<220> FEATURE:
<223> OTHER INFORMATION: Clay-binding peptide

<400> SEQUENCE: 403

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25

<210> SEQ ID NO 404
<211> LENGTH: 27
<212> TYPE: PRT
<213> ORGANISM: artificial sequence
<220> FEATURE:
<223> OTHER INFORMATION: Clay-binding peptide

<400> SEQUENCE: 404

Lys Lys Ser Asn Lys Gly Pro His Pro Ser Ser Lys Gly Lys Gly Pro
1               5                   10                  15

Pro Trp Ser Glu Trp Asp Lys Lys Asn Gly Pro
            20                  25

<210> SEQ ID NO 405
<211> LENGTH: 22
<212> TYPE: PRT

```
<213> ORGANISM: artificial sequence
<220> FEATURE:
<223> OTHER INFORMATION: Clay-binding peptide

<400> SEQUENCE: 405

Val Gly Arg His His Ser Lys Ala Lys Gln Lys Arg Pro His Gly Gly
1               5                   10                  15

Lys Gly Gln Asn Lys Asn
            20

<210> SEQ ID NO 406
<211> LENGTH: 22
<212> TYPE: PRT
<213> ORGANISM: artificial sequence
<220> FEATURE:
<223> OTHER INFORMATION: Clay-binding peptide

<400> SEQUENCE: 406

Val Gly Arg His His Pro Lys Ala Lys Gln Lys Arg Pro His Gly Gly
1               5                   10                  15

Lys Gly Gln Asn Lys Asn
            20

<210> SEQ ID NO 407
<211> LENGTH: 17
<212> TYPE: PRT
<213> ORGANISM: artificial sequence
<220> FEATURE:
<223> OTHER INFORMATION: Clay-binding peptide

<400> SEQUENCE: 407

Gly Arg Arg Pro Arg Ala Arg Gly Arg Ser Arg Arg Gly Ser Thr Lys
1               5                   10                  15

Thr

<210> SEQ ID NO 408
<211> LENGTH: 19
<212> TYPE: PRT
<213> ORGANISM: artificial sequence
<220> FEATURE:
<223> OTHER INFORMATION: Clay-binding peptide

<400> SEQUENCE: 408

Leu Gly Val Ile Arg Asn His Val Val Arg Gly Arg Arg His His Gln
1               5                   10                  15

His Val Arg

<210> SEQ ID NO 409
<211> LENGTH: 27
<212> TYPE: PRT
<213> ORGANISM: artificial sequence
<220> FEATURE:
<223> OTHER INFORMATION: Clay-binding peptide

<400> SEQUENCE: 409

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 410
<211> LENGTH: 27
<212> TYPE: PRT
<213> ORGANISM: artificial sequence
```

```
<220> FEATURE:
<223> OTHER INFORMATION: Clay-binding peptide

<400> SEQUENCE: 410

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25

<210> SEQ ID NO 411
<211> LENGTH: 27
<212> TYPE: PRT
<213> ORGANISM: artificial sequence
<220> FEATURE:
<223> OTHER INFORMATION: Clay-binding peptide

<400> SEQUENCE: 411

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 412
<211> LENGTH: 27
<212> TYPE: PRT
<213> ORGANISM: artificial sequence
<220> FEATURE:
<223> OTHER INFORMATION: Clay-binding peptide

<400> SEQUENCE: 412

Val Gly Glu Lys Pro Arg Arg Lys Ser Lys Gly Ala Lys Ala Lys Lys
1               5                   10                  15

Ala Arg Thr Lys Glu Glu Lys Leu Pro Lys Asn
            20                  25

<210> SEQ ID NO 413
<211> LENGTH: 27
<212> TYPE: PRT
<213> ORGANISM: artificial sequence
<220> FEATURE:
<223> OTHER INFORMATION: Clay-binding peptide

<400> SEQUENCE: 413

Asn Lys Gly His Lys Gln Ser Gly Ser Pro Arg His Ser Asn Lys Lys
1               5                   10                  15

Glu Lys Lys Thr Gln Gln Lys Arg Gly Gln Pro
            20                  25

<210> SEQ ID NO 414
<211> LENGTH: 27
<212> TYPE: PRT
<213> ORGANISM: artificial sequence
<220> FEATURE:
<223> OTHER INFORMATION: Clay-binding peptide

<400> SEQUENCE: 414

His Trp Gly Ser Gln His Lys Thr Gly Leu Arg Asn His Lys Arg Ser
1               5                   10                  15

Arg Arg Asp Ser Leu Gly Lys Arg Gly Thr Asp
            20                  25

<210> SEQ ID NO 415
<211> LENGTH: 27
<212> TYPE: PRT
```

<213> ORGANISM: artificial sequence
<220> FEATURE:
<223> OTHER INFORMATION: Clay-binding peptide

<400> SEQUENCE: 415

Lys Gly Trp Gly Ser Ser Ser Gly Pro Pro Gly Leu Thr Gly Lys Ala
1               5                   10                  15

Leu Gly Lys Gly Arg Leu Lys Pro Lys Lys Lys
            20                  25

<210> SEQ ID NO 416
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 416

Arg Asn Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 417
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 417

Arg Asn Asn Lys Gly Ser Lys Lys Val Asp Asp Lys Arg Arg Lys Thr
1               5                   10                  15

Val His Asn Thr Lys Ser Arg Ala Lys His Ser
            20                  25

<210> SEQ ID NO 418
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 418

Arg Asp Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 419
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 419

Arg Asn Asn Lys Gly Ser Lys Lys Val Asp Asp Lys Arg Arg Lys Thr
1               5                   10                  15

Val His Ser Thr Lys Ser Arg Ala Lys Tyr Ser
            20                  25

<210> SEQ ID NO 420
<211> LENGTH: 27

```
<212> TYPE: PRT
<213> ORGANISM: artificial sequence
<220> FEATURE:
<223> OTHER INFORMATION: Calcium carbonate binding peptide

<400> SEQUENCE: 420

Arg Asn Asn Lys Gly Ser Arg Lys Val Asp Asp Lys Arg Lys Thr
1               5                   10                  15

Val His Asn Thr Lys Ser Arg Ala Lys Tyr Ser
            20                  25

<210> SEQ ID NO 421
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 421

Arg Asn Asn Lys Gly Ser Lys Lys Ala Asp Asp Lys Arg Arg Lys Thr
1               5                   10                  15

Val His Ser Thr Lys Ser Arg Ala Lys Tyr Ser
            20                  25

<210> SEQ ID NO 422
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 422

Arg Asn Asn Lys Gly Ser Lys Lys Val Asp Asp Lys Arg Arg Lys Ala
1               5                   10                  15

Val His Asn Lys Lys Ser Arg Ala Lys Tyr Ser
            20                  25

<210> SEQ ID NO 423
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 423

Arg Asn Asn Lys Gly Ser Lys Lys Val Asp Asp Lys Arg Arg Lys Thr
1               5                   10                  15

Val His Asn Thr Arg Ser Arg Ala Lys Tyr Ser
            20                  25

<210> SEQ ID NO 424
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 424

Arg Asn Asn Lys Gly Ser Lys Lys Val Asp Asp Lys Arg Arg Lys Thr
1               5                   10                  15

Val His Asn Thr Lys Ser Arg Ala Lys Phe Ser
            20                  25

<210> SEQ ID NO 425
```

```
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 425

Gln Arg Arg Lys Leu Arg His Pro Lys Glu Lys Trp Phe Gly Trp Ser
1               5                   10                  15

Glu Lys Lys Val Ile Lys Lys Trp Ser Arg Lys
            20                  25

<210> SEQ ID NO 426
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (23)..(23)
<223> OTHER INFORMATION: Xaa = any naturally occurring amino acid

<400> SEQUENCE: 426

Gln Arg Arg Lys Phe Arg His Pro Lys Glu Lys Trp Phe Gly Trp Ser
1               5                   10                  15

Glu Lys Lys Val Ile Lys Xaa Asn Gly Arg Pro
            20                  25

<210> SEQ ID NO 427
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 427

His Lys Arg Leu Val Gln Asn Lys Pro His Arg Thr Arg Lys Ile Glu
1               5                   10                  15

Gly Trp Ile Lys His Met Val Lys Arg Gln His
            20                  25

<210> SEQ ID NO 428
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 428

Thr Arg Gly His Ile Met Arg Pro Cys Trp Ile Gly Ala Met Lys Gln
1               5                   10                  15

Gly Val Lys Lys Lys Arg Thr Pro Gly Trp Arg
            20                  25

<210> SEQ ID NO 429
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 429

Trp Lys Val Lys Arg Arg Met Val Thr Arg Thr Tyr Glu Phe Met Gly
1               5                   10                  15
```

```
Lys Lys Pro Cys Met Met Leu Thr Lys Arg Leu
            20                  25
```

<210> SEQ ID NO 430
<211> LENGTH: 26
<212> TYPE: PRT
<213> ORGANISM: artificial sequence
<220> FEATURE:
<223> OTHER INFORMATION: Calcium carbonate binding peptide

<400> SEQUENCE: 430

```
Lys Lys Ser Asn Lys Gly His His Ser Lys Ala Lys Gln Lys Arg Pro
1               5                   10                  15

His Gly Gly Lys Ala Gln Asn Lys Asn Thr
            20                  25
```

<210> SEQ ID NO 431
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 431

```
Arg Ala His Lys Glu Arg Phe Val Val Arg Gln Ile Gly Arg Ser Gln
1               5                   10                  15

Gly Tyr Lys Thr Trp Gln Cys Val Arg Val Ala
            20                  25
```

<210> SEQ ID NO 432
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 432

```
Ser Gln Lys Pro Lys Gly His Lys Val Lys Val Val Lys Leu Cys
1               5                   10                  15

Lys Arg Pro Tyr Trp Arg Met Leu Asn Thr Ala
            20                  25
```

<210> SEQ ID NO 433
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (11)..(11)
<223> OTHER INFORMATION: Xaa = any naturally occurring amino acid

<400> SEQUENCE: 433

```
Asn His Gly Cys Pro Val Asn Trp Lys Val Xaa Asn Pro Pro Arg Gly
1               5                   10                  15

Trp Gln Arg Leu Asn His Cys Lys Trp Trp Asn
            20                  25
```

<210> SEQ ID NO 434
<211> LENGTH: 27
<212> TYPE: PRT
<213> ORGANISM: artificial sequence
<220> FEATURE:
<223> OTHER INFORMATION: Calcium carbonate binding peptide

```
<400> SEQUENCE: 434

Arg Asn Ser Arg His Lys Glu Trp Arg Arg Tyr Lys Arg Thr His Val
1               5                   10                  15

His Ser His Glu Phe Tyr His Val Glu Cys Trp
            20                  25

<210> SEQ ID NO 435
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 435

His Arg Ser Glu Lys Pro Lys Asn Val Asn Tyr Lys Arg Gly Tyr Trp
1               5                   10                  15

Glu Arg Gly Asn Gln Lys Lys His Gly Pro Gly
            20                  25

<210> SEQ ID NO 436
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 436

His Glu Arg Thr Arg Arg Gly Lys Pro Asp Arg Gln Lys Thr Thr His
1               5                   10                  15

Glu Lys Arg Arg Gln Gly Leu Trp Ile Phe Met
            20                  25

<210> SEQ ID NO 437
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 437

Pro Trp Gly Thr Asn Lys Arg Gln Lys His Lys Val His Glu Ala Lys
1               5                   10                  15

Ala Leu Lys Lys Ser Leu Trp Tyr Ser Asn Ser
            20                  25

<210> SEQ ID NO 438
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 438

Arg Arg Gly Val Val Leu Cys His Thr His Arg Asn Lys Arg Ile Arg
1               5                   10                  15

Leu Ala Tyr Ser Val Thr Lys Lys Ala Trp Ala
            20                  25

<210> SEQ ID NO 439
<211> LENGTH: 27
<212> TYPE: PRT
<213> ORGANISM: artificial sequence
<220> FEATURE:
<223> OTHER INFORMATION: Calcium carbonate binding peptide
```

```
<400> SEQUENCE: 439

Glu Arg Ile Arg Trp Arg Arg Leu Ser Ala Glu Ile Arg Ala His Lys
1               5                   10                  15

Trp Ser Val Leu Lys Phe Arg Leu Ser Cys Met
            20                  25

<210> SEQ ID NO 440
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 440

Lys Thr Lys Glu Lys Lys Glu Val Lys Leu His Lys Lys Ser Leu
1               5                   10                  15

Ser Leu Val Leu Leu Ala Asp Leu Trp Arg Leu
            20                  25

<210> SEQ ID NO 441
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 441

Leu Gly Lys Lys His Lys Gln His Ser Lys Val Gly His Gly Lys Leu
1               5                   10                  15

Ser Thr Arg Phe Leu Arg Arg Ser Lys Leu Phe
            20                  25

<210> SEQ ID NO 442
<211> LENGTH: 17
<212> TYPE: PRT
<213> ORGANISM: artificial sequence
<220> FEATURE:
<223> OTHER INFORMATION: Antimicrobial peptide

<400> SEQUENCE: 442

Pro Lys Gly Leu Lys Lys Leu Leu Lys Gly Leu Lys Lys Leu Leu Lys
1               5                   10                  15

Leu

<210> SEQ ID NO 443
<211> LENGTH: 16
<212> TYPE: PRT
<213> ORGANISM: artificial sequence
<220> FEATURE:
<223> OTHER INFORMATION: Antimicrobial peptide

<400> SEQUENCE: 443

Lys Gly Leu Lys Lys Leu Leu Lys Gly Leu Lys Lys Leu Leu Lys Leu
1               5                   10                  15

<210> SEQ ID NO 444
<211> LENGTH: 16
<212> TYPE: PRT
<213> ORGANISM: artificial sequence
<220> FEATURE:
<223> OTHER INFORMATION: Antimicrobial peptide

<400> SEQUENCE: 444
```

```
Lys Gly Leu Lys Lys Leu Leu Lys Leu Leu Lys Lys Leu Leu Lys Leu
1               5                   10                  15
```

<210> SEQ ID NO 445
<211> LENGTH: 14
<212> TYPE: PRT
<213> ORGANISM: artificial sequence
<220> FEATURE:
<223> OTHER INFORMATION: Antimicrobial peptide

<400> SEQUENCE: 445

```
Leu Lys Lys Leu Leu Lys Leu Leu Lys Lys Leu Leu Lys Leu
1               5                   10
```

<210> SEQ ID NO 446
<211> LENGTH: 12
<212> TYPE: PRT
<213> ORGANISM: artificial sequence
<220> FEATURE:
<223> OTHER INFORMATION: Antimicrobial peptide

<400> SEQUENCE: 446

```
Leu Lys Lys Leu Leu Lys Leu Leu Lys Lys Leu Leu
1               5                   10
```

<210> SEQ ID NO 447
<211> LENGTH: 17
<212> TYPE: PRT
<213> ORGANISM: artificial sequence
<220> FEATURE:
<223> OTHER INFORMATION: Antimicrobial peptide

<400> SEQUENCE: 447

```
Val Ala Lys Lys Leu Ala Lys Leu Ala Lys Lys Leu Ala Lys Leu Ala
1               5                   10                  15
Leu
```

<210> SEQ ID NO 448
<211> LENGTH: 13
<212> TYPE: PRT
<213> ORGANISM: artificial sequence
<220> FEATURE:
<223> OTHER INFORMATION: Antimicrobial peptide

<400> SEQUENCE: 448

```
Phe Ala Lys Leu Leu Ala Lys Ala Leu Lys Lys Leu Leu
1               5                   10
```

<210> SEQ ID NO 449
<211> LENGTH: 16
<212> TYPE: PRT
<213> ORGANISM: artificial sequence
<220> FEATURE:
<223> OTHER INFORMATION: Antimicrobial peptide

<400> SEQUENCE: 449

```
Lys Gly Leu Lys Lys Gly Leu Lys Leu Leu Lys Lys Leu Leu Lys Leu
1               5                   10                  15
```

<210> SEQ ID NO 450
<211> LENGTH: 16
<212> TYPE: PRT
<213> ORGANISM: artificial sequence
<220> FEATURE:
<223> OTHER INFORMATION: Antimicrobial peptide

<400> SEQUENCE: 450

Lys Gly Leu Lys Lys Leu Leu Lys Leu Gly Lys Lys Leu Leu Lys Leu
1               5                   10                  15

<210> SEQ ID NO 451
<211> LENGTH: 16
<212> TYPE: PRT
<213> ORGANISM: artificial sequence
<220> FEATURE:
<223> OTHER INFORMATION: Antimicrobial peptide

<400> SEQUENCE: 451

Lys Gly Leu Lys Lys Leu Gly Lys Leu Leu Lys Lys Leu Leu Lys Leu
1               5                   10                  15

<210> SEQ ID NO 452
<211> LENGTH: 16
<212> TYPE: PRT
<213> ORGANISM: artificial sequence
<220> FEATURE:
<223> OTHER INFORMATION: Antimicrobial peptide

<400> SEQUENCE: 452

Lys Gly Leu Lys Lys Leu Leu Lys Leu Leu Lys Lys Gly Leu Lys Leu
1               5                   10                  15

<210> SEQ ID NO 453
<211> LENGTH: 16
<212> TYPE: PRT
<213> ORGANISM: artificial sequence
<220> FEATURE:
<223> OTHER INFORMATION: Antimicrobial peptide

<400> SEQUENCE: 453

Lys Gly Leu Lys Lys Leu Leu Lys Leu Leu Lys Lys Leu Gly Lys Leu
1               5                   10                  15

<210> SEQ ID NO 454
<211> LENGTH: 19
<212> TYPE: PRT
<213> ORGANISM: artificial sequence
<220> FEATURE:
<223> OTHER INFORMATION: Antimicrobial peptide

<400> SEQUENCE: 454

Phe Ala Leu Ala Leu Lys Ala Leu Lys Lys Leu Lys Lys Ala Leu Lys
1               5                   10                  15

Lys Ala Leu

<210> SEQ ID NO 455
<211> LENGTH: 17
<212> TYPE: PRT
<213> ORGANISM: artificial sequence
<220> FEATURE:
<223> OTHER INFORMATION: Antimicrobial peptide

<400> SEQUENCE: 455

Phe Ala Lys Lys Leu Ala Lys Leu Ala Lys Lys Leu Ala Lys Leu Ala
1               5                   10                  15

Leu

<210> SEQ ID NO 456
<211> LENGTH: 13
<212> TYPE: PRT
<213> ORGANISM: artificial sequence
<220> FEATURE:

<223> OTHER INFORMATION: Antimicrobial peptide

<400> SEQUENCE: 456

Phe Ala Lys Leu Leu Ala Lys Leu Ala Lys Lys Leu Leu
1               5                   10

<210> SEQ ID NO 457
<211> LENGTH: 15
<212> TYPE: PRT
<213> ORGANISM: artificial sequence
<220> FEATURE:
<223> OTHER INFORMATION: Antimicrobial peptide

<400> SEQUENCE: 457

Phe Ala Lys Lys Leu Ala Lys Leu Ala Leu Lys Leu Ala Lys Leu
1               5                   10                  15

<210> SEQ ID NO 458
<211> LENGTH: 10
<212> TYPE: PRT
<213> ORGANISM: artificial sequence
<220> FEATURE:
<223> OTHER INFORMATION: Antimicrobial peptide

<400> SEQUENCE: 458

Phe Ala Lys Lys Leu Ala Lys Lys Leu Leu
1               5                   10

<210> SEQ ID NO 459
<211> LENGTH: 13
<212> TYPE: PRT
<213> ORGANISM: artificial sequence
<220> FEATURE:
<223> OTHER INFORMATION: Antimicrobial peptide

<400> SEQUENCE: 459

Phe Ala Lys Leu Leu Ala Lys Leu Ala Lys Lys Val Leu
1               5                   10

<210> SEQ ID NO 460
<211> LENGTH: 13
<212> TYPE: PRT
<213> ORGANISM: artificial sequence
<220> FEATURE:
<223> OTHER INFORMATION: Antimicrobial peptide

<400> SEQUENCE: 460

Lys Tyr Lys Lys Ala Leu Lys Lys Leu Ala Lys Leu Leu
1               5                   10

<210> SEQ ID NO 461
<211> LENGTH: 12
<212> TYPE: PRT
<213> ORGANISM: artificial sequence
<220> FEATURE:
<223> OTHER INFORMATION: Antimicrobial peptide

<400> SEQUENCE: 461

Phe Ala Leu Leu Lys Ala Leu Leu Lys Lys Ala Leu
1               5                   10

<210> SEQ ID NO 462
<211> LENGTH: 14
<212> TYPE: PRT
<213> ORGANISM: artificial sequence
<220> FEATURE:
<223> OTHER INFORMATION: Antimicrobial peptide

```
<400> SEQUENCE: 462

Lys Arg Leu Phe Lys Lys Leu Lys Phe Ser Leu Arg Lys Tyr
1               5                   10

<210> SEQ ID NO 463
<211> LENGTH: 14
<212> TYPE: PRT
<213> ORGANISM: artificial sequence
<220> FEATURE:
<223> OTHER INFORMATION: Antimicrobial peptide

<400> SEQUENCE: 463

Lys Arg Leu Phe Lys Lys Leu Leu Phe Ser Leu Arg Lys Tyr
1               5                   10

<210> SEQ ID NO 464
<211> LENGTH: 14
<212> TYPE: PRT
<213> ORGANISM: artificial sequence
<220> FEATURE:
<223> OTHER INFORMATION: Antimicrobial peptide

<400> SEQUENCE: 464

Leu Leu Leu Phe Leu Leu Lys Lys Arg Lys Lys Arg Lys Tyr
1               5                   10

<210> SEQ ID NO 465
<211> LENGTH: 36
<212> TYPE: PRT
<213> ORGANISM: Hyalophora cecropia

<400> SEQUENCE: 465

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
            20                  25                  30

Gln Ile Ala Lys
        35

<210> SEQ ID NO 466
<211> LENGTH: 23
<212> TYPE: PRT
<213> ORGANISM: Xenopus sp.

<400> SEQUENCE: 466

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 467
<211> LENGTH: 22
<212> TYPE: PRT
<213> ORGANISM: Xenopus sp.

<400> SEQUENCE: 467

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 468
```

```
<211> LENGTH: 12
<212> TYPE: PRT
<213> ORGANISM: Bos Taurus

<400> SEQUENCE: 468

Arg Leu Cys Arg Ile Val Val Ile Arg Val Cys Arg
1               5                   10

<210> SEQ ID NO 469
<211> LENGTH: 13
<212> TYPE: PRT
<213> ORGANISM: Bos sp.

<400> SEQUENCE: 469

Ile Leu Pro Trp Lys Trp Pro Trp Trp Pro Trp Arg Arg
1               5                   10

<210> SEQ ID NO 470
<211> LENGTH: 24
<212> TYPE: PRT
<213> ORGANISM: Homo sapiens

<400> SEQUENCE: 470

Asp Ser His Ala Lys Arg His His Gly Tyr Lys Arg Lys Phe His Glu
1               5                   10                  15

Lys His His Ser His Arg Gly Tyr
            20
```